(12) United States Patent
Rajagopalan et al.

(10) Patent No.: US 10,299,857 B2
(45) Date of Patent: May 28, 2019

(54) METHODS, SYSTEMS AND DEVICES FOR REDUCING THE LUMINAL SURFACE AREA OF THE GASTROINTESTINAL TRACT

(71) Applicant: Fractyl Laboratories, Inc., Waltham, MA (US)

(72) Inventors: Harith Rajagopalan, Brookline, MA (US); Jay Caplan, Belmont, MA (US); R. Maxwell Flaherty, Auburndale, FL (US); J. Christopher Flaherty, Auburndale, FL (US)

(73) Assignee: Fractyl Laboratories, Inc., Lexington, MA (US)

( * ) Notice: Subject to any disclaimer, the term of this patent is extended or adjusted under 35 U.S.C. 154(b) by 520 days.

(21) Appl. No.: 14/956,710

(22) Filed: Dec. 2, 2015

(65) Prior Publication Data

US 2016/0081745 A1    Mar. 24, 2016

Related U.S. Application Data

(63) Continuation of application No. PCT/US2014/040957, filed on Jun. 4, 2014.
(Continued)

(51) Int. Cl.
*A61B 18/18* (2006.01)
*A61B 18/14* (2006.01)
(Continued)

(52) U.S. Cl.
CPC .. *A61B 18/1492* (2013.01); *A61B 17/320068* (2013.01); *A61B 18/02* (2013.01);
(Continued)

(58) Field of Classification Search
CPC ........ A61B 18/1492; A61B 2018/0022; A61B 2018/00494; A61B 2018/00577;
(Continued)

(56) References Cited

U.S. PATENT DOCUMENTS 5,084,044 A  1/1992 Quint
5,190,540 A  3/1993 Lee
(Continued)

FOREIGN PATENT DOCUMENTS

CA  2666661 C  1/2015
CN  1771888 A  5/2006
(Continued)

OTHER PUBLICATIONS

European search report and search opinion dated Aug. 4, 2015 for EP Application. No. 13755156.0.
(Continued)

*Primary Examiner* — Michael F Peffley
*Assistant Examiner* — Amanda L Zink
(74) *Attorney, Agent, or Firm* — Wilson Sonsini Goodrich & Rosati

(57) ABSTRACT

Methods, systems and devices for treating a patient include providing a tissue treatment element constructed and arranged to deliver energy to tissue and treating tissue of the gastrointestinal tract by causing the tissue treatment element to deliver energy to an energy delivery zone. Treatment results in a reduction in the luminal surface area of at least a portion of the gastrointestinal tract. In particular embodiments, the methods, systems and devices are used to treat diabetes.

25 Claims, 9 Drawing Sheets

Related U.S. Application Data

(60) Provisional application No. 61/831,025, filed on Jun. 4, 2013.

(51) Int. Cl.

| A61B 17/32 | (2006.01) |
|---|---|
| A61B 18/02 | (2006.01) |
| A61B 18/04 | (2006.01) |
| A61B 18/22 | (2006.01) |
| A61B 18/00 | (2006.01) |

(52) U.S. Cl.
CPC ......... *A61B 18/042* (2013.01); *A61B 18/1815* (2013.01); *A61B 18/22* (2013.01); *A61B 2018/0022* (2013.01); *A61B 2018/00023* (2013.01); *A61B 2018/00494* (2013.01); *A61B 2018/00577* (2013.01); *A61B 2018/00589* (2013.01); *A61B 2018/00875* (2013.01); *A61B 2018/046* (2013.01)

(58) Field of Classification Search
CPC .... A61B 2018/00875; A61B 2018/046; A61B 17/00234; A61B 17/0218; A61B 18/082; A61B 18/24; A61B 2017/00022; A61B 2017/00199; A61B 2017/00818; A61B 2018/00005
See application file for complete search history.

(56) References Cited

U.S. PATENT DOCUMENTS

| 5,471,982 | A | 12/1995 | Edwards et al. |
|---|---|---|---|
| 5,496,311 | A | 3/1996 | Abele et al. |
| 5,515,100 | A | 5/1996 | Nogo |
| 5,542,928 | A | 8/1996 | Evans et al. |
| 5,549,559 | A | 8/1996 | Eshel |
| 5,575,772 | A | 11/1996 | Lennox |
| 5,704,934 | A | 1/1998 | Neuwirth et al. |
| 5,730,719 | A | 3/1998 | Edwards |
| 5,800,484 | A | 9/1998 | Gough et al. |
| 5,827,269 | A | 10/1998 | Saadat |
| 5,871,525 | A | 2/1999 | Edwards et al. |
| 5,879,347 | A | 3/1999 | Saadat |
| 5,957,962 | A | 9/1999 | Wallsten et al. |
| 5,964,753 | A | 10/1999 | Edwards |
| 6,009,877 | A | 1/2000 | Edwards |
| 6,053,937 | A | 4/2000 | Edwards et al. |
| 6,056,744 | A | 5/2000 | Edwards |
| 6,066,132 | A | 5/2000 | Chen et al. |
| 6,077,257 | A | 6/2000 | Edwards et al. |
| 6,112,123 | A | 8/2000 | Kelleher et al. |
| 6,293,909 | B1 | 9/2001 | Chu et al. |
| 6,325,777 | B1 | 12/2001 | Zadno-Azizi et al. |
| 6,325,798 | B1 | 12/2001 | Edwards et al. |
| 6,338,726 | B1 | 1/2002 | Edwards et al. |
| 6,358,245 | B1 | 3/2002 | Edwards et al. |
| 6,402,744 | B2 | 6/2002 | Edwards et al. |
| 6,405,732 | B1 | 6/2002 | Edwards et al. |
| 6,409,723 | B1 | 6/2002 | Edwards |
| 6,425,887 | B1 | 7/2002 | McGuckin et al. |
| 6,443,947 | B1 | 9/2002 | Marko et al. |
| 6,544,226 | B1 | 4/2003 | Gaiser et al. |
| 6,673,070 | B2 | 1/2004 | Edwards et al. |
| 6,712,814 | B2 | 3/2004 | Edwards et al. |
| 6,802,841 | B2 | 10/2004 | Utley et al. |
| 6,905,496 | B1 | 6/2005 | Ellman et al. |
| 6,962,587 | B2 | 11/2005 | Johnson et al. |
| 6,974,456 | B2 | 12/2005 | Edwards et al. |
| 7,077,841 | B2 | 7/2006 | Gaiser et al. |
| 7,111,627 | B2 | 9/2006 | Stack et al. |
| 7,122,031 | B2 | 10/2006 | Edwards et al. |
| 7,125,407 | B2 | 10/2006 | Edwards et al. |
| 7,156,860 | B2 | 1/2007 | Wallsten |
| 7,165,551 | B2 | 1/2007 | Edwards et al. |
| 7,241,295 | B2 | 7/2007 | Maguire |
| 7,326,207 | B2 | 2/2008 | Edwards |
| 7,371,215 | B2 | 5/2008 | Colliou et al. |
| 7,387,626 | B2 | 6/2008 | Edwards et al. |
| 7,422,587 | B2 | 9/2008 | Bek et al. |
| 7,507,234 | B2 | 3/2009 | Utley et al. |
| 7,507,238 | B2 | 3/2009 | Utley et al. |
| 7,530,979 | B2 | 5/2009 | Ganz et al. |
| 7,556,628 | B2 | 7/2009 | Utley et al. |
| 7,585,296 | B2 | 9/2009 | Edward et al. |
| 7,632,268 | B2 | 12/2009 | Utley et al. |
| 7,632,291 | B2 | 12/2009 | Stephens et al. |
| 7,648,500 | B2 | 1/2010 | Edwards et al. |
| 7,758,623 | B2 | 7/2010 | Dzeng et al. |
| 7,947,038 | B2 | 5/2011 | Edwards |
| 7,959,627 | B2 | 6/2011 | Utley et al. |
| 7,993,336 | B2 | 8/2011 | Jackson et al. |
| 7,997,278 | B2 | 8/2011 | Utley et al. |
| 8,012,149 | B2 | 9/2011 | Jackson et al. |
| 8,066,689 | B2 | 11/2011 | Mitelberg et al. |
| 8,152,803 | B2 | 4/2012 | Edwards et al. |
| 8,177,853 | B2 | 5/2012 | Stack et al. |
| 8,192,426 | B2 | 6/2012 | Stern et al. |
| 8,251,992 | B2 | 8/2012 | Utley et al. |
| 8,273,012 | B2 | 9/2012 | Wallace et al. |
| 8,323,229 | B2 | 12/2012 | Shin et al. |
| 8,364,237 | B2 | 1/2013 | Stone et al. |
| 8,377,055 | B2 | 2/2013 | Jackson et al. |
| 8,641,711 | B2 | 2/2014 | Kelly et al. |
| 8,740,894 | B2 | 6/2014 | Edwards |
| 9,364,283 | B2 | 6/2016 | Utley et al. |
| 9,555,020 | B2 | 1/2017 | Pasricha et al. |
| 9,615,880 | B2 | 4/2017 | Gittard et al. |
| 9,757,535 | B2 | 9/2017 | Rajagopalan et al. |
| 2002/0013581 | A1 | 1/2002 | Edwards et al. |
| 2002/0115992 | A1 | 8/2002 | Utley et al. |
| 2003/0093072 | A1 | 5/2003 | Friedman |
| 2003/0233065 | A1 | 12/2003 | Steward |
| 2004/0082859 | A1 | 4/2004 | Schaer |
| 2004/0087936 | A1 | 5/2004 | Stern et al. |
| 2004/0133256 | A1 | 7/2004 | Callister |
| 2004/0148034 | A1 | 7/2004 | Kagan et al. |
| 2004/0204768 | A1 | 10/2004 | Geitz |
| 2004/0215180 | A1 | 10/2004 | Starkebaum et al. |
| 2004/0215296 | A1 | 10/2004 | Ganz et al. |
| 2004/0220559 | A1 | 11/2004 | Kramer et al. |
| 2005/0165437 | A1 | 7/2005 | Takimoto |
| 2005/0171524 | A1 | 8/2005 | Stern et al. |
| 2005/0203489 | A1 | 9/2005 | Saadat et al. |
| 2005/0222558 | A1 | 10/2005 | Baxter et al. |
| 2005/0251116 | A1 | 11/2005 | Steinke et al. |
| 2005/0273090 | A1 | 12/2005 | Nieman et al. |
| 2006/0118127 | A1 | 6/2006 | Chinn |
| 2006/0135963 | A1 | 6/2006 | Kick et al. |
| 2006/0155261 | A1 | 7/2006 | Bek et al. |
| 2006/0205992 | A1 | 9/2006 | Lubock et al. |
| 2006/0259030 | A1 | 11/2006 | Utley et al. |
| 2006/0293742 | A1 | 12/2006 | Dann et al. |
| 2007/0016262 | A1 | 1/2007 | Gross et al. |
| 2007/0032788 | A1 | 2/2007 | Edwards et al. |
| 2008/0045785 | A1 | 2/2008 | Oyatsu |
| 2008/0107744 | A1 | 5/2008 | Chu |
| 2008/0119788 | A1 | 5/2008 | Winter |
| 2008/0125760 | A1 | 5/2008 | Gilboa |
| 2008/0125803 | A1 | 5/2008 | Sadamasa et al. |
| 2008/0147056 | A1 | 6/2008 | Van Der Weide et al. |
| 2008/0207994 | A1 | 8/2008 | Gonon |
| 2008/0243112 | A1 | 10/2008 | De Neve |
| 2008/0275445 | A1* | 11/2008 | Kelly ................ A61B 18/1492 606/45 |
| 2009/0012512 | A1 | 1/2009 | Utley et al. |
| 2009/0012518 | A1 | 1/2009 | Utley et al. |
| 2009/0018604 | A1 | 1/2009 | Mitelberg et al. |
| 2009/0048593 | A1 | 2/2009 | Ganz et al. |
| 2009/0069805 | A1 | 3/2009 | Fischer et al. |
| 2010/0022891 | A1 | 1/2010 | Zuluaga et al. |
| 2010/0030190 | A1 | 2/2010 | Singh |
| 2010/0114087 | A1 | 5/2010 | Edwards et al. |
| 2010/0114325 | A1 | 5/2010 | Yang et al. |

(56) References Cited

U.S. PATENT DOCUMENTS

| | | |
|---|---|---|
| 2010/0168561 A1 | 7/2010 | Anderson |
| 2010/0168624 A1 | 7/2010 | Sliwa |
| 2010/0204673 A1 | 8/2010 | Miller |
| 2010/0204688 A1 | 8/2010 | Hoey et al. |
| 2010/0217151 A1 | 8/2010 | Gostout et al. |
| 2010/0256775 A1 | 10/2010 | Belhe et al. |
| 2010/0260703 A1 | 10/2010 | Yankelson et al. |
| 2011/0046537 A1 | 2/2011 | Errico et al. |
| 2011/0091564 A1 | 4/2011 | Chu |
| 2011/0106273 A1 | 5/2011 | Belhe et al. |
| 2011/0160648 A1 | 6/2011 | Hoey |
| 2011/0172659 A1 | 7/2011 | Brannan |
| 2011/0319809 A1 | 12/2011 | Smith |
| 2012/0197245 A1 | 8/2012 | Burnett et al. |
| 2012/0271277 A1 | 10/2012 | Fischell et al. |
| 2012/0289952 A1 | 11/2012 | Utley et al. |
| 2013/0071466 A1 | 3/2013 | Chancellor et al. |
| 2013/0178910 A1 | 7/2013 | Azamian et al. |
| 2013/0345670 A1 | 12/2013 | Rajagopalan et al. |
| 2014/0031773 A1 | 1/2014 | Mikkaichi |
| 2014/0074077 A1 | 3/2014 | Lane |
| 2014/0088529 A1 | 3/2014 | Bengtson |
| 2014/0121646 A1 | 5/2014 | Lodin et al. |
| 2014/0135661 A1 | 5/2014 | Garrison et al. |
| 2014/0163664 A1 | 6/2014 | Goldsmith |
| 2014/0187619 A1 | 7/2014 | Pasricha et al. |
| 2014/0255458 A1 | 9/2014 | Li et al. |
| 2014/0324037 A1 | 10/2014 | Hoey et al. |
| 2014/0371736 A1 | 12/2014 | Levin et al. |
| 2015/0045825 A1 | 2/2015 | Caplan et al. |
| 2015/0141987 A1 | 5/2015 | Caplan et al. |
| 2015/0148738 A1 | 5/2015 | Caplan et al. |
| 2015/0359594 A1 | 12/2015 | Ben-Oren et al. |
| 2016/0008050 A1 | 1/2016 | Rajagopalan et al. |
| 2016/0310200 A1 | 10/2016 | Wang |
| 2017/0007324 A1 | 1/2017 | Kadamus et al. |
| 2017/0014596 A1 | 1/2017 | Rajagopalan et al. |
| 2017/0333122 A1 | 11/2017 | Rajagopalan et al. |
| 2018/0193078 A1 | 7/2018 | Rajagopalan et al. |
| 2018/0193590 A1 | 7/2018 | Rajagopalan et al. |
| 2018/0221622 A1 | 8/2018 | Rajagopalan et al. |

FOREIGN PATENT DOCUMENTS

| | | |
|---|---|---|
| CN | 101212932 A | 7/2008 |
| EP | 1698296 A1 | 9/2006 |
| EP | 1886634 A1 | 2/2008 |
| EP | 3071286 A1 | 9/2016 |
| JP | 2002503512 A | 2/2002 |
| JP | 2003520068 A | 7/2003 |
| JP | 2004500184 A | 1/2004 |
| JP | 2006509536 A | 3/2006 |
| JP | 2006136726 A | 6/2006 |
| JP | 2007502690 A | 2/2007 |
| JP | 2008515464 A | 5/2008 |
| JP | 2010142661 A | 7/2010 |
| JP | 2010533036 A | 10/2010 |
| JP | 2011517599 A | 6/2011 |
| JP | 2013543423 A | 12/2013 |
| JP | 2014503256 A | 2/2014 |
| KR | 20080013945 A | 2/2008 |
| WO | WO-9912489 A2 | 3/1999 |
| WO | WO-0207628 A2 | 1/2002 |
| WO | WO-02058577 A1 | 8/2002 |
| WO | WO-02102453 A2 | 12/2002 |
| WO | WO-03033045 A2 | 4/2003 |
| WO | WO-03092609 A2 | 11/2003 |
| WO | WO-2006020370 A2 | 2/2006 |
| WO | WO-2007044244 A2 | 4/2007 |
| WO | WO-2008002654 A2 | 1/2008 |
| WO | WO-2010042461 A1 | 4/2010 |
| WO | WO-2010125570 A1 | 11/2010 |
| WO | WO-2011060301 A1 | 5/2011 |
| WO | WO-2012009486 A2 | 1/2012 |
| WO | WO-2012099974 A2 | 7/2012 |
| WO | WO-2013130655 A1 | 9/2013 |
| WO | WO-2013134541 A2 | 9/2013 |
| WO | WO-2013159066 A1 | 10/2013 |
| WO | WO-2014022436 A1 | 2/2014 |
| WO | WO-2014026055 A1 | 2/2014 |
| WO | WO 2014055997 A1 | 4/2014 |
| WO | WO-2014070136 A1 | 5/2014 |
| WO | WO-2015038973 A1 | 3/2015 |
| WO | WO-2015077571 A1 | 5/2015 |
| WO | WO-2015148541 A1 | 10/2015 |
| WO | WO-2016011269 A1 | 1/2016 |
| WO | WO-2018089773 A1 | 5/2018 |

OTHER PUBLICATIONS

European search report and search opinion dated Nov. 25, 2015 for EP Application. No. 1.3777572.2.

International search report and written opinion dated Feb. 20, 2015 for PCT Application No. US2014/711601.

International search report and: written opinion dated Jun. 21, 2013 for PCT Application No. US2013/028082.

International search report and written opinion dated Jun. 26, 2015 for PCT Application No. US2015/022293.

International search report and written opinion dated Jul. 13, 2012 for PCT Application No. US2012/021739.

International search report and written opinion dated Aug. 8, 2013 for PCT Application No. US2013/037485.

International search report and written opinion dated Oct. 23, 2015 for PCT/US2015/040775.

International search report and written opinion dated Nov. 8, 2013 for PCT Application No. US2013/052786.

International search report and written opinion dated Nov. 11, 2013 for PCT Application No. US2013/054219.

International search report and written opinion dated Dec. 24, 2014 for PCT Application No. US2014/055614.

International search report and written opinion dated Dec. 30, 2013 for PCT Application No. US2013/063753.

International search report dated Dec. 3, 2014 for PCT Application No. US2014/040957.

Miyawaki, et al. Inhibition of gastric inhibitory polypeptide signaling prevents obesity. Nat Med. Jul. 2002;8(7):738-42. Epub. Jun. 17, 2002.

Office action dated Mar. 12, 2015 for U.S. Appl. No. 13/945,138.

Office action dated Aug. 5, 2015 for U.S. Appl. No. 13/945,138.

Office action dated Nov. 30, 2015 for U.S. Appl. No. 13/945,138.

Office action dated Dec. 17, 2015 for U.S. Appl. No. 14/515,324.

Rubino, et al. Potential of surgery for curing type 2 diabetes mellitus. Ann Surg, Nov. 2002;236(5);554-9.

U.S. Appl. No. 61/681,502, filed Aug. 9, 2012.

U.S. Appl. No. 61/603,475, filed Feb. 27, 2012.

U.S. Appl. No. 61/635,810, filed Apr. 19, 2012.

Co-pending U.S. Appl. No. 14/917,243, filed Mar. 7, 2016.

European search report and search opinion dated Mar. 8, 2016 for EP Application No. 13825257.2.

European search report and search opinion dated Mar. 17, 2016 for EP Application No. 13827149.9.

Office action dated Feb. 29, 2016 for U.S. Appl. No. 14/609,334.

Office action dated Mar. 28, 2016 for U.S. Appl. No. 14/673,565.

Chathadi, et al. The role of endoscopy in ampullary and duodenal adenomas. Gastrointest Endosc. Nov. 2015;82(5):773-81. doi: 10.1016/j.gie.2015.06.027. Epub Aug. 7, 2015.

Co-pending U.S. Appl. No. 15/156,585, filed May 17, 2016.

Adams, et al. Theoretical design and evaluation of endoluminal ultrasound applicators for thermal therapy of pancreatic cancer under image guidance. AIP Conference Proceedings 1821, 110002 (2017); doi: http://dx.doi.org/10.1063/1.4977640.

Cherrington, et al. Hydrothermal Duodenal Mucosal Resurfacing: Role in the Treatment of Metabolic Disease. Gastrointest Endosc Clin N Am. Apr. 2017;27(2):299-311. doi: 10.1016/j.giec.2016.12.002.

European Search Report and Search Opinion dated Aug. 7, 2017 for European Patent Application No. EP14864511.2.

(56) References Cited

OTHER PUBLICATIONS

European Search Report and Search Opinion dated Aug. 7, 2017 for European Patent Application No. EP15768945.6.
European search report with written opinion dated Feb. 1, 2018 for EP Application No. 15822378.
European search report with written opinion dated Dec. 2, 2016 for EP Application No. 14807116.
Galvao Neto, et al. Endoscopic Duodenal Mucosal Resurfacing Improves Glycemic and Hepatic Parameters in Patients With Type 2 Diabetes: Data From a First-in-Human Study. Gastroenterology. 829. Apr. 2016, vol. 150, Issue 4, Supplement 1, p. S174. 1 page. DOI: http://dx.doi.org/10.1016/S0016-5085(16)30672-2.
International Search Report and Written Opinion dated Sep. 22, 2016 for International PCT Patent Application No. PCT/US2016/040512.
International search report with written opinion dated Jan. 9, 2018 for PCT/US2017/061074.
Notice of Allowance dated Jul. 7, 2017 for U.S. Appl. No. 15/274,764.
Notice of Allowance dated Sep. 14, 2017 for U.S. Appl. No. 15/274,809.
"Office Action dated Jul. 11, 2018 for U.S. Appl. No. 14/917,243."
"Office Action dated Aug. 9, 2018 for U.S. Appl. No. 14/673,565."
Office action dated Jan. 8, 2018 for U.S. Appl. No. 14/609,334.
Office Action dated Jan. 13, 2017 for U.S. Appl. No. 14/609,332.
Office Action dated Mar. 7, 2017 for U.S. Appl. No. 15/274,764.
Office Action dated Mar. 7, 2017 for U.S. Appl. No. 15/274,809.
Office action dated Mar. 19, 2018 for U.S. Appl. No. 14/470,503.
Office Action dated Mar. 23, 2017 for U.S. Appl. No. 13/945,138.
Office action dated Apr. 4, 2018 for U.S. Appl. No. 15/156,585.
Office Action dated May 31, 2017 for U.S. Appl. No. 15/274,764.
Office Action dated Jun. 21, 2017 for U.S. Appl. No. 14/515,324.
Office Action dated Jun. 21, 2017 for U.S. Appl. No. 14/609,334.
Office Action dated Jun. 30, 2017 for U.S. Appl. No. 14/470,503.
"Office action dated Sep. 7, 2018 for U.S. Appl. No. 14/609,332."
Office Action dated Sep. 23, 2016 for U.S. Appl. No. 14/515,324.
Office Action dated Oct. 7, 2016 for U.S. Appl. No. 13/945,138.
Office Action dated Nov. 2, 2017 for U.S. Appl. No. 15/156,585.
Office Action dated Nov. 15, 2016 for U.S. Appl. No. 14/609,334.
Office action dated Nov. 16, 2017 for U.S. Appl. No. 14/609,332.
Office action dated Nov. 30, 2017 for U.S. Appl. No. 14/673,565.
Office action dated Dec. 18, 2017 for U.S. Appl. No. 14/515,324.
Office action dated Dec. 19, 2017 for U.S. Appl. No. 13/945,138.
Rajagopalan, et al. Endoscopic Duodenal Mucosal Resurfacing for the Treatment of Type 2 Diabetes: 6-Month Interim Analysis From the First-in-Human Proof-of-Concept Study. Diabetes Care Dec. 2016; 39(12): 2254-2261. https://doi.org/10.2337/dc16-0383.
Sarriá, et al. Morphometric study of the layers of the canine small intestine at five sampling sites. Vet J. Jun. 2012;192(3):498-502. doi: 10.1016/j.tvjl.2011.06.041. Epub Nov. 3, 2011.
Tomizawa, et al. Clinical Outcome of Endoscopic Mucosal Resection (EMR) of Sporadic, Non-Ampullary Duodenal Adenoma (SNADA): Predictor Analysis of Safety and Efficacy From a High Volume U.S. Tertiary Referral Center. Gastrointestinal Endoscopy. 377. May 2017, vol. 85, Issue 5, Supplement, p. AB72. DOI: http://dx.doi.org/10.1016/j.gie.2017.03.089.
Van Baar, et al. Single Catheter for Duodenal Mucosal Resurfacing Demonstrates Similar Safety Profile with Improved Procedure Time when Compared to Original Dual Catheter: Multicenter Study of Subjects with Type 2 Diabetes. Gastroenterology. Apr. 2017vol. 152, Issue 5, Supplement 1, p. S825. DOI: http://dx.doi.org/10.1016/S0016-5085(17)32851-2.
"Office action dated Oct. 4, 2018 for U.S. Appl. No. 14/515,324."
"Office action dated Nov. 2, 2018 for U.S. Appl. No. 14/609,334".
"Office action dated Dec. 18, 2018 for U.S. Appl. No. 14/470,503.".

* cited by examiner

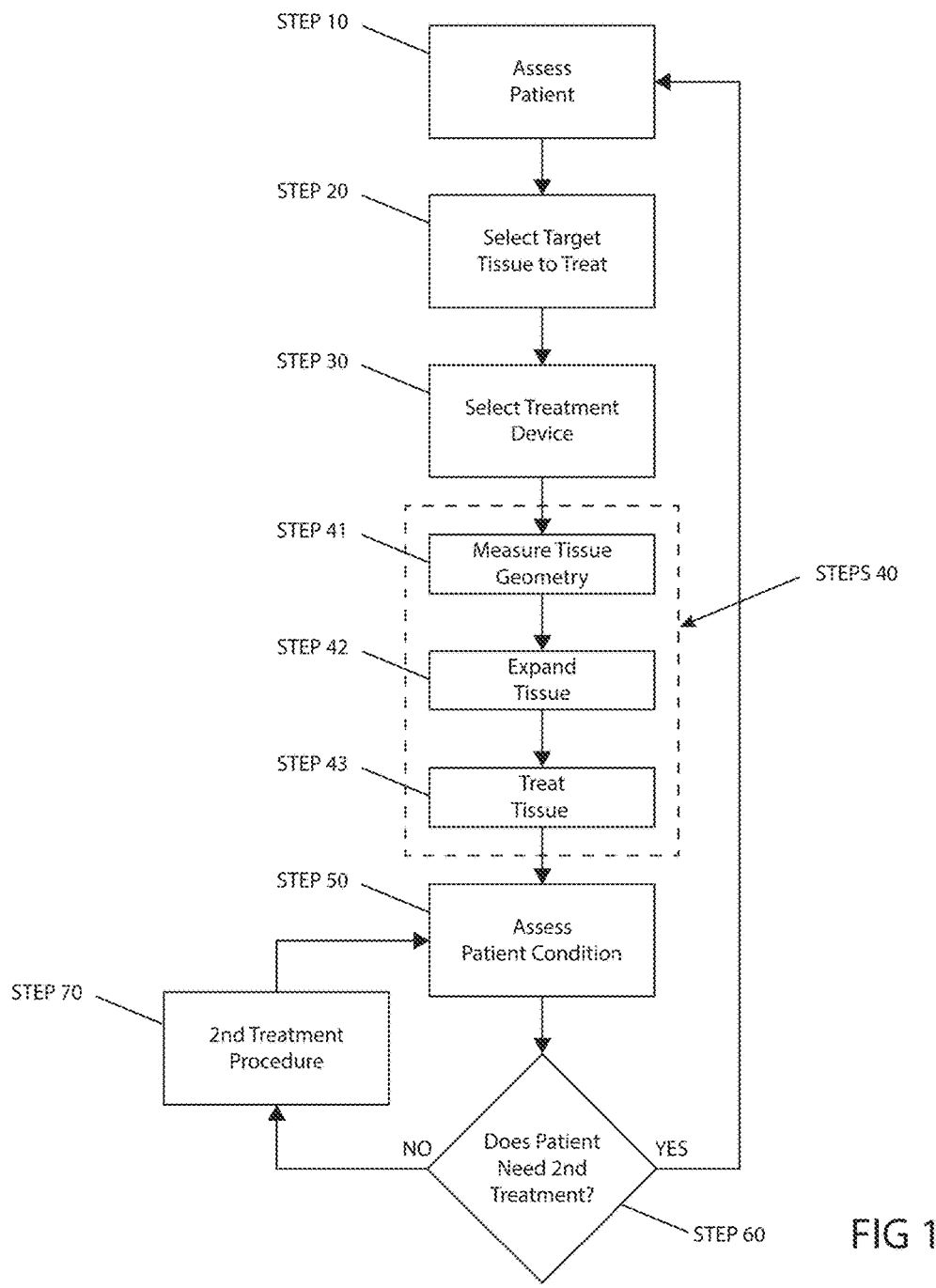

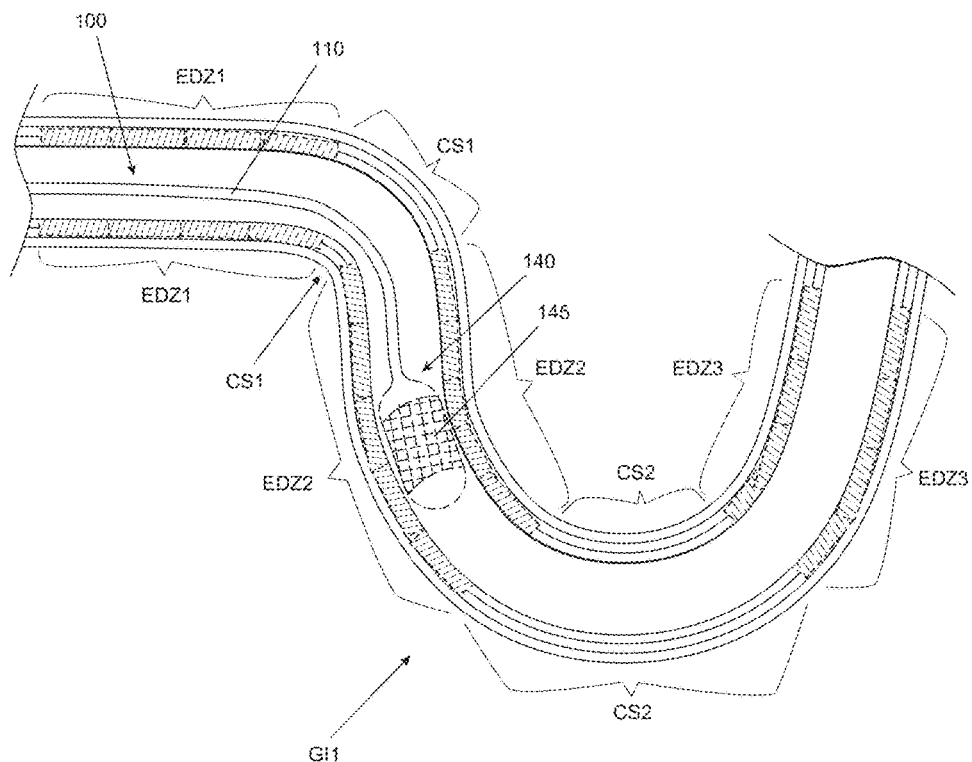

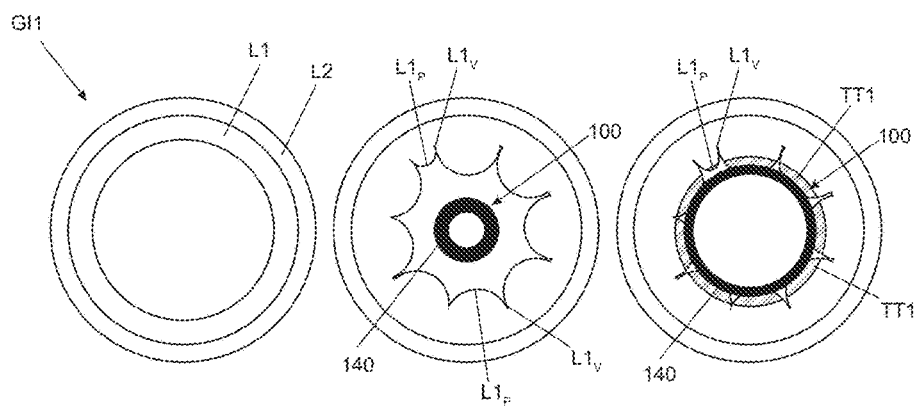
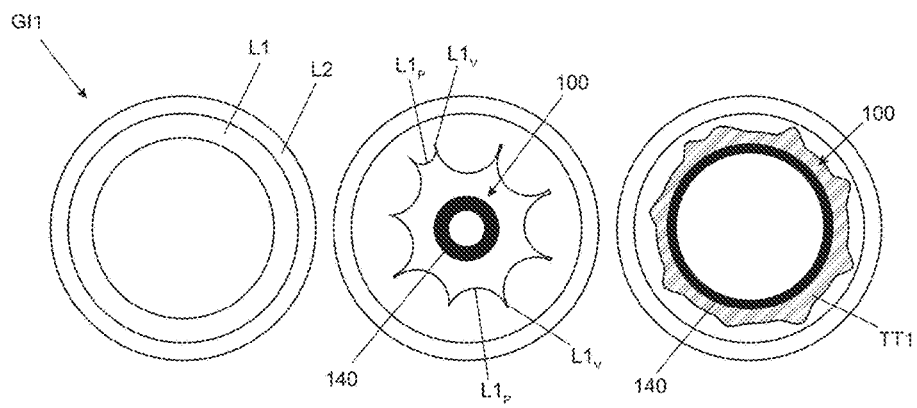

METHODS, SYSTEMS AND DEVICES FOR REDUCING THE LUMINAL SURFACE AREA OF THE GASTROINTESTINAL TRACT

CROSS-REFERENCE TO RELATED APPLICATIONS

The present application is a continuation of International Patent Application No. PCT/US2014/040957, filed Jun. 4, 2014, which claims priority under 35 USC 119(3) to U.S. Provisional Patent Application Ser. No. 61/831,025, entitled "Methods, Systems and Devices for Reducing the Luminal Surface Area of the Gastrointestinal Tract", filed Jun. 4, 2013, which is incorporated herein by reference by its entirety. This application is related to: U.S. patent application Ser. No. 13/945,138, entitled "Devices and Methods for the Treatment of Tissue", filed Jan. 18, 2013; International PCT Application Serial Number PCT/US2013/28082, entitled "Heat Ablation Systems, Devices and Methods for the Treatment of Tissue", filed Feb. 27, 2013; International PCT Application Serial Number PCT/US2013/37485, entitled "Tissue Expansion Devices, Systems and Methods", filed Apr. 19, 2013; International PCT Application Serial Number PCT/US2013/052786, entitled "Electrical Energy Ablation Systems, Devices and Methods for the Treatment of Tissue", filed Jul. 30, 2013; International PCT Application Serial Number PCT/US2013/054219, entitled "Ablation Systems, Devices and Methods for the Treatment of Tissue", filed Aug. 8, 2013; and International PCT Application Serial Number PCT/US2013/063573, entitled "Methods, Systems and Devices for Performing Multiple Treatments on a Patient", filed Oct. 7, 2013; the contents of which are each incorporated herein by reference in their entirety.

TECHNICAL FIELD

The embodiments disclosed herein relate generally to systems, devices and methods for treating tissue, particularly gastrointestinal tissue.

BACKGROUND

A number of systemic diseases are currently treated with medicines that provide amelioration of symptoms or complications of the illnesses but which do not specifically target the pathologic basis of disease. These illnesses are characterized as "chronic diseases" for no reason other than the fact that, for the majority of patients, the diseases are chronically managed rather than acutely treated.

The reasons that chronic diseases are not treated definitively differ based on the specific diseases in question. In some cases, the diseases are not understood well enough as of yet for definitive therapies to have been developed to solve them. In other cases, the definitive therapy, if it does exist, is too unattractive (e.g. high morbidity or mortality, high risk of complications, inaccessible) for the majority of patients to achieve therapeutic relief. In either case, chronic management of the illness burdens the patient with the need for ongoing medical attention and burdens the healthcare provider and system to continue to deliver episodic (and expensive) care of chronic diseases and their complications.

Diabetes is a metabolic disease in which a person develops high blood sugar because the person's body does not produce enough insulin or the cells of the body are incapable of effectively responding to the produced insulin. Primarily, diabetes is of two types: Type 1 and Type 2. Type 1 diabetes results from the body's autoimmune destruction of pancreatic beta cells and, consequently, the body's failure to produce enough insulin. Type 2 diabetes is a complex metabolic derangement related to obesity that causes hyperglycemia through insulin resistance (in which the body's cells fail to properly utilize the produced insulin) and eventually inadequate insulin production to meet the body's needs.

Currently, there are several procedures aimed at treating diabetes based on the above concept. The procedures require major surgery, removal of portions of the gastrointestinal (GI) tract, and/or long-term implants. As with any major surgery, gastric bypass surgery carries a risk of complications.

Devices have been developed to delivery energy to the body. For example, cardiac ablation devices have been designed to delivery ablative energy to coronary tissue. Additionally, urethral resection devices have been designed to burn or cut away portions of a prostate. Each of these technologies has been modified and adapted toward effective usage in the particular portion of the body to be treated as well as the particular disease to be treated.

New inventions that can harness novel physiologic understanding of diseases and deliver therapies that are therapeutically beneficial, accessible to patients, and reduce healthcare costs are needed. Specifically, there is a need to provide a therapeutic treatment of patient diseases and disorders such as diabetes, with a procedure in the GI tract that is simple, and minimally invasive, and has other advantages for patients.

SUMMARY OF THE INVENTION

According to one aspect of the present inventive concepts, a method for treating a patient comprises providing a tissue treatment element constructed and arranged to deliver energy to tissue, and treating target tissue of the patient's gastrointestinal tract by causing the tissue treatment element to deliver energy to an energy delivery zone. The method causes a reduction in the luminal surface area of at least a portion of the gastrointestinal tract.

In some embodiments, the patient is a human being.

In some embodiments, the surface area reduction comprises a reduction in mucosal surface area.

In some embodiments, the surface area reduction is constructed and arranged to reduce absorption and/or secretion of the at least a portion of the gastrointestinal tract.

In some embodiments, the method treats diabetes such as type 2 diabetes. The method can treat one or more of: a patient that has exhibited diabetic physiology for less than 1 year; a patient that has exhibited diabetic physiology for less than 2 years; a patient that has exhibited diabetic physiology for less than 5 years; or a patient that has exhibited diabetic physiology for less than 10 years.

In some embodiments, the patient has exhibited a disease state to be treated for at least 1 year, at least 2 years or at least 5 years.

In some embodiments, the method treats impaired glucose tolerance.

In some embodiments, the patient comprises a patient with an HbA1c level of at least 7.5 or at least 8.

In some embodiments, the method treats a disease or disorder selected from the group consisting of: diabetes; pre-diabetes; impaired glucose tolerance; insulin resistance; and combinations thereof.

In some embodiments, the method treats a disease or disorder selected from the group consisting of: diabetes; pre-diabetes; impaired glucose tolerance; insulin resistance;

obesity or otherwise being overweight; hypercholesterolemia; exercise intolerance; psoriasis; hypertension; hypertriglyceridemia; metabolic syndrome; and combinations thereof.

In some embodiments, the method is constructed and arranged to cause a reduced absorptive and/or secretory capacity in a surface area reduced portion of the gastrointestinal tract, such as when the reduced absorption is a reduced absorption of glucose, cholesterol, a monoglyceride and/or a fatty free acid.

In some embodiments, the method is constructed and arranged to reduce glucose absorption in a surface area reduced portion of the gastrointestinal tract after food intake.

In some embodiments, the method is constructed and arranged to reduce release of gut hormones from a surface area reduced portion of the gastrointestinal tract after food intake, such as to cause reduced release of GIP and/or other proximal gut hormone.

In some embodiments, the surface area reduction results in a physiologic change in a surface area reduced portion of the gastrointestinal tract selected from the group consisting of: reduced absorption of nutrients; reduced secretion of gut hormones; and combinations thereof.

In some embodiments, the method comprises a second patient treatment. The second patient treatment can be performed after treating the target tissue in the first treatment. The second treatment can comprise a controlled diet, such as a low calorie diet. The low calorie diet can comprise one or more of: a diet of less than 1500 calories per day; a diet of less than 1000 calories per day; a minimal fructose content diet; a minimal simple sugar content diet; a minimal fat content diet; and a diet performed during a period a mucosal regrowth. The second treatment can comprise a pharmaceutical treatment comprising a pharmaceutical selected from the group consisting of: an anti-inflammatory agent such as a steroid; an immunomodulator such as Sirolumus or Tacrolimus; Sucralfate; a bismuth compound; an acid inhibitor; a proton-pump inhibitor; a H2-receptor blocker; an antibiotic; an anti-fungal; an appetite suppressant agent; an anti-obesity agent; an anti-cholesterol agent; a diabetes drug; metformin; a GLP-1 analogue; a DPP-IV inhibitor; sulfonulereas; insulin; an insulin analog; and combinations thereof.

In some embodiments, the energy delivery zone and/or the target tissue treated is proportionally related to the longevity of the disease state. In these embodiments, the disease state can be diabetes. The energy delivery zone can comprise less than 50% of the duodenal inner surface area if the patient has exhibited diabetic physiology less than 3 years, such as when a portion of the energy delivery zone receives energy from the tissue treatment element, and the portion receiving energy comprises a percentage of the energy delivery zone selected from the group consisting of: at least 2%; at least 5%; at least 10%; or at least 20%. The energy delivery zone can comprise less than 50% of the duodenal inner surface area if the patient has exhibited diabetic physiology less than 5 years, such as when a portion of the energy delivery zone receives energy from the tissue treatment element, and the portion receiving energy comprises a percentage of the energy delivery zone selected from the group consisting of: at least 2%; at least 5%; at least 10%; or at least 20%. The energy delivery zone can comprise less than 75% of the duodenal inner surface area if the patient has exhibited diabetic physiology less than 7 years, such as when a portion of the energy delivery zone receives energy from the tissue treatment element, and the portion receiving energy comprises a percentage of the energy delivery zone selected from the group consisting of: at least 2%; at least 5%; at least 10%; or at least 20%. The energy delivery zone can comprise less than 75% of the duodenal inner surface area if the patient has exhibited diabetic physiology less than 10 years, such as when a portion of the energy delivery zone receives energy from the tissue treatment element, and the portion receiving energy comprises a percentage of the energy delivery zone selected from the group consisting of: at least 2%; at least 5%; at least 10%; or at least 20%.

In some embodiments, the energy delivery zone and/or the target tissue treated is proportionally related to the severity of the disease state. In these embodiments, the disease state can be diabetes. The energy delivery zone can comprise less than 50% of the duodenal inner surface area if the patient has an HgBA1c level less than 8, such as when a portion of the energy delivery zone receives energy from the tissue treatment element, and the portion receiving energy comprises a percentage of the energy delivery zone selected from the group consisting of: at least 2%; at least 5%; at least 10%; or at least 20%. The energy delivery zone can comprise less than 50% of the duodenal inner surface area if the patient has an HgBA1c level less than 9, such as when a portion of the energy delivery zone receives energy from the tissue treatment element, and the portion receiving energy comprises a percentage of the energy delivery zone selected from the group consisting of: at least 2%; at least 5%; at least 10%; or at least 20%. The energy delivery zone can comprise less than 75% of the duodenal inner surface area if the patient has an HgBA1c level less than 10, such as when a portion of the energy delivery zone receives energy from the tissue treatment element, and the portion receiving energy comprises a percentage of the energy delivery zone selected from the group consisting of: at least 2%; at least 5%; at least 10%; or at least 20%. The energy delivery zone can comprise less than 75% of the duodenal inner surface area if the patient has an HgBA1c level less than 12, such as when a portion of the energy delivery zone receives energy from the tissue treatment element, and the portion receiving energy comprises a percentage of the energy delivery zone selected from the group consisting of: at least 2%; at least 5%; at least 10%; or at least 20%.

In some embodiments, the energy delivery zone and/or the target tissue to be treated is based on a patient characteristic selected from the group consisting of: duration of diabetes; HbA1c; area under the curve of a glucose tolerance test; area under the curve of a mixed meal tolerance test; C-peptide level; GIP level; GLP-1 level; age; BMI; and combinations thereof.

In some embodiments, the energy delivery zone and/or the target tissue to be treated is based on a target diabetes endpoint result selected from the group consisting of: target HbA1c level; target BMI; target area under the curve of glucose tolerance test; target cholesterol level; target triglyceride level; and combinations thereof.

In some embodiments, the energy delivery zone comprises an anatomical location selected from the group consisting of: inner surface portion of stomach; full circumferential inner surface of an axial segment of duodenum; partial circumferential inner surface of an axial segment of duodenum; full circumferential inner surface of an axial segment of jejunum; partial circumferential inner surface of an axial segment of jejunum; and combinations thereof.

In some embodiments, the energy delivery zone comprises an inner surface of at least one axial segment of the duodenum. The energy delivery zone can comprise an inner surface of multiple axial segments of the duodenum and/or the jejunum. The energy delivery zone can comprise a relatively full circumferential segment of duodenal tissue. The at least one axial segment can comprise a partial circumferential segment of duodenal tissue, such as when the partial circumferential segment comprises a circumferential segment between 45° and 350°. The target tissue can comprise duodenal mucosal tissue. The target tissue can comprise tissue selected from the group consisting of: duodenal mucosal tissue; jejunal mucosal tissue; ileal mucosal tissue; gastric mucosal tissue; and combinations thereof. The at least one axial segment can comprise a proximal end and a distal end. The proximal end can be located distal to but within 5 cm of the ampulla of Vater, or within 2 cm of the ampulla of Vater. The proximal end can be located distal to but within 15 cm of the pylorus, such as within 10 cm of the pylorus. The proximal end can be located distal to the duodenal bulb. The proximal end can be located proximate the most proximal location of the duodenum that includes plicae circulares. The proximal end can be located within 5 cm of the ampulla of Vater and the distal end can be located proximal to the ligament of Treitz. The distal end can be located at least 3 cm from the proximal end, such as at least 5 cm, at least 10 cm or at least 50 cm from the proximal end. The multiple axial segments can comprise multiple relatively linear axial tissue segments, such as multiple relatively linear full circumferential axial tissue segments.

In some embodiments, at least one axial segment of the duodenum is not treated by the tissue treatment element. The at least one non-treated axial segment can comprise a segment of the duodenum absent of plicae circulares. The at least one non-treated axial segment can comprise a segment of the duodenum containing the ampulla of Vater. The at least one non-treated axial segment can comprise a curved segment of the duodenum with an approximate average radius of curvature less than 5 cm or less than 3 cm over a 75 degree arc, such as when the tissue treatment element comprises a length with a maximum value of: 30 mm; 25 mm; 20 mm; or 15 mm.

In some embodiments, the target tissue comprises one or more portions of a tissue layer selected from the group consisting of: mucosa; mucosa through superficial submucosa; mucosa through mid-submucosa; mucosa through deep-submucosa; and combinations thereof.

In some embodiments, the target tissue and/or the energy delivery zone comprises multiple tissue segments of the gastrointestinal tract. The multiple tissue segments can be treated sequentially, such as with sequential treatments performed within a twenty-four hour period or within a six month period. The multiple tissue segments can be treated simultaneously. The multiple tissue segments can comprise between 2 and 50 segments. At least two of the multiple tissue segments can comprise full circumferential tissue segments. At least two of the multiple tissue segments can comprise overlapping boundaries, such as when the energy delivery zone comprises a first zone portion and a second zone portion, and the first zone portion and the second zone portion comprise overlapping boundaries. At least two of the multiple tissue segments can comprise similar boundaries, such as when the energy delivery zone comprises a first zone portion and a second zone portion, and the first zone portion and the second zone portion comprise similar boundary segments. The multiple tissue segments can be axially separated by less than or equal to 1 cm or less than or equal to 0.5 cm. The method can further comprise performing a tissue expansion procedure to an axial segment of tissue, such as when the multiple tissue segments comprise a set of partial circumferential portions expanded during the tissue expansion procedure. A first tissue segment receiving energy can be separated from a second tissue segment receiving energy by a portion of tissue not receiving energy. A first partial circumferential expanded portion can be separated from a second partial circumferential expanded portion by a less expanded third partial circumferential expanded portion, where the target tissue treated comprises a greater thickness at the first partial circumferential portion and the second partial circumferential portion than the third partial circumferential portion. The multiple tissue segments can each comprise a length less than 20 cm, or less than 15 cm. The multiple tissue segments can comprise a cumulative length less than 100 cm, or less than 50 cm.

In some embodiments, the method further comprises a step selected from the group consisting of: measuring tissue geometry; measuring target tissue geometry; expanding tissue; expanding target tissue; measuring apposition of a tissue treatment element; and combinations thereof.

In some embodiments, the method further comprises measuring target tissue geometry and expanding target tissue.

In some embodiments, the method further comprises measuring the diameter of tubular tissue with a sizing element.

In some embodiments, the method further comprises modifying the diameter of tubular tissue to modify energy delivery by the tissue treatment element, such as when the modification of energy delivery comprises initiating energy delivery; stopping energy delivery; increasing energy delivery and/or decreasing energy delivery.

In some embodiments, the method further comprises measuring the apposition of the tissue treatment element, such as when the method yet further comprises measuring target tissue geometry, and the measuring of the apposition of the tissue treatment element is based on the measured target tissue geometry.

In some embodiments, the method further comprises measuring the impedance between two or more electrodes, and using the measured impedance to measure tissue diameter and/or apposition of the tissue treatment element.

In some embodiments, the target tissue treatment is based on a controlled system parameter, such as when the controlled system parameter comprises a parameter selected from the group consisting of: a priming procedure parameter such as priming temperature or priming duration; target tissue treatment parameter such as target tissue temperature or target tissue treatment duration; fluid flow rate such as treatment fluid flow rate; a pressure parameter such as a tissue treatment element pressure maintained during treatment of target tissue; a tissue treatment element diameter such as a tissue treatment element diameter maintained during treatment of target tissue; and combinations thereof.

In some embodiments, the method further comprises controlling at least one tissue treatment element parameter during the tissue treatment. The tissue treatment element controlled parameter can comprise a parameter selected from the group consisting of: thermal dose delivered; priming temperature; tissue treatment temperature; fluid flow rate; pumping pressure; vacuum pressure; tissue treatment time; and combinations thereof. The tissue treatment element can comprise a balloon and the tissue treatment element variable being controlled can comprise the balloon diameter. The method can further comprise selecting a balloon diameter prior to target tissue treatment.

In some embodiments, the target tissue is treated with an ablative energy treatment, such as an ablative energy treatment selected from the group consisting of: delivery of thermal energy from a balloon filled with fluid at an ablative temperature; radiofrequency (RF) energy ablation; delivery of an ablative fluid directly to tissue; cryoablation; delivery of laser energy; delivery of sound energy such as subsonic sound energy or ultrasonic sound energy; plasma energy delivery; argon plasma coagulation; microwave energy delivery; delivery of non-laser light energy; and combinations thereof.

In some embodiments, the target tissue is treated with a non-ablative energy treatment, such as when the non-ablative treatment comprises a treatment selected from the group consisting of: mechanical removal of mucosal tissue; chemical, sclerosant or pharmaceutical injection into the submucosa; radioactive seed deposition; chemical spray such as an acid spray; pharmacologic administration such as drug delivery via an agent-eluting balloon; and combinations thereof.

In some embodiments, the tissue treatment element is constructed and arranged to resect tissue. The tissue treatment element can be constructed and arranged to resect tissue selected from the group consisting of: plicae tissue; mucosal tissue; submucosal tissue; and combinations thereof. The tissue treatment element can be constructed and arranged to resect the plicae, such as a tissue treatment element constructed and arranged to resect peaks of the plicae including a majority of the proximate mucosal tissue.

In some embodiments, the target tissue is treated with multiple tissue treatment steps. The multiple tissue treatment steps can comprise multiple sequential deliveries of energy to tissue. The multiple tissue treatment steps can comprise multiple sequential deliveries of ablative fluid to tissue. The multiple tissue treatment steps can comprise multiple sequential abrasions of tissue. The method can further comprise expanding one or more layers of tissue. The method can further comprise performing two or more expansions of one or more layers of tissue.

In some embodiments, the target tissue comprises multiple tissue segments with an inward facing surface, and the energy delivery zone comprises between 50 and 3000 target tissue inward facing surfaces per square centimeter of tissue. The energy delivery zone can comprise approximately 500 target tissue segment inward facing surfaces per square centimeter of tissue. The target tissue segment inward facing surfaces can each comprise an equivalent diameter between approximately 20 and 200 microns. The target tissue segment inward facing surfaces can each comprise a surface area with a major axis less than or equal to 100 microns. The energy can be delivered to the target tissue segment inward facing surfaces sequentially, such as when the energy is delivered with a scanning tissue treatment element, such as a scanning tissue treatment element constructed and arranged to rotate and translate, and the translation is between 0.5 cm and 3 cm in length. Alternatively or additionally, the energy can be delivered to multiple target tissue segment inward facing surfaces simultaneously. The tissue treatment element can comprise an element constructed and arranged to deliver multiple rays of ablative light energy, such as when the tissue treatment element comprises a light delivery element and a shroud, and the shroud comprises an opaque substrate with multiple transmissive portions, such as when the shroud comprises an expandable element. Non-target tissue can be positioned between each of the target tissue segment inward facing surfaces. The ratio of the surface area of the target tissue segment inward facing surfaces to the surface area of the non-target tissue positioned between the inward facing surfaces can be between 0.1% and 90%. The ratio of the surface area of the target tissue segment inward facing surfaces to the surface area of the non-target tissue positioned between the inward facing surfaces can be less than 50%, less than 20%, less than 10%, less than 5%, less than 2% or less than 1%. A fractional energy delivery can be delivered to an axial segment of gastrointestinal tissue in multiple passes. The target tissue segment inward facing surfaces can each comprise relatively elliptical cross sections, such as relatively circular cross sections. The target tissue segment inward facing surfaces can be treated at a temperature at or above 60° C., such as a temperature at or above 100° C., or at a temperature between 60° C. and 80° C. The target tissue segment inward facing surfaces can be vaporized. The target tissue segment inward facing surfaces can receive an energy type selected from the group consisting of: RF; ultrasound; laser light; non-laser light such as non-laser light from an LED; chemical; and combinations thereof. The tissue treatment element can deliver light energy from a laser. The light energy can be delivered through at least one fiber, such as through a coherent or non-coherent bundle of fibers. The light energy can be delivered to a balloon positioned in the gastrointestinal tract. The balloon can surround a volume of light-scattering material, such as light-scattering material comprising material selected from the group consisting of: reflective polystyrene particles; aluminum flakes; reflective microspheres; and combinations thereof. The balloon can comprise multiple apertures, such as an array of apertures in a symmetric or non-symmetric pattern, each aperture relatively transparent to the treatment element light energy being delivered. The laser can comprise a laser selected from the group consisting of: $CO_2$; Erbium; fiber laser; solid state crystal laser such as a Ho:YAG laser; semiconductor laser; and combinations thereof. The laser can deliver light with a wavelength selected from the group consisting of: 2.0 to 2.2 micron; 1.8 to 2.0 micron; 1.24 to 1.64 micron; and combinations thereof. The laser can deliver light with a wavelength of 1.9 micron wavelength and/or 2.1 micron wavelength. The light energy can be distributed by an array of lenses, such as an array comprising two or more lenses selected from the group consisting of: holographic; fresnel; and combinations thereof. The tissue treatment element can comprise an energy distribution element, such as an energy distribution element comprising an element selected from the group consisting of: rotating element such as a rotating mirror; prism; diffractive optic; and combinations thereof. The energy delivery zone can comprise an area between 1.0 $cm^2$ and 5.0 $cm^2$. The method can further comprise expanding one or more layers of tissue. The one or more layers of tissue can be expanded by injection of a non-energy absorbing material into tissue. The one or more layers of tissue can be expanded by injection of an energy absorbing material into tissue, such as water or saline. The tissue treatment element can comprise multiple electrodes constructed and arranged to deliver radiofrequency energy. The multiple electrodes can comprise multiple conductive dots positioned on an expandable balloon. The multiple electrodes can be constructed and arranged to deliver monopolar and/or bipolar radiofrequency energy. The multiple electrodes can comprise an array of electrodes positioned on an expandable element.

In some embodiments, the surface area reduction occurs at least one day after the target tissue treatment.

In some embodiments, the target tissue treatment causes a reduction in a gastrointestinal tissue characteristic selected from the group consisting of: average height of mucosal folds; surface area of mucosal folds; number of mucosal folds; and combinations thereof.

In some embodiments, the tissue treatment element is constructed and arranged to reshape mucosal tissue. The tissue treatment element can be constructed and arranged to flatten mucosal tissue. The tissue treatment element can be constructed and arranged to cause mucosal tissue to reshape at least 7 days after the tissue treatment is performed. The tissue treatment element can be constructed and arranged to cause mucosal tissue to reshape within 1 day of tissue treatment, such as when the tissue treatment element is constructed and arranged to deliver light energy and/or RF energy.

In some embodiments, the target tissue treatment causes a reduction in average villi length.

In some embodiments, the target tissue treatment causes a reduction in the quantity of villi.

In some embodiments, the tissue treatment element is constructed and arranged to reshape submucosal tissue. The reshaped submucosal tissue can cause a healing response that results in a reduced amount of mucosal tissue. The reshaped submucosal tissue can comprise flattened submucosal tissue. The reshaped submucosal tissue can comprise submucosal tissue with increased uniformity of thickness. The reshaped submucosal tissue comprises submucosal tissue with increased averaged minimum thickness. The reshaped submucosal tissue comprises a reduced volume of submucosal tissue. The tissue treatment element can be constructed and arranged to deliver controlled thermal heating of the submucosal tissue, such as when the controlled thermal heating causes collagen of the submucosal tissue to shrink and/or become denatured. The tissue treatment element can be constructed and arranged to cause submucosal tissue to reshape at least 7 days after the target tissue treatment is performed.

In some embodiments, the tissue treatment element is constructed and arranged to reduce the volume of submucosal tissue.

In some embodiments, the tissue treatment element is constructed and arranged to reduce the amount of submucosal tissue on which mucosal tissue grows.

In some embodiments, the target tissue treatment results in a smoother tissue surface in the at least a portion of the gastrointestinal tract.

In some embodiments, the target tissue treatment causes a reduction in the quantity of plicae circulares in the at least a portion of the gastrointestinal tract.

In some embodiments, the target tissue treatment causes a reduction in surface area of absorptive tissue in the at least a portion of the gastrointestinal tract.

In some embodiments, the target tissue treatment treats stem cells. The treated stem cells can comprise mucosal stem cells and/or epithelial stem cells. The target tissue treatment can remove and/or ablate stem cells.

In some embodiments, the target tissue treatment causes a reduction in the number of enteroendocrine cells in the at least a portion of the gastrointestinal tract.

In some embodiments, the target tissue treatment causes a reduction in the number of absorptive cells in the at least a portion of the gastrointestinal tract.

In some embodiments, the surface area reduction occurs at least 7 days after the target tissue treatment is performed. The surface area reduction can further occur within 7 days of the target tissue treatment. The surface area of the at least a portion of the gastrointestinal tract can be reduced at least 3 weeks after the target tissue treatment is performed, such as when the surface area of the at least a portion of the gastrointestinal tract is reduced at least 6 weeks after the target tissue treatment is performed.

In some embodiments, the method provides a therapeutic benefit for at least 6 weeks, at least 6 months or at least 2 years. The method can be repeated after a duration of time of at least 6 weeks to reduce the surface area of the gastrointestinal tract.

In some embodiments, the surface area reduced comprises the surface area of the duodenum and/or the jejunum. The surface area of the duodenum and/or the jejunum can be reduced at least 5%, at least 10%, at least 20%, at least 50%, or at least 90%.

In some embodiments, the method further comprises selecting one tissue treatment element of a kit of tissue treatment elements prior to treating the target tissue.

In some embodiments, the method further comprises selecting and/or controlling the tissue treatment element size. The selecting or controlling the tissue treatment element size can comprise selecting a tissue treatment element between 10 mm and 40 mm in diameter and/or controlling a tissue treatment element to a diameter between 10 mm and 40 mm. The selecting or controlling the tissue treatment element size can comprise selecting a tissue treatment element between 15 mm and 32 mm in diameter and/or controlling a tissue treatment element to a diameter between 15 mm and 32 mm.

In some embodiments, the method further comprises deflecting the tissue treatment element prior to treating the target tissue.

In some embodiments, the method further comprises rotating the tissue treatment element, such as when the tissue treatment element is rotated prior to and/or during target tissue treatment by the tissue treatment element.

In some embodiments, the tissue treatment element comprises a radially expandable element. The radially expandable element can be constructed and arranged to expand to a diameter between 15 mm and 32 mm, to as to expand to a diameter between 19.0 mm and 27.5 mm. The radially expandable element can comprise an element selected from the group consisting of: balloon; expandable cage; radially deployable arm; and combinations thereof.

In some embodiments, the tissue treatment element is constructed and arranged to ablate tissue.

In some embodiments, the tissue treatment element is constructed and arranged to vaporize tissue.

In some embodiments, tissue treatment element is constructed and arranged to cause coagulation necrosis.

In some embodiments, the tissue treatment element comprises an energy delivery element. The tissue treatment element can comprise a balloon constructed and arranged to receive a hot fluid. The hot fluid can be initially provided to the balloon at a temperature greater than or equal to 90° C., and during the course of treating the target tissue, the temperature allowed to decrease, such as to a temperature greater than 70° C. The balloon can be constructed and arranged to receive a fixed volume bolus of fluid. The balloon can be constructed and arranged to receive a recirculating fluid. A cooling fluid can be delivered to the balloon, such as to cool target tissue and/or tissue proximate target tissue. The energy delivery element can comprise an RF energy delivery element, such as when the tissue treatment element comprises an expandable element. The energy delivery element can comprise an element selected from the group consisting of: laser; RF; ultrasound; and combinations thereof.

In some embodiments, the tissue treatment element comprises a tissue cutting element. The tissue treatment element can be constructed and arranged to cut tissue during advancement and/or retraction of the tissue cutting element. Alternatively or additionally, the tissue treatment element can comprise a tissue grasping element. The target tissue treatment can comprise grasping tissue and subsequently cutting tissue.

In some embodiments, the tissue treatment element is positioned on the distal portion of an elongate shaft. The elongate shaft can comprise a distal end with a bulbous element positioned on the distal end. The bulbous element can comprise a diameter of less than 6 mm or less than 4 mm. The bulbous element can comprise a diameter of at least 8 mm. The bulbous element can be constructed and arranged to smoothly traverse plicae. The method can further comprise placing an endoscope into the gastrointestinal tract. The method can further comprise placing the elongate shaft through the endoscope and/or alongside the endoscope. The elongate shaft can be constructed and arranged to be advanced over a guidewire.

In some embodiments, the method further comprises applying an algorithm to determine a treatment parameter. The algorithm can be constructed and arranged to determine an energy delivery zone parameter. The energy delivery zone parameter can comprise a parameter selected from the group consisting of: anatomical location of an energy delivery zone; size (e.g. surface area) of energy delivery zone; percentage of an energy delivery zone to receive energy; type of energy to be delivered to an energy delivery zone; amount of energy to be delivered to an energy delivery zone; and combinations thereof. The algorithm can be constructed and arranged to define the completion status of the clinical procedure. The algorithm can employ patient clinical data and/or patient demographic data.

In some embodiments, the method further comprises identifying the ampulla of Vater. The tissue treatment element can treat target tissue distal to but in close proximity to the ampulla of Vater. The tissue treatment element can treat target tissue proximal to but in close proximity to the ampulla of Vater.

In some embodiments, the method further comprises expanding one or more tissue layers with a tissue expansion element. The expansion of one or more layers of tissue can be performed prior to the target tissue treatment. The at least one tissue layer can comprise a layer of submucosal tissue. The expansion of one or more layers of tissue can be constructed and arranged to flatten plicae circulares tissue. The tissue expansion element can comprise a fluid delivery element constructed and arranged to deliver fluid into the one or more tissue layer to be expanded, such as when the fluid delivery element comprises an element selected from the group consisting of: needle; water jet; iontophoretic fluid delivery element; and combinations thereof. The fluid delivery assembly can deliver a bolus of fluid to one or more tissue sites to expand the one or more layers of tissue. The bolus of fluid can comprise a bolus of at least 1 ml, or a bolus of fluid between 2 ml and 5 ml. The tissue expansion element can be constructed and arranged to deliver fluid to multiple tissue injection sites. The tissue expansion element can be constructed and arranged to deliver fluid to three circumferential tissue injection sites along a single axial location of tubular tissue. A first tissue injection site can be approximately 1 cm from a second tissue injection site. A first tissue injection site can be between 0.5 cm and 5.0 cm from a second tissue injection site. A first tissue injection site can be between 1.0 cm and 3.0 cm from a second injection tissue site. A first tissue injection site can be between 1.0 cm and 2.0 cm from a second tissue injection site. The multiple tissue injection sites can be axially spaced and/or radially spaced locations. The multiple tissue injection sites can be located in tubular tissue, and the axial spacing and/or radial spacing is based on the diameter of the tubular tissue. The tissue expansion element can comprise a vacuum port constructed and arranged to apply a vacuum to tissue. The material injected to expand tissue can comprise a material selected from the group consisting of: water; saline; gel such as a protein hydrogel; and combinations thereof. The tissue expansion element can be constructed and arranged to expand one or more layers of gastrointestinal tissue. The one or more layers of tissue to be expanded can comprise one or more duodenal tissue layers. The one or more layers of tissue to be expanded can comprise one or more jejunal tissue layers. The one or more layers of tissue to be expanded can comprise a submucosal tissue layer. The target tissue treatment can be performed at least 1 minute after the expansion of the one or more layers of tissue, or at least 5 minutes after the expansion of the one or more layers of tissue. The tissue treatment can be performed less than 20 minutes after the expansion of the one or more layers of tissue. The one or more layers of expanded tissue can comprise an inner layer of an axial segment of the duodenum and/or jejunum, while the energy delivery zone comprises multiple, discontinuous partial circumferential portions of the axial segment. In some embodiments, energy is not delivered to at least one partial circumferential tissue portion between two of the treated portions of the axial segment.

In some embodiments, the method further comprises visualizing tissue with a visualization element. The target tissue can be treated based on the tissue visualization. The visualization element can comprise a visible light camera.

In some embodiments, the method further comprises protecting tissue with a tissue protection element. The protected tissue can comprise the ampulla of Vater. The tissue protection element can be deployed before a segment of target tissue is treated. The tissue protection element can be deployed before any target tissue is treated. The tissue protection element can be removed during the treatment of the target tissue. The tissue protection element can be constructed and arranged to be evacuated by the patient's gastrointestinal system.

In some embodiments, the method further comprises protecting tissue with a thermal barrier and/or a thermal spacer.

In some embodiments, the tissue treatment element is advanced through a body lumen over a guidewire.

In some embodiments, the tissue treatment element is advanced through a working channel of an endoscope.

According to another aspect of the present inventive concepts, a system for treating a patient comprises an elongate shaft with a distal portion and a tissue treatment element positioned on the elongate shaft. The tissue treatment element is constructed and arranged to deliver energy to target tissue positioned in one or more energy delivery zones. The system is constructed and arranged to reduce the luminal surface area of at least a portion of the gastrointestinal tract.

In some embodiments, the surface area reduction comprises a reduction in mucosal surface area.

In some embodiments, the surface area reduction is constructed and arranged to reduce absorption and/or secretion of the at least a portion of the gastrointestinal tract.

In some embodiments, the system is constructed and arranged to treat diabetes.

In some embodiments, the system is constructed and arranged to avoid damage to non-target tissue, such as non-target tissue comprising the ampulla of Vater.

In some embodiments, at least one energy delivery zone comprises an inner surface of an axial segment of the duodenum. The at least one energy delivery zone can comprise multiple energy delivery zones each comprising an inner surface of an axial segment positioned in the duodenum and/or the jejunum. The at least one energy delivery zone can comprise a relatively full circumferential segment of duodenal tissue. The at least one energy delivery zone can comprise a partial circumferential segment of duodenal tissue, such as a partial circumferential segment comprising a circumferential segment between 45° and 350°. The target tissue can comprise duodenal mucosal tissue. The target tissue can comprise tissue selected from the group consisting of: duodenal mucosal tissue; jejunal mucosal tissue; ileal mucosal tissue; gastric mucosal tissue; and combinations thereof.

In some embodiments, the target tissue and/or the energy delivery zone comprises multiple tissue segments of the gastrointestinal tract. The multiple tissue segments can comprise between 2 and 50 segments. At least two of the multiple tissue segments can comprise full circumferential tissue segments. At least two of the multiple tissue segments can comprise overlapping boundaries, such as when the energy delivery zone comprises a first zone portion and a second zone portion, and the first zone portion and the second zone portion comprise overlapping boundaries. At least two of the multiple tissue segments can comprise similar boundaries, such as when the energy delivery zone comprises a first zone portion and a second zone portion, and the first zone portion and the second zone portion comprise similar boundary segments. The multiple tissue segments can be axially separated by less than or equal to 1 cm, or less than or equal to 0.5 cm. The system can be further constructed and arranged to perform a tissue expansion procedure to an axial segment of tissue, and the multiple tissue segments comprise a set of partial circumferential portions expanded during the tissue expansion procedure. A first tissue segment receiving energy can be separated from a second tissue segment receiving energy by a portion of tissue not receiving energy. A first partial circumferential expanded portion can be separated from a second partial circumferential expanded portion by a less expanded third partial circumferential expanded portion, and the treated target tissue can comprise a greater thickness at the first partial circumferential portion and the second partial circumferential portion than the third partial circumferential portion. The multiple tissue segments can each comprise a length less than 20 cm, such as a length less than 15 cm. The multiple tissue segments can comprise a cumulative length less than 100 cm, such as a cumulative length less than 50 cm.

In some embodiments, the tissue treatment element is constructed and arranged to deliver energy selected from the group consisting of: RF energy; microwave energy; laser energy; sound energy such as subsonic sound energy or ultrasound energy; chemical energy; thermal energy such as heat energy or cryogenic energy; mechanical energy; energy configured to cut tissue; energy configured to resect tissue; and combinations thereof.

In some embodiments, the tissue treatment element is constructed and arranged to perform an ablative treatment of target tissue, such as when the ablative treatment comprises a treatment selected from the group consisting of: delivery of thermal energy from a balloon filled with fluid at an ablative temperature; RF energy ablation; delivery of an ablative fluid directly to tissue; cryoablation; delivery of laser energy; delivery of sound energy such as subsonic sound energy or ultrasonic sound energy; plasma energy delivery; argon plasma coagulation; microwave energy delivery; delivery of non-laser light energy; and combinations thereof.

In some embodiments, the tissue treatment element is constructed and arranged to perform a non-ablative treatment of target tissue, such as when the non-ablative treatment comprises a treatment selected from the group consisting of: mechanical removal of mucosal tissue; sclerosant injection into the submucosa; radioactive seed deposition; chemical spray such as an acid spray; pharmacologic administration such as drug delivery via an agent-eluting balloon; and combinations thereof.

In some embodiments, the tissue treatment element is constructed and arranged to resect tissue. The tissue treatment element can be constructed and arranged to resect tissue selected from the group consisting of: plicae tissue; mucosal tissue; submucosal tissue; and combinations thereof. The tissue treatment element can be constructed and arranged to resect plicae.

In some embodiments, the system is constructed and arranged to treat target tissue with multiple tissue treatment steps. The multiple tissue treatment steps can comprise multiple sequential deliveries of energy to tissue. The multiple tissue treatment steps can comprise multiple sequential deliveries of ablative fluid to tissue. The multiple tissue treatment steps can comprise multiple sequential abrasions of tissue.

In some embodiments, the system is constructed and arranged to treat target tissue comprising multiple tissue segments with an inward facing surface, such as when the energy delivery zone comprises between 50 and 3000 target tissue inward facing surfaces per square centimeter of tissue. The energy delivery zone can comprise approximately 500 target tissue segment inward facing surfaces per square centimeter of tissue. The target tissue segment inward facing surfaces can each comprise an equivalent diameter between approximately 20 and 200 microns. The target tissue segment inward facing surfaces can each comprise a surface area with a major axis less than or equal to 100 microns. The tissue treatment element can be constructed and arranged to deliver energy to the target tissue segment inward facing surfaces sequentially. Sequential energy delivery can be performed when the tissue treatment element comprises a scanning tissue treatment element, such as when the scanning tissue treatment element is constructed and arranged to rotate and translate, such as a translation between 0.5 cm and 3 cm in length. Alternatively or additionally, the tissue treatment element can be constructed and arranged to deliver energy to multiple target tissue segment inward facing surfaces simultaneously. The tissue treatment element can comprise an element constructed and arranged to deliver multiple rays of ablative light energy, such as when the tissue treatment element comprises a light delivery element and a shroud, and the shroud comprises an opaque substrate with multiple transmissive portions (e.g. apertures). The shroud can comprise an expandable element, such as a balloon with one or more apertures. The system can be constructed and arranged to avoid damage to non-target tissue positioned between each of the target tissue segment inward facing surfaces. The ratio of the surface area of the target tissue segment inward facing surfaces to the surface area of the non-target tissue positioned between the inward facing surfaces (i.e. ratio of treated to non-treated surface areas) can be between 0.1% and 90%, such as a ratio of less than 50%, less than 20%, less than 10%, less than 5%, less than 2% or less than 1%. The system can be constructed and arranged to perform a low-ratio or "fractional" energy delivery that is delivered to an axial segment of gastrointestinal tissue in multiple passes. The tissue treatment element can be constructed and arranged to treat target tissue segment inward facing surfaces each comprising relatively elliptical cross sections, such as relatively circular cross sections. The tissue treatment element can be constructed and arranged to treat target tissue segment inward facing surfaces at a temperature at or above 60° C., such as at a temperature above 100° C. or at temperature between 60° C. and 80° C. The tissue treatment element can be constructed and arranged to vaporize the target tissue segment inward facing surfaces. The tissue treatment element can be constructed and arranged to deliver energy to the target tissue segment inward facing surfaces with an energy selected from the group consisting of: RF; ultrasound; laser light; non-laser light such as non-laser light from an LED; chemical; and combinations thereof. The system can further comprise a laser, such as when the tissue treatment element is constructed and arranged to deliver light energy provided by the laser. The system can further comprise at least one fiber (e.g. a single fiber or a coherent or non-coherent bundle of fibers), and the light energy can be delivered through the at least one fiber. The system can further comprise a balloon, and the light energy can be delivered to and/or from the balloon. The system can further comprise light-scattering material, and the balloon can be constructed and arranged to surround the light-scattering material, such as light-scattering material selected from the group consisting of: reflective polystyrene particles; aluminum flakes; reflective microspheres; and combinations thereof. The balloon can comprise multiple apertures, such as an array of apertures in a symmetric or non-symmetric pattern, each aperture relatively transparent to the treatment element light energy being delivered to the target tissue. The laser can comprise a laser selected from the group consisting of: CO2; Erbium; fiber laser; solid state crystal laser such as a Ho:YAG laser; semiconductor laser; and combinations thereof. The laser can deliver light with a wavelength selected from the group consisting of: 2.0 to 2.2 micron; 1.8 to 2.0 micron; 1.24 to 1.64 micron; and combinations thereof. The laser can deliver light with a wavelength of 1.9 micron wavelength and/or 2.1 micron wavelength. The system can be constructed and arranged to deliver light energy in an array of light beams. The system can further comprise an array of lenses and/or other optical components, and the light energy can be distributed to target tissue by the optical components, such as an array of lenses comprising two or more lenses selected from the group consisting of: holographic; fresnel; and combinations thereof. The tissue treatment element can comprise an energy distribution element, such as an energy distribution element comprising an element selected from the group consisting of: rotating element such as a rotating mirror; prism; diffractive optic; and combinations thereof. The one or more energy delivery zones can each comprise an area between 1.0 cm$^2$ and 5.0 cm$^2$. The system can be constructed and arranged to expand one or more layers of tissue. The system can further comprise a non-energy absorbing material, and the system can be constructed and arranged to expand the one or more layers of tissue by injection of the non-energy absorbing material into tissue. The system can further comprise an energy absorbing material, and the system can be constructed and arranged to expand the one or more layers of tissue by injection of the energy absorbing material into tissue, such as when the energy absorbing material comprises water and/or saline. The tissue treatment element can comprise multiple electrodes constructed and arranged to deliver radiofrequency energy. The tissue treatment element can comprise an expandable balloon and the multiple electrodes can comprise multiple conductive dots positioned on the expandable balloon. The multiple electrodes can be constructed and arranged to deliver monopolar and/or bipolar radiofrequency energy. The multiple electrodes can comprise an array of electrodes positioned on any expandable element.

In some embodiments, the system further comprises a light source and the tissue treatment element comprises a balloon configured to deliver light energy received from the light source. The balloon can comprise multiple apertures such that the light energy passes through the multiple apertures. The system can further comprise light-scattering material positionable within the balloon and constructed and arranged to scatter the light energy. The light source can comprise a laser light source.

In some embodiments, the tissue treatment element is constructed and arranged to cause a reduction in a gastrointestinal tissue characteristic selected from the group consisting of: the average height of mucosal folds; surface area of mucosal folds; number of mucosal folds; and combinations thereof.

In some embodiments, the tissue treatment element is constructed and arranged to reshape mucosal tissue. The tissue treatment element can be constructed and arranged to flatten mucosal tissue. The tissue treatment element can be constructed and arranged to cause mucosal tissue to reshape at least 7 days after the tissue treatment is performed. The tissue treatment element can be constructed and arranged to cause mucosal tissue to reshape within 1 day of tissue treatment, such as when the tissue treatment element is constructed and arranged to deliver light energy and/or RF energy.

In some embodiments, the tissue treatment element is constructed and arranged to cause a reduction in average villi length.

In some embodiments, the tissue treatment element is constructed and arranged to cause a reduction in the quantity of villi.

In some embodiments, the tissue treatment element is constructed and arranged to reshape submucosal tissue. The tissue treatment element can be constructed and arranged such that the reshaped submucosal tissue causes a healing response resulting in a reduced amount of mucosal tissue. The reshaped submucosal tissue can comprise flattened submucosal tissue. The reshaped submucosal tissue can comprise submucosal tissue with increased uniformity of thickness. The reshaped submucosal tissue can comprise submucosal tissue with increased averaged minimum thickness. The tissue treatment element can be constructed and arranged to deliver controlled thermal heating of the submucosal tissue, such as when the controlled thermal heating is constructed and arranged to cause collagen of the submucosal tissue to shrink and/or become denatured. The tissue treatment element can be constructed and arranged to cause submucosal tissue to reshape at least 7 days after the target tissue treatment is performed.

In some embodiments, the tissue treatment element is constructed and arranged to reduce the volume of submucosal tissue.

In some embodiments, the tissue treatment element is constructed and arranged to reduce the amount of submucosal tissue on which mucosal tissue grows.

In some embodiments, the tissue treatment element is constructed and arranged to smooth the surface of the at least a portion of the gastrointestinal tract.

In some embodiments, the tissue treatment element is constructed and arranged to reduce the quantity of plicae circulares in the at least a portion of the gastrointestinal tract.

In some embodiments, the tissue treatment element is constructed and arranged to cause a reduction in surface area of absorptive tissue in the at least a portion of the gastrointestinal tract.

In some embodiments, the tissue treatment element is constructed and arranged to treat stem cells. The tissue treatment element can be constructed and arranged to treat stem cells comprising mucosal stem cells and/or epithelial stem cells. The tissue treatment element can be constructed and arranged to remove and/or ablate stem cells.

In some embodiments, the tissue treatment element is constructed and arranged to cause a reduction in the number of enteroendocrine cells in the at least a portion of the gastrointestinal tract.

In some embodiments, the tissue treatment element is constructed and arranged to cause a reduction in the number of absorptive cells in the at least a portion of the gastrointestinal tract.

In some embodiments, the tissue treatment element is constructed and arranged to reduce the surface area of the duodenum and/or the jejunum. The tissue treatment element can be constructed and arranged to reduce the surface area of the duodenum and/or the jejunum by at least 5%, at least 10%, at least 20%, at least 50% or at least 90%.

In some embodiments, the tissue treatment element comprises at least an expandable portion constructed and arranged to expand to a diameter between 10 and 40 mm. The tissue treatment element can comprise at least an expandable portion constructed and arranged to expand to a diameter between 15 and 32 mm. The expandable portion comprises an element selected from the group consisting of: balloon; expandable cage; radially deployable arm; and combinations thereof.

In some embodiments, the tissue treatment element is constructed and arranged to be radially deflected. The distal portion of the shaft can be constructed and arranged to be radially deflected, such as when the tissue treatment element is positioned on the distal portion of the shaft.

In some embodiments, the tissue treatment element is constructed and arranged to be rotated and/or translated. The tissue treatment element can be constructed and arranged to be both rotated and translated.

In some embodiments, the tissue treatment element is constructed and arranged to ablate tissue.

In some embodiments, the tissue treatment element is constructed and arranged to vaporize tissue.

In some embodiments, the tissue treatment element is constructed and arranged to cause coagulation necrosis.

In some embodiments, the tissue treatment element comprises an energy delivery element. The tissue treatment element can comprises a balloon constructed and arranged to receive a hot fluid. The hot fluid can be initially provided to the balloon at a temperature greater than or equal to 90° C., and the temperature can decrease during the course of treating the target tissue, such as a decrease to a temperature greater than 70° C. The balloon can be constructed and arranged to receive a fixed volume bolus of fluid. The balloon can be constructed and arranged to receive a recirculating fluid. A cooling fluid can be delivered to the balloon, such as to cool target tissue and/or non-target tissue prior to or after target tissue treatment. The energy delivery element can comprise an RF energy delivery element, such as an expandable RF energy delivery element. The energy delivery element can comprise an element selected from the group consisting of: laser; RF; ultrasound; and combinations thereof.

In some embodiments, the tissue treatment element comprises a tissue cutting element. The tissue treatment element can be constructed and arranged to cut tissue during advancement and/or retraction of the tissue cutting element. Alternatively or additionally, the tissue treatment element can comprise a tissue grasping element. The tissue treatment element can be constructed and arranged to grasp and/or cut tissue.

In some embodiments, the tissue treatment element is constructed and arranged to deliver energy to less than 100% (of the surface area) of each of the multiple energy delivery zones. The tissue treatment element can be constructed and arranged to deliver energy to less than 50% of each of the multiple energy delivery zones, or less than 20%, or less than 10%, or less than 5%, or less than 2% or less than 1% of each of the multiple energy delivery zones.

In some embodiments, the tissue treatment element is constructed and arranged to perform a fractional energy delivery of energy to target tissue.

In some embodiments, the tissue treatment element is positioned on the distal portion of the shaft.

In some embodiments, the tissue treatment element comprises an expandable tissue treatment element.

In some embodiments, the system is constructed and arranged to determine apposition of the tissue treatment element against tissue.

In some embodiments, the shaft is constructed and arranged to be inserted into the patient. The system may further comprise a guidewire, and the shaft can be constructed and arranged to be inserted into the patient over the guidewire. The shaft can be constructed and arranged to be inserted thru an endoscope and/or alongside an endoscope.

In some embodiments, the shaft comprises a distal end with a bulbous element positioned on the distal end. The bulbous element can comprise a diameter of less than 6 mm or less than 4 mm. The bulbous element can comprise a diameter of at least 8 mm. The bulbous element can be constructed and arranged to smoothly traverse plicae.

In some embodiments, the system further comprises a handle positioned on the proximal end of the shaft. The handle can comprise at least one fluid port constructed and arranged to deliver ablative fluid to the tissue treatment element.

In some embodiments, the system further comprises an endoscope.

In some embodiments, the system further comprises a sizing device constructed and arranged to perform a tissue measurement procedure. The sizing element can comprise an expandable element constructed and arranged to expand to measure diameter of tubular tissue. The expandable element can comprise an element selected from the group consisting of: balloon; expandable cage; and combinations thereof. The sizing element can be positioned on the shaft. The system can further comprise a second elongate shaft, and the sizing element can be positioned on the second shaft. The tissue treatment element can comprise the sizing element.

In some embodiments, the system further comprises a tissue expansion element constructed and arranged to expand one or more layers of tissue. The tissue expansion element can comprise a fluid delivery element selected from the group consisting of: needle; water jet; iontophoretic fluid delivery element; and combinations thereof. The tissue expansion element can be positioned on the shaft. The system can further comprise a second elongate shaft, and the tissue expansion element can be positioned on the second elongate shaft. The tissue expansion element can be constructed and arranged to flatten plicae circulares tissue. The system can further comprise a fluid delivery assembly and a fluid bolus, and the fluid delivery assembly can be constructed and arranged to deliver the bolus of fluid to one or more tissue sites to expand the one or more layers of tissue. The bolus of fluid can comprise a bolus of at least 1 ml, such as a bolus of fluid between 2 ml and 5 ml. The fluid bolus can comprise an injectable material selected from the group consisting of: water; saline; gel; and combinations thereof. The fluid bolus can comprise a protein hydrogel. The tissue expansion element can be constructed and arranged to deliver fluid to multiple tissue injection sites. The tissue expansion element can be constructed and arranged to deliver fluid to three circumferential tissue injection sites along a single axial location of tubular tissue. The multiple tissue injection sites can be approximately 1 cm apart, or between 0.5 cm to 5 cm apart, such as between 1 cm and 3 cm apart, or between 1 cm and 2 cm apart. The multiple tissue injection sites can be axially spaced and/or radially spaced. The multiple tissue injection sites can be located in tubular tissue, and the axial spacing and/or radial spacing can be based on the diameter of the tubular tissue. The tissue expansion element can comprise a vacuum port constructed and arranged to apply a vacuum to tissue.

In some embodiments, the system further comprises a tissue protection element. The tissue protection element can be constructed and arranged to protect the ampulla of Vater. The tissue protection element can be constructed and arranged to be deployed before a segment of target tissue is treated. The tissue protection element can be constructed and arranged to be deployed before any target tissue is treated. The tissue protection element can be constructed and arranged to be removed during the treatment of the target tissue. The tissue protection element can be constructed and arranged to be evacuated by the patient's gastrointestinal system. The tissue protection element can comprise a thermal barrier and/or a thermal spacer.

In some embodiments, the system further comprises a second tissue treatment element. The system can further comprise a second elongate shaft, and the second tissue treatment element can be positioned on the second shaft.

In some embodiments, the system further comprises a visualization element. The visualization element can comprise a visible light camera.

In some embodiments, the system further comprises an imaging agent.

In some embodiments, the system further comprises a controller constructed and arranged to control and/or monitor a system parameter. The system parameter can be selected from the group consisting of: a priming procedure parameter such as priming temperature or priming duration; target tissue treatment parameter such as target tissue temperature or target tissue treatment duration; fluid flow rate such as treatment fluid flow rate; a pressure parameter such as a tissue treatment element pressure maintained during treatment of target tissue; a tissue treatment element diameter such as a tissue treatment element diameter maintained during treatment of target tissue; and combinations thereof. The system parameter can comprise a tissue treatment element parameter, such as a parameter selected from the group consisting of: thermal dose delivered; priming temperature; tissue treatment temperature; fluid flow rate; pumping pressure; vacuum pressure; tissue treatment time; and combinations thereof. The system can further comprise a balloon, and the controller can be constructed and arranged to control the diameter of the balloon.

In some embodiments, the system further comprises an algorithm. The algorithm can be constructed and arranged to determine an energy delivery zone parameter, such as an energy delivery zone parameter selected from the group consisting of: anatomical location of an energy delivery zone; size of energy delivery zone; percentage of energy delivery zone to receive energy; type of energy to be delivered to an energy delivery zone; amount of energy to be delivered to an energy delivery zone; and combinations thereof. The algorithm can be constructed and arranged to determine the completion status of the clinical procedure. The algorithm can employ patient clinical data and/or patient demographic data.

In some embodiments, the system further comprises a motion transfer assembly operably attached to the tissue treatment element. The motion transfer assembly can be constructed and arranged to rotate and/or translate the tissue treatment element, such as when the motion transfer assembly is constructed and arranged to both rotate and translate the tissue treatment element. The motion transfer assembly can be constructed and arranged to move the tissue treatment element in a reciprocating motion.

In some embodiments, the system further comprises a pumping assembly constructed and arranged to deliver and/or remove fluid from the tissue treatment element. The system can further comprise a fluid reservoir fluidly attached to the pumping assembly.

According to another aspect of the present inventive concepts, a device for delivering light energy to a patient comprises an elongate shaft with a distal portion and a tissue treatment element positioned on the elongate shaft. The tissue treatment element is constructed and arranged to deliver light energy to target tissue positioned in one or more energy delivery zones. The device is constructed and arranged to reduce the luminal surface are of at least a portion of the gastrointestinal tract.

In some embodiments, the device further comprises one or more fibers positioned within the shaft, and the light energy can be configured to pass through the one or more fibers (e.g. a single fiber or multiple fibers in a coherent or non-coherent bundle).

In some embodiments, the tissue treatment element is positioned on the distal portion of the shaft.

In some embodiments, the tissue treatment element comprises a balloon. The device can further comprise light-scattering material, and the balloon can be constructed and arranged to surround the light-scattering material. The light-scattering material can comprise material selected from the group consisting of: reflective polystyrene particles; aluminum flakes; reflective microspheres; and combinations thereof. The balloon can comprise multiple apertures.

In some embodiments, the light energy is received from a light source operably attached to the shaft. The device can further comprise a handle attached to the shaft, and the light source can be operably attached to the handle.

In some embodiments, the light energy comprises laser light energy. The laser light energy can comprise light energy delivered from a laser selected from the group consisting of: CO2; Erbium; fiber laser; solid state crystal laser such as a Ho:YAG laser; semiconductor laser; and combinations thereof.

In some embodiments, the light energy comprises light with a wavelength selected from the group consisting of: 2.0 to 2.2 micron; 1.8 to 2.0 micron; 1.24 to 1.64 micron; and combinations thereof.

In some embodiments, the light energy comprises light with a wavelength of 1.9 micron wavelength and/or 2.1 micron wavelength.

In some embodiments, the device is constructed and arranged to deliver light energy in an array of light beams.

In some embodiments, the device further comprises an array of lenses, and the light energy can be distributed to target tissue by the array of lenses. The array of lenses can comprise two or more lenses selected from the group consisting of: holographic; fresnel; and combinations thereof.

In some embodiments, the tissue treatment element comprises a light energy distribution element. The light energy distribution element can comprise an element selected from the group consisting of: rotating element such as a rotating mirror; prism; diffractive optic; and combinations thereof.

In some embodiments, the tissue treatment element is constructed and arranged to reduce the surface area of the duodenum and/or the jejunum. The tissue treatment element can be constructed and arranged to reduce the surface area of the duodenum and/or the jejunum by at least 5%, or at least 10%, or at least 20%, or at least 50%, or at least 90%.

In some embodiments, the tissue treatment element is constructed and arranged to deliver light energy to less than 100% of each of the multiple energy delivery zones, such as to less than 50%, less than 20%, less than 10%, less than 5%, less than 2% or less than 1% of each of the multiple energy delivery zones.

In some embodiments, the tissue treatment element is constructed and arranged to perform a fractional energy delivery of light energy to target tissue.

According to another aspect of the present inventive concepts, a method for treating a patient comprises providing a tissue treatment element constructed and arranged to deliver energy to tissue; and treating target tissue of the patient by causing the tissue treatment element to deliver energy to an energy delivery zone. The method is constructed and arranged to cause a reduction in the surface area of at least a portion of a tissue surface of the patient.

In some embodiments, the method treats a disease or disorder selected from the group consisting of: diabetes; pre-diabetes; impaired glucose tolerance; insulin resistance; obesity or otherwise being overweight; hypercholesterolemia; exercise intolerance; psoriasis; hypertension; hypertriglyceridemia; metabolic syndrome; and combinations thereof.

In some embodiments, the method treats at least a first patient disease or disorder and a second patient disease or disorder.

In some embodiments, the target tissue comprises tissue of the terminal ileum and the method treats at least one of hypercholesterolemia or diabetes, such as when the target tissue further comprises tissue of at least the proximal ileum or the colon.

In some embodiments, the target tissue comprises gastric mucosal tissue and the method treats at least one of obesity or an appetite disorder.

In some embodiments, the target tissue comprises bladder wall tissue and the method treats at least one of: interstitial cystitis; bladder cancer; bladder polyps; or pre-cancerous lesions of the bladder.

In some embodiments, the target tissue comprises tissue selected from the group consisting of: large colonic polyps; flat colonic polyps; margin tissue remaining after a polypectomy; and combinations thereof, and the method treats residual cancer cells.

In some embodiments, the target tissue comprises airway lining tissue and the method treats at least one of: bronchoalveolar carcinoma; other lung cancers; or pre-cancerous lung lesions.

In some embodiments, the target tissue comprises a portion of the intestinal tract afflicted with inflammatory bowel disease and the method treats at least one of Crohn's disease or ulcerative colitis.

In some embodiments, the target tissue comprises oral cavity tissue and the method treats at least one of oral cancer or a pre-cancerous lesion.

In some embodiments, the target tissue comprises tissue of the nasopharynx and the method treats nasal polyps.

In some embodiments, the target tissue comprises gastrointestinal tissue and the method treats at least one of Celiac disease or intestinal barrier function.

The technology described herein, along with the attributes and attendant advantages thereof, will best be appreciated and understood in view of the following detailed description taken in conjunction with the accompanying drawings in which representative embodiments are described by way of example.

BRIEF DESCRIPTION OF THE DRAWINGS

The advantages of the technology described above, together with further advantages, may be better understood by referring to the following description taken in conjunction with the accompanying drawings. The drawings are not necessarily to scale, emphasis instead generally being placed upon illustrating the principles of the technology.

FIG. 1 is a flow chart of a method of treating target tissue in a patient, consistent with the present inventive concepts.

FIG. 6 is a side sectional view of the distal portion of a treatment device inserted into a curvilinear section of the GI tract, consistent with the present inventive concepts.

FIGS. 7A, 7B and 7C are end sectional views of a tubular segment of gastrointestinal tissue, prior to tissue expansion, after tissue expansion and after target tissue treatment, respectively, consistent with the present inventive concepts.

FIGS. 8A, 8B and 8C are end sectional views of a tubular segment of gastrointestinal tissue prior to tissue expansion, after tissue expansion and after target tissue treatment, respectively, consistent with the present inventive concepts.

DETAILED DESCRIPTION OF THE INVENTION

Figure 1A:
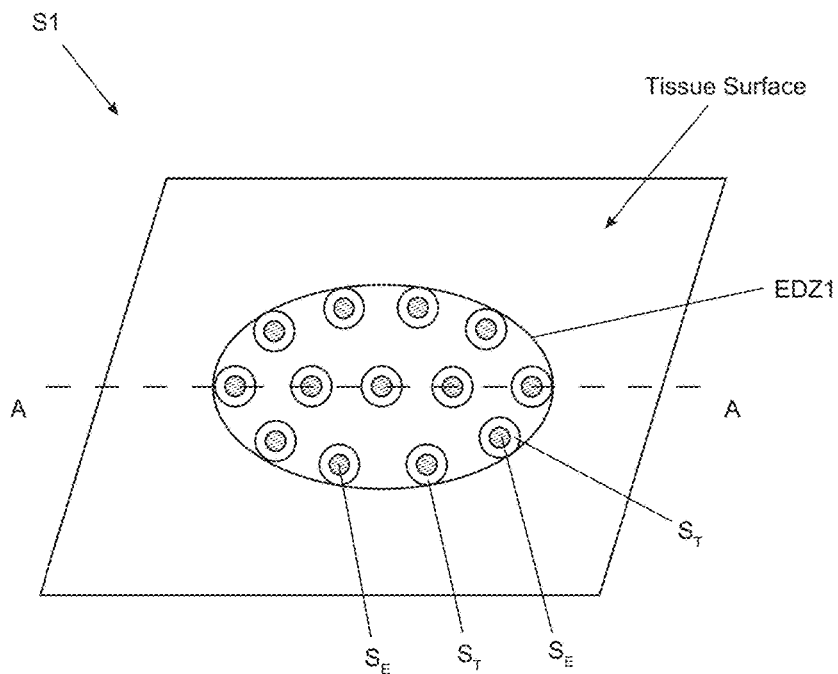
FIG. 1A is a perspective view of a tissue surface and an energy delivery zone, consistent with the present inventive concepts.

Reference will now be made in detail to the present embodiments of the inventive concepts, examples of which are illustrated in the accompanying drawings. Wherever practical, the same reference numbers will be used throughout the drawings to refer to the same or like parts.

The terminology used herein is for the purpose of describing particular embodiments and is not intended to be limiting of the inventive concepts. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on" or "connected" or "coupled" to another element, it can be directly on or above, or connected or coupled to, the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

As described herein, room pressure shall mean pressure of the environment surrounding the systems and devices of the present inventive concepts. Positive pressure includes pressure above room pressure or a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum.

As used herein, the term "ablative fluid" refers to one or more fluids whose chemical properties (at room temperature, body temperature or otherwise) cause tissue necrosis or another desired tissue treatment. "Ablative fluid" shall also refer to any fluid at a sufficiently high or low temperature to cause a desired modification of tissue, such as tissue ablation. The hot or cold ablative fluid can be delivered directly to a tissue surface to treat tissue, or it can be delivered to a reservoir such as a balloon configured to treat tissue via contact (e.g. add to or remove sufficient heat from the balloon contacted tissue to cause tissue necrosis).

It is an object of the present inventive concepts to provide systems, methods and devices for safely and effectively cutting, abrading, ablating, removing and/or otherwise treating a volume of tissue (the "target tissue"), such as to treat a patient disease or disorder. Target tissue can comprise one or more target tissue segments or other target tissue portions. The target tissue can comprise one or more layers of a portion of tubular or non-tubular tissue, such as tissue of an organ or tissue of the gastrointestinal (GI) tract of a patient. The systems and devices of the present inventive concepts include one or more treatment devices configured to treat the target tissue, such as one or more devices including one or more treatment assemblies. The treatment assemblies can be configured to deliver energy to tissue, such as to cause a reduction in the surface area of tissue (e.g. the luminal surface area of tubular tissue) at or proximate to where the energy was delivered. The luminal or other tissue surface area reduction can occur acutely and/or it can take place over time such as days, weeks or months. The tissue surface area reduction can correspond to a reduction in mucosal surface area available to function in an absorptive and/or a secretory capacity. The tissue surface area reduction can provide a therapeutic benefit to the patient, such as to treat one or more diseases or disorder of the patient, as described in detail herebelow.

Each treatment assembly can comprise at least one tissue treatment element such as a balloon configured to receive ablative fluid, one or more electrodes configured to deliver RF energy, one or more light delivery elements configured to deliver laser or other light energy, and/or one or more fluid delivery elements configured to deliver an ablative fluid directly to tissue. Numerous forms of treatment assemblies and treatment elements can be included. In some embodiments, the treatment assemblies and/or the one or more treatment elements contained therein are configured as described in: applicant's co-pending, U.S. patent application Ser. No. 13/945,138, entitled "Devices and Methods for the Treatment of Tissue", filed Jan. 18, 2013; applicant's co-pending International PCT Application Serial Number PCT/

US2013/28082, entitled "Heat Ablation Systems, Devices and Methods for the Treatment of Tissue", filed Feb. 27, 2013; applicant's co-pending International PCT Application Serial Number PCT/US2013/052786, entitled "Electrical Energy Ablation Systems, Devices and Methods for the Treatment of Tissue", filed Jul. 30, 2013; applicant's co-pending International PCT Application Serial Number PCT/US2013/054219, entitled "Ablation Systems, Devices and Methods for the Treatment of Tissue", filed Aug. 8, 2013; the contents of each of which is incorporated herein by reference in its entirety.

The tissue treatment elements of the present inventive concepts can deliver energy to a particular area of tissue, the "energy delivery zone". During a single energy delivery, a treatment element can be constructed and arranged to deliver energy to a relatively continuous surface of tissue. In these continuous-surface energy delivery embodiments, the energy delivery zone comprises the continuous surface of tissue. Alternatively, a treatment element can be constructed and arranged to deliver energy to multiple discrete portions of tissue surface, with one or more tissue portions in-between that do not receive energy from the treatment element. In these segmented-surface energy delivery embodiments, the energy delivery zone is defined by a periphery of the multiple tissue surface area portions receiving energy, similar to a "convex hull" or "convex envelope" used in mathematics to define an area including a number of discrete locations that define a periphery. An energy delivery zone can comprise one or more energy delivery zones.

For example, in embodiments where the treatment element is a balloon filled with hot fluid, the energy delivery zone comprises all tissue surfaces contacted by the balloon that directly receive thermal energy from the balloon. In embodiments where the treatment element is an array of electrodes configured to deliver RF energy, the energy delivery zone comprises an area defined by the electrodes on the periphery of the array (e.g. a convex hull as described above). In embodiments where the treatment element comprises one or more fluid delivery elements delivering ablative fluid to tissue, the energy delivery zone comprises a surface defined by the periphery of tissue locations receiving the ablative fluid. In embodiments where the treatment element comprises one or more light delivery elements such as those that deliver laser energy to tissue, the energy delivery zone comprises a surface area defined by the periphery of tissue locations receiving the light energy. In embodiments in which the treatment element comprises a mechanical cutter, the energy delivery zone can comprise a surface defined by all tissue dissected or otherwise cut during a single cutting step of the mechanical cutter.

An energy delivery zone can comprise a cumulative set of energy delivery zones that receive energy simultaneously or sequentially, by one or more tissue treatment elements, such as those described immediately hereabove. An energy delivery zone can comprise a first energy delivery zone defined when a treatment element treats target tissue in a first energy delivery, plus a second energy delivery zone defined when the treatment element treats target tissue in a second energy delivery, and so on. In these embodiments, the treatment element can be translated or otherwise repositioned between energy deliveries, and each energy delivery zone associated with the position of the treatment element during the delivery of energy. Multiple energy delivery zones can receive energy in a single procedure, such as within a period of less than twenty-four hours. An energy delivery zone can comprise a similar cumulative set of multiple energy delivery zones delivered by two or more treatment elements.

In some embodiments, two or more clinical procedures are performed in which one or more volumes of target tissue are treated in each clinical procedure, such as is described in applicant's co-pending International PCT Application Serial Number PCT/US2013/063573, entitled "Methods, Systems and Devices for Performing Multiple Treatments on a Patient", filed Oct. 7, 2013. For example, a second clinical procedure can be performed at least twenty-four hours after the first clinical procedure, such as a second clinical procedure performed within six months of a first clinical procedure or a clinical procedure performed after at least 6 months from the first clinical procedure. The first and second clinical procedures can be performed using similar or dissimilar methods, and they can be performed using similar or dissimilar devices (e.g. performed with similar or dissimilar treatment elements). The first and second clinical procedures can treat similar or dissimilar volumes of target tissue (e.g. similar or dissimilar amounts of tissue treated and/or locations of tissue treated), and they can deliver energy to similar or dissimilar sets of multiple energy delivery zones. In some embodiments, the first and second clinical procedures can include treating and/or delivering energy to contiguous and/or overlapping regions of the GI tract either in the circumferential and/or axial dimensions. In other embodiments, the first and second clinical procedures can include the treatment of disparate regions of the GI tract (such as disparate regions of the duodenum, ileum, and/or stomach). The first and second clinical procedures can be performed using similar or dissimilar treatment devices. The first and second clinical procedures can comprise similar or dissimilar deliveries of energy to treat the target tissue. The first and second clinical procedures can be performed at similar or dissimilar temperatures. The second clinical procedure can be performed based on diagnostic results collected after the first clinical procedure has been performed.

Each treatment assembly of the present inventive concepts can be configured to treat target tissue in one or more locations of the patient, such as one or more contiguous or discontiguous tissue locations. The target tissue comprises a three dimensional volume of tissue, and can include a first portion, a treatment portion, whose treatment has a therapeutic benefit to a patient; as well as a second portion, a "safety-margin" portion, whose treatment has minimal or no adverse effects to the patient. "Non-target tissue" can be identified (e.g. prior to and/or during the medical procedure), wherein the non-target tissue comprises tissue whose treatment by the treatment assembly should be reduced or avoided such as to reduce or prevent an undesired effect.

The target tissue treatment can cause one or more effects to the target tissue such as an effect selected from the group consisting of: modification of cellular function; cell death; apoptosis; instant cell death; cell necrosis; denaturing of cells; removal of cells; and combinations of these. In some embodiments, the target tissue treatment is configured to create scar tissue. Target tissue can be selected such that after treatment the treated target tissue and/or the tissue that replaces the target tissue functions differently than the pre-treated target tissue, such as to have a therapeutic benefit. The modified and/or replacement tissue can have different secretions and/or quantities of secretions than the pre-treated target tissue, such as to treat diabetes and/or obesity. The modified and/or replacement tissue can have different absorptive properties than the target tissue, such as to treat diabetes, obesity and/or hypercholesterolemia. The modified and/or replacement tissue can have a different surface topography than the target tissue, such as a modification of the topography of the inner wall of the GI tract that includes a smoothing or flattening of its inner surface, such as a modification in which the luminal surface area of one or more segments of GI tract is reduced after treatment. The effect of the treatment can occur acutely, such as within twenty-four hours, or after longer periods of time such as greater than twenty-four hours or greater than one week.

Target tissue to be treated can comprise two or more discrete tissue segments, such as two or more axial segments of the GI tract. Each tissue segment can comprise a full or partial circumferential segment of the tissue segment. Multiple tissue segments can be treated with the same or different treatment elements, and they can be treated simultaneously or in sequential steps (e.g. sequential energy delivery steps that deliver energy to multiple energy delivery zones). Multiple tissue segments can be treated in the same or different clinical procedures (e.g. procedures performed on different days). In some embodiments, a series of tissue segments comprising a series of axial segments of the GI tract are treated in a single clinical procedure. The first and second tissue segments can be directly adjacent and they can contain overlapping portions of tissue. Dissimilarities in treatment elements can include type and/or amount of energy to be delivered by an energy delivery based treatment assembly. Dissimilarities in target tissue treatments can include: target tissue area treated; target tissue volume treated; target tissue length treated; target tissue depth treated; target tissue circumferential portion treated; ablative fluid type, volume and/or temperature delivered to a reservoir such as a balloon; ablative fluid type, volume and/or temperature delivered directly to tissue; energy delivery type; energy delivery rate and/or amount; peak energy delivered; average temperature of target tissue achieved during target tissue treatment; maximum temperature achieved during target tissue treatment; temperature profile of target tissue treatment; duration of target tissue treatment; surface area reduction achieved by target tissue treatment; and combinations of these.

Target tissue can include tissue of the duodenum, such as tissue including substantially all or a limited portion of the mucosal layer of the duodenum (e.g. including all or a portion of the plicae circulares), such as to treat diabetes and/or obesity while leaving the duodenum anatomically connected after treatment. Target tissue can include one or more portions of a tissue layer selected from the group consisting of: mucosa; mucosa through superficial submucosa; mucosa through mid-submucosa; mucosa through deep-submucosa; and combinations of these. Replacement tissue can comprise cells that have migrated from one or more of: gastric mucosa; jejunal mucosa; an untreated portion of the duodenum whose mucosal tissue functions differently than the treated mucosal tissue functions prior to treatment; and combinations of these. Replacement tissue can include one or more tissue types selected from the group consisting of: scar tissue; normal intestinal mucosa; gastric mucosa; and combinations of these. In some embodiments, target tissue includes a treatment portion comprising the mucosal layer of the duodenum, and a safety-margin portion comprising a near-full or partial layer of the submucosal layer of the duodenum. In some embodiments, the target tissue comprises nearly the entire mucosal layer of the duodenum, and can include a portion of the pylorus contiguous with the duodenal mucosa and/or a portion of the jejunum contiguous with the duodenal mucosa. In other embodiments, the target tissue comprises up to 50% or up to 75% of the mucosal layer, such as when up to 50% or up to 75%, respectively, of the length of the duodenum is treated by an tissue treatment element delivering energy to full circumferential axial segment of the duodenum.

Treatment of duodenal tissue can be performed to treat a disease and/or disorder selected from the group consisting of: diabetes; pre-diabetes; impaired glucose tolerance; insulin resistance; obesity or otherwise being overweight; a metabolic disorder and/or disease; and combinations of these. A near full circumferential portion (e.g. approximately) 360° of the mucosal layer of one or more axial segments of GI tissue can be treated. In some embodiments, less than 360° of one or more axial segments of tubular tissue is treated, such as one or more circumferential portions less than 350°, or between 300° and 350°, such as to prevent a full circumferential scar from being created at the one or more axial segment locations.

Target tissue can be selected to treat two or more patient diseases or disorders, such as two or more patient diseases or disorders are described herein.

Target tissue can comprise tissue of the terminal ileum, such as to treat hypercholesterolemia and/or diabetes. In these embodiments, the target tissue can extend into the proximal ileum and/or the colon.

Target tissue can comprise gastric mucosal tissue, such as tissue regions that produce ghrelin and/or other appetite regulating hormones, such as to treat obesity and/or an appetite disorder.

Target tissue can comprise bladder wall tissue, such as to treat a disease and/or disorder selected from the group consisting of: interstitial cystitis; bladder cancer; bladder polyps; pre-cancerous lesions of the bladder; and combinations of these.

Target tissue can comprise tissue selected from the group consisting of: large and/or flat colonic polyps; margin tissue remaining after a polypectomy; and combinations of these. These tissue locations can be treated to treat residual cancer cells.

Target tissue can comprise esophageal tissue and/or gastric tissue. In some embodiments, target tissue comprises cancerous or precancerous tissue treated with a single or multiple energy deliveries, in single or multiple clinical procedures. In some embodiments, target tissue is treated as a treatment of Barrett's esophagus.

Target tissue can comprise airway lining tissue, such as to treat a disease and/or disorder selected from the group consisting of: bronchoalveolar carcinoma; other lung cancers; pre-cancerous lung lesions; and combinations of these.

Target tissue can comprise at least a portion of the intestinal tract afflicted with inflammatory bowel disease, such that Crohn's disease and/or ulcerative colitis can be treated.

Target tissue can comprise tissue of the oral cavity, such as to treat one or more of: oral cancers and a pre-cancerous lesion of the oral cavity.

Target tissue can comprise tissue of the nasopharynx, such as to treat nasal polyps.

Target tissue can comprise GI tissue selected to treat Celiac disease and/or to improve intestinal barrier function.

The treatment assemblies, systems, devices and methods of the present inventive concepts can be configured to avoid ablating or otherwise adversely affecting certain tissue, termed "non-target tissue" herein. Depending on the location of tissue intended for treatment (i.e. target tissue), different non-target tissue can be applicable. In certain embodiments, non-target tissue can comprise tissue selected from the group consisting of: gastrointestinal adventitia; duodenal adventitia; the tunica serosa; the tunica muscularis; the outermost partial layer of the submucosa; ampulla of Vater such as during mucosal treatment proximate the ampulla of Vater; pancreas; bile duct; pylorus; and combinations of these.

The treatment assemblies, treatment elements and other functional elements of the present inventive concepts can be configured to automatically and/or manually expand in at least a radial direction. Typical expandable elements include but are not limited to: an inflatable balloon; a radially expandable cage or stent; one or more radially deployable arms; an expandable helix; an unfurlable compacted coiled structure; an unfurlable sheet; an unfoldable compacted structure; and combinations of these. In some embodiments, the expandable elements can comprise a radially expandable tube, such as a sheet of material resiliently biased in a radially expanded condition that can be compacted through a furling operation, or a sheet of material resiliently biased in a radially compact condition that can be expanded through an unfurling operation. The expandable elements can comprise a foldable sheet, such as a sheet configured to be folded to be radially compacted and/or to be unfolded to radially expand. In some embodiments, the expandable elements expand to contact tissue, such as to expand to a diameter similar to the diameter of the luminal wall tissue into which the expandable element has been placed. In some embodiments, the expandable elements expand to be closer to wall tissue, but remain at a distance (e.g. a fixed or pre-determined distance) from the tissue surface. In some embodiments, the expandable elements expand to be larger than the diameter of the luminal wall tissue into which the expandable element has been placed, such as to improve the quality of the apposition of the expandable element against the uneven surface of the tissue. In these embodiments, the fully expanded diameter of the expandable elements would be configured to avoid a diameter large enough to cause lasting mechanical damage to the apposed tissue and/or to tissue proximate the apposed tissue.

Any device of the present inventive concepts can include one or more treatment elements configured to deliver energy to one or more energy delivery zones, to treat at least a portion of target tissue. Any device can include one or more fluid delivery elements, such as one or more nozzles configured to deliver fluid to tissue. The fluid delivery elements can be constructed and arranged to deliver fluid to perform a function selected from the group consisting of: expanding one or more tissue layers; warming or cooling tissue; removing debris or other substance from a tissue surface; delivering energy to an energy delivery zone comprising a continuous or segmented surface; treating target tissue; and combinations of these. Any of the expandable assemblies of the present inventive concepts can include one or more other functional elements, such as are described in reference to the figures herebelow. The treatment elements, fluid delivery elements, and/or other functional elements can be mounted on, within (e.g. within the wall) and/or inside of an expandable element such as a balloon or expandable cage. In some embodiments, one or more functional elements is not mounted to an expandable element, such as those attached to a shaft or other non-expandable treatment device component.

In some embodiments, the treatment device comprises at least one treatment element configured to deliver energy to an energy delivery zone such as to ablate target tissue. Examples of ablation elements include but are not limited to: an expandable reservoir such as a balloon configured to receive fluid at a temperature sufficient to ablate tissue; fluid delivery elements configured to deliver ablative fluid directly to target tissue; a radiofrequency (RF) energy delivery element such as one or more electrodes; an ultrasonic transducer such as one or more piezo crystals configured to ablate tissue; a laser energy delivery element such as one or more optical fibers and/or laser diodes; a rotating ablation element; a circumferential array of ablation elements; and combinations of these.

The balloons of the present inventive concepts can be divided into two general categories: those that are composed of a substantially elastic material, such as silicone, latex, low-durometer polyurethane, and the like; and those that are composed of a substantially inelastic material, such as polyethylene terephthalate (PET), nylon, high-durometer polyurethane and the like. A third category includes balloons which include both elastic and inelastic portions. Within the category of elastic balloons, two subcategories exist: a first sub-category wherein a combination of material properties and/or wall thickness can be combined to produce a balloon that exhibits a measurable pressure-threshold for inflation (i.e. the balloon becomes inflated only after a minimum fluidic pressure is applied to the interior of the balloon); and a second sub-category, wherein the balloon expands elastically until an elastic limit is reached which effectively restricts the balloon diameter to a maximum value. The individual properties of the balloons in each of these categories can be applied to one or more advantages in the specific embodiments disclosed herein, these properties integrated singly or in combination. By way of example only, one or more of the following configurations can be employed: a highly elastic balloon can be used to achieve a wide range of operating diameters during treatment (e.g. during operation a desired balloon diameter can be achieved by adjustment of a combination of fluid temperature and pressure); a substantially inelastic balloon or a balloon that reaches its elastic limit within a diameter approximating a target tissue diameter (e.g. a duodenal mucosal diameter) can be used to achieve a relatively constant operating diameter that will be substantially independent of operating pressure and temperature; a balloon with a pressure-threshold for inflation can be used to maintain an uninflated diameter during relatively low pressure conditions of fluid flow and then achieve a larger operating diameter at higher pressure conditions of flow. Pressure-thresholded balloons can be configured in numerous ways. In one embodiment, a balloon is configured to have a relatively thick wall in its uninflated state, such as to maximize an electrically and/or thermally insulating effect while the balloon is maintained in this uninflated state. The balloon can be further configured such that its wall thickness decreases during radial expansion (e.g. to decrease an electrically and/or thermally insulating effect). In another embodiment, a balloon is configured to have a relatively small diameter in its uninflated state (e.g. a diameter that is small relative to the inner diameter of tubular target tissue such as the diameter of the mucosal layer of duodenal wall tissue), such as to minimize or completely eliminate apposition between the balloon and the surrounding tissue to minimize heat, RF and/or other energy transfer into the surrounding tissue until the balloon is fully inflated. In another embodiment, a balloon and an ablation system or device are configured to circulate a flow of fluid through the balloon (e.g. an elastic balloon or an inelastic balloon) at a sufficiently low enough pressure to prevent apposition of the balloon or other device component with target tissue, such as to pre-heat one or more surfaces of the ablation system or ablation device that are in fluid communication with the balloon. In this configuration, when the balloon or other ablation element is positioned to deliver energy to target tissue, the temperature of the balloon or other ablation element will be at a desired level or it will rapidly and efficiently reach the desired level for treatment (i.e. minimal heat loss to the fluid path components due to the pre-heating or pre-cooling). These configurations provide a method of delivering energy to tissue with an ablative fluid filled balloon. A "thermal priming" procedure can be performed prior to one or more target tissue treatments, such as to improve thermal response time of one or more portions of the treatment device. Ablative fluid filled balloon treatment devices as well as thermal priming devices and methods can be configured as is described in applicant's copending International PCT Application Serial Number PCT/US2013/28082, entitled "Heat Ablation Systems, Devices and Methods for the Treatment of Tissue", filed Feb. 27, 2013, the contents of which is incorporated herein by reference in its entirety.

At times during target tissue treatment when it is desirable to initiate, increase and/or otherwise modify the treatment of tissue by one or more tissue treatment elements (e.g. a fluid delivery element delivering ablative fluid, a mechanically abrasive element, a hot or cold fluid balloon delivering a thermal energy to tissue and/or an electrode delivering RF energy), the treatment assembly diameter (e.g. the diameter of a balloon, deployable cage, expandable tube or other expandable assembly) can be increased in situ to move a treatment element closer to target tissue and/or to change the contact force between the treatment element and the target tissue. At times during treatment when it is desirable to stop or otherwise decrease the amount of tissue treatment, the treatment assembly diameter can be reduced in situ, such as to prevent or reduce delivery of energy or other treatment to the target tissue by eliminating or reducing tissue contact of one or more treatment elements (e.g. electrodes, abrasive surfaces or ablative fluid filled balloons). For those cases where the native diameter of the target tissue varies substantially within the treatment zone, then a highly elastic or compliant balloon or other expandable element can be employed, such as a balloon or deployable cage which can be adjusted to achieve a wide range of operating diameters.

Alternatively or additionally, to initiate, increase and/or otherwise modify the treatment of tissue by one or more treatment elements (e.g. a fluid delivery element delivering ablative fluid, a mechanically abrasive element, a hot or cold fluid balloon delivering thermal energy to tissue and/or an electrode delivering RF energy), the diameter of the target tissue can be decreased in situ to move target tissue closer to a treatment element and/or to change the contact force between the target tissue and the treatment element. To stop or otherwise decrease ablation of tissue, the diameter of tissue neighboring a treatment element can be increased in situ, such as to prevent or reduce delivery of energy or other treatment to the target tissue by eliminating or reducing tissue contact of one or more treatment elements (e.g. electrodes, abrasive surfaces or ablative fluid filled balloons). The diameter of the tissue proximate a treatment element can be increased or decreased, independent of the treatment assembly diameter, by means of delivering and/or withdrawing a fluid, to and/or from a lumen surrounded by target tissue, such as by using standard GI insufflation techniques. Typical insufflation fluids include but are not limited to: gases such as carbon dioxide or air; liquids such as water or saline solution; and combinations of these. The insufflation fluids can be introduced through a treatment device, through an endoscope such as an endoscope through which the treatment device is inserted, and/or via another device placed proximate the target tissue. Delivery of insufflation fluids can be performed to move target tissue away from one or more treatment elements, such as to stop transfer of energy to target tissue at the end of a treatment of target tissue as described hereabove. Alternatively or additionally, delivery of insufflation fluids can be performed to manipulate tissue, such as to distend and/or elongate tissue. Removal of these insufflation fluids and/or the application of a vacuum or other negative pressure can be used to decrease the diameter of the target tissue, such as to bring the target tissue in closer proximity to one or more treatment elements and/or to increase the contact force between target tissue and one or more treatment elements, also as described hereabove. In this tissue diameter controlled approach, a treatment assembly including a balloon that can be maintained at a substantially constant diameter can be desirable, such as a substantially inelastic balloon such as a balloon with an elastic-limit.

Referring now to FIG. 1, a flow chart of a method of treating target tissue in a patient is illustrated, consistent with the present inventive concepts. The method includes providing at least a tissue treatment element configured to deliver energy to tissue. A tissue treatment system can be provided, such as system 10 of FIG. 3, including treatment element assembly 140 as described herebelow. Target tissue is treated, such as target tissue of the GI tract, by causing the treatment element to deliver energy to tissue in an energy delivery zone, as defined hereabove. The energy delivery causes a reduction in the surface area of tissue, such as a reduction in the luminal surface area of one or more portions of the GI tract.

In STEP 10, a patient assessment is performed such as to diagnose, prognose or otherwise assess one or more diseases or disorders of a patient. STEP 10 can include selecting a mammalian patient (e.g. a human) for receiving a method of the present inventive concepts. If selected, STEPs 20 through 70 can then be performed.

In STEP 20, target tissue to be treated is selected. Target tissue can include multiple tissue segments to be treated simultaneously or sequentially as described herein. In subsequent steps, additional target tissue can be identified for treatment, and previously identified target tissue can be removed from consideration of treatment. Target tissue can include but is not limited to: mucosa; mucosa through superficial submucosa; mucosa through mid-submucosa; mucosa through deep-submucosa; and combinations of these. Target tissue segments can comprise length (e.g. axial length), width (e.g. an arc length dimension such as the partial or full circumference of a surface or layer of tubular tissue) and depth dimension. In some embodiments, an axial length dimension of each target tissue segment is less than 20 cm in length, less than 15 cm in length, less than 10 cm, less than 5 cm in length or less than or equal to 3 cm in length. In some embodiments, a cumulative sum of all the target tissue axial segment length dimensions is less than 100 cm, or less than 50 cm (i.e. less than 100 cm or less than 50 cm, respectively, of the GI tract is treated).

Figure 3:
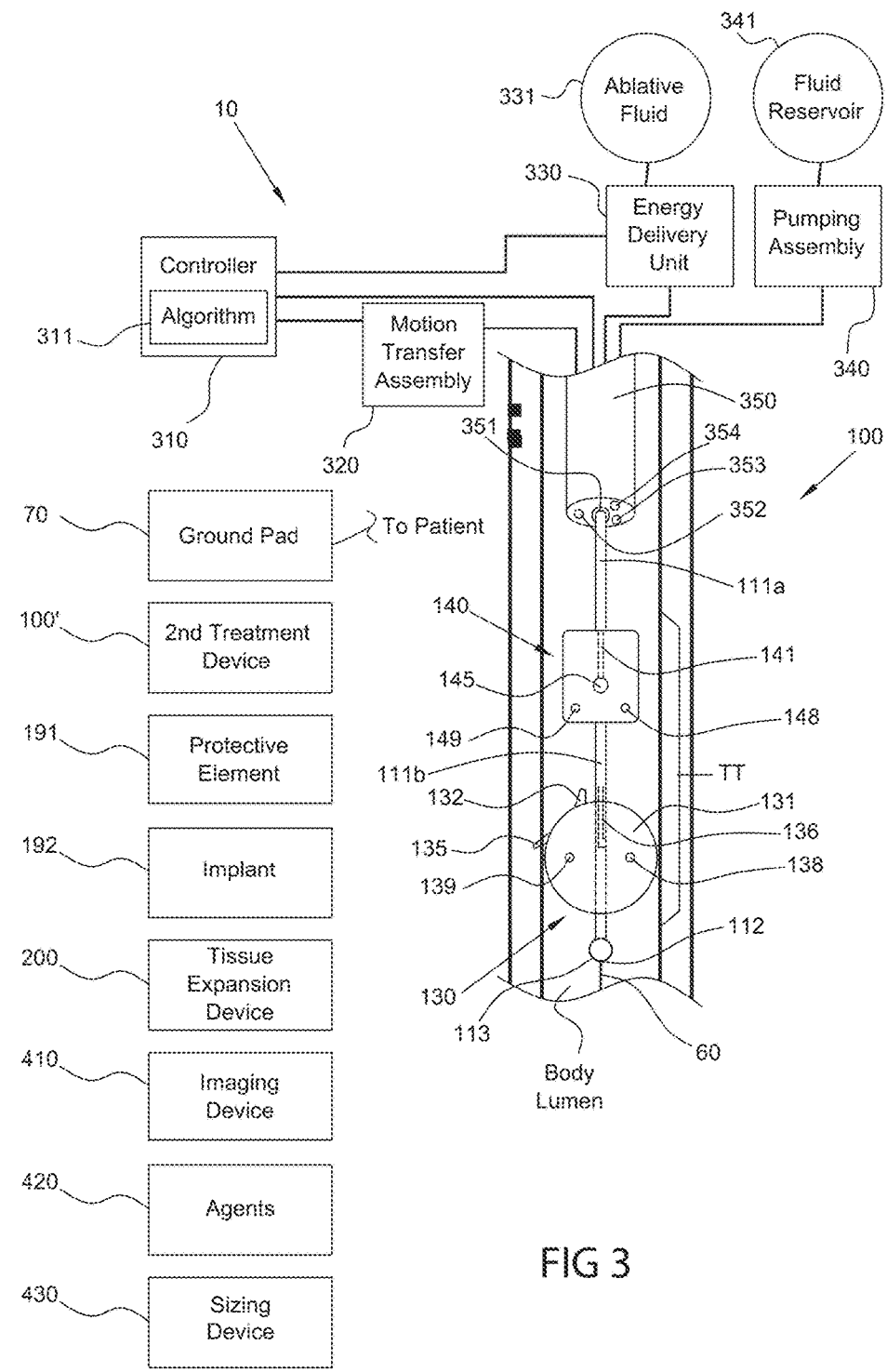
FIG. 3 is a schematic view of a system for ablating or otherwise treating target tissue, consistent with the present inventive concepts.

In STEP 30, one or more treatment devices are selected, such as those described in reference to FIG. 3 and FIG. 5 herebelow. The treatment devices provide a tissue treatment element constructed and arranged to deliver energy.

STEPs 40 comprise STEP 41, STEP 42 and STEP 43. Any of STEPs 41, 42 and 43 can be performed multiple times, in various orders, such as when the target tissue comprises multiple tissue segments that are treated sequentially. STEPs 40 can be performed with one or more components of system 10 of FIG. 3 described herebelow. One or more devices can be inserted into the body over a guidewire and/or through an endoscope, such as a sizing element, a tissue expansion element and/or a tissue treatment element that is inserted into the patient's body over a guidewire or through an endoscope.

In STEP 41, a portion of the patient's anatomy is measured, such as to measure one or more diameters (e.g. one or more diameters of in inner surface of an axial segment of the duodenum or jejunum), radius of curvature, or other geometric analysis of tissue such as a volume of tissue such as a target tissue volume, or a surface area of tissue such as a surface area of an energy delivery zone. In some embodiments, the anatomical measurement is performed using one or more devices or components of system 10 of FIG. 3 described herebelow, such as sizing device 430.

In STEP 42, one or more tissue layers of the patient are expanded, such as with a tissue expansion device and/or tissue expanding element such as those described in applicant's co-pending International PCT Application Serial Number PCT/US2013/37485, entitled "Tissue Expansion Devices, Systems and Methods", filed Apr. 19, 2013, the contents of which is incorporated herein by reference in its entirety. The tissue layers expanded can comprise target tissue and/or non-target tissue. In some embodiments, one or more measurement procedures of STEP 41 is performed to measure the expansion, changes or other dimensional information caused or otherwise related to one or more tissue expansions performed in one or more STEPs 42. In some embodiments, the expanded tissue comprises one or more layers of submucosal tissue. In some embodiments, tissue is expanded to flatten plicae of the GI tract. Tissue expansion can be accomplished with one or more fluid delivery elements, such as a fluid delivery element selected from the group consisting of: needle; water jet; iontophoretic fluid delivery element; and combinations if these, such as those described in reference to FIG. 3 herebelow. One or more fluid delivery elements can be part of a fluid delivery assembly, such as a fluid delivery assembly of system 10 of FIG. 3. A fluid delivery assembly can include reservoirs or boluses of predetermined amounts of fluid, such as a volume of fluid for an injection that is at least 1 ml, or between 2 ml and 5 ml. Fluid can be injected to multiple injection sites, such as a set of multiple injection sites selected from the group consisting of: at least three injection sites along a circumference of tubular tissue, where a first injection site can be separated from a second injection site by approximately 1 cm, or between 0.5 cm to 5 cm, or between 1 cm and 3 cm, or between 1 cm and 2 cm; two or more injection sites that are axially and/or radially spaced; two or more injections sites that are separated based on the diameter of the tubular tissue into which they are injected; and combinations of these. Fluid can be injected with the assistance of one or more vacuum applying elements, such as those described in reference to FIG. 3 herebelow. Injected fluid can comprise a material selected from the group consisting of: water; saline; gel; and combinations of these. In some embodiments, injected fluid comprises a protein hydrogel.

Tissue expanded in STEP 42 can comprise one or more layers of gastrointestinal tissue, such as one or more layers of duodenal and/or jejunal tissue. The one or more tissue layers can comprise one or more layers of submucosal tissue.

In STEP 43, target tissue is treated, such as with the one or more treatment devices selected in STEP 30. STEP 43 includes the treatment of target tissue with one or more treatment elements to deliver energy to one or more energy delivery zones within the patient's GI tract or other anatomical location as described herein. The energy delivered causes a reduction in luminal surface area of one or more portions of the patient's GI tract. The reduction in surface area can be a reduction in the surface area of the target tissue treated and/or a reduction in GI luminal surface area that results after new tissue forms as a result of the target tissue treatment (e.g. new tissue that replaces the treated target tissue).

In some embodiments, energy delivery during STEP 43 can be modified (e.g. initiated, stopped, increased and/or decreased) by changing (i.e. increasing or decreasing) the cross-sectional area of tissue surrounding a tissue treatment element. This decrease can be caused by means of delivering and/or withdrawing a fluid, to and/or from a lumen surrounded by target tissue, such as by using standard GI insufflation techniques with an insufflation device of the system of the present inventive concepts, as described hereabove. In some embodiments, apposition of a tissue treatment element is measured, such as to determine if sufficient contact is present between a tissue treatment element and target tissue.

Target tissue treatment of STEP 43 can be performed at a time related to the time of one or more tissue expansions performed in a previously performed STEP 42. In some embodiments, target tissue that has been expanded is treated at least 1 minute after expansion, or at least 5 minutes after expansion. In some embodiments, target tissue is treated within at least 20 minutes of expansion. In some embodiments, expanded tissue comprises an inner layer of an axial segment of duodenal and/or jejunal tissue, and energy is delivered to an energy delivery zone including multiple, discontinuous partial circumferential portions of the axial segment. In these embodiments, energy is not delivered to at least one partial circumferential tissue portion between two of the treated portions of the axial segment, such as is described in detail in reference to FIG. 7A-7C herebelow.

In some embodiments, STEPs 41, 42 and 43 are performed multiple times, such as to measure, expand and treat multiple tissue segments along the length of the GI tract, such as along a length of the duodenum and/or jejunum of the patient. In some embodiments, a series of geometry measurements of STEP 41 are performed continuously, after which a series of tissue expansions of STEP 42 are performed continuously, after which a series of tissue treatments of STEP 43 are performed continuously. Alternatively or additionally, one or more of STEPs 41, 42 and 43 are performed in between one or more of the other steps in an alternating fashion.

In some embodiments, between two and fifty energy delivery zones receive energy from a treatment element, such as in one to fifty STEP 43's. The multiple energy delivery zones can receive energy simultaneously or sequentially, such as within a twenty-four hour period. In some embodiments, a second procedure as described herein is performed, where a second energy delivery zone receives energy between twenty-four hours and six months after a first energy delivery zone receives energy. Multiple energy delivery zones can have overlapping and/or similar boundaries (e.g. proximal or distal boundaries), as described in detail in reference to FIG. 4 herebelow. Any of the multiple energy delivery zones can include a full or partial circumferential segment of tubular tissue, such as a full or partial circumferential portion of an axial segment of duodenal and/or jejunal tissue.

In STEP 50, the condition of the patient is assessed. STEP 50 can be performed at any time during the clinical procedure, or at a time subsequent to the clinical procedure, such as 1 week, 1 month, 3 months, 6 months or longer from the time of the clinical procedure.

In STEP 60, a determination is made whether a second treatment should be performed on the patient, such as a treatment including STEP 20 through STEPs 40 described hereabove. If a repeat procedure is deemed necessary, STEP 10 and one or more subsequent steps can be repeated. If a repeat procedure is deemed unnecessary at that time, STEP 70 is performed.

In STEP 70, a post-tissue treatment procedure can optionally be performed on the patient. In STEP 70, the patient can receive additional medical treatments including one or more pharmaceutical treatments such as a treatment including a pharmaceutical drug or other agent selected from the group consisting of: an anti-inflammatory agent such as a steroid; an immunomodulator such as Sirolumus or Tacrolimus; Sucralfate; a bismuth compound; an acid inhibitor; a proton-pump inhibitor; a H2-receptor blocker; an antibiotic; an anti-fungal; an appetite suppressant agent; an anti-obesity agent; an anti-cholesterol agent; a diabetes drug such as metformin, a GLP-1 analogue, a DPP-IV inhibitor, sulfonulereas, insulin, or an insulin analog; and combinations of these. Alternatively or additionally, the treatment can include the patient undertaking a specific diet, such as a low calorie diet. In some embodiments, the low calorie diet comprises a diet including less than 1500 calories per day, or less than 1000 calories per day. The diet can include minimizing the content of one or more substances, such as fructose, simple sugars or fats. In some embodiments, a low calorie diet is maintained during a period of time in which at least some mucosal regrowth occurs. The period after the delivery of energy can be characterized by an intense phase of mucosal regrowth, during which time the epithelial surface reconstitutes itself to provide a mucosal barrier against the environment. At the same time, the cellular architecture of the mucosa is restored in such a way as to facilitate the proper physiologic functioning of the region that was treated with energy. The physiologic function of the mucosal layer can be influenced by dietary modifications or pharmaceutical agents that affect cellular proliferation or growth by altering the number or types of cells that comprise the reconstituted mucosa. A low calorie diet, for instance, can stimulate the growth of less total mucosal mass than a high calorie diet, and can also influence the number and type of hormone-producing cells that differentiate from the stem cells that give rise to the reconstituted mucosa.

After STEP 70, STEP 50 can be re-performed, such as after an elapsed time of at least 6 months or at least one year later.

In the method of FIG. 1, the patient can be selected for treatment of one or more diseases or disorders such as those described hereabove. In some embodiments, the patient is selected to treat a disease or disorder selected from the group consisting of: diabetes; pre-diabetes; impaired glucose tolerance; insulin resistance, and combinations of these. In some embodiments, the patient is selected to treat a disease or disorder selected from the group consisting of: obesity or otherwise being overweight; hypercholesterolemia; exercise intolerance; psoriasis; hypertension; hypertriglyceridemia; metabolic syndrome; and combinations of these. The method can be performed after the patient has exhibited one or more symptoms of a disease state for a period of time, such as at least 1 year, at least 2 years or at least 5 years. In some embodiments, the patient is selected to treat type 2 diabetes. In some embodiments, a diabetic patient is treated within a time period of exhibiting diabetic physiology, such as a time period of less than 10 years, less than 5 years, less than 2 years or less than 1 year. In some embodiments, a patient selected for treatment has an HbA1c level of at least 7.5% or at least 8%.

The method of FIG. 1 can be performed to cause a reduced absorptive (e.g. reduced absorption of nutrients) and/or reduce secretory capacity (e.g. reduced secretion of gut hormones) due to the reduction of luminal surface area of at least a portion of the GI tract. In some embodiments, reduced absorption of at least one of glucose, cholesterol, a monoglyceride or a free fatty acid is achieved. The method can be constructed and arranged to cause a reduction in glucose absorption and/or gut hormone release in a surface area reduced portion of the GI tract, such as a reduction that is present in these areas during and/or after food intake by the patient. In some embodiments, a reduced release of GIP and/or another proximal gut hormone results in the surface area reduced portion of the GI tract.

The amount of target tissue selected and/or treated (e.g. including one or more continuous or discontinuous tissue segments) can be proportionally related to the longevity of the disease state being treated. The amount of target tissue selected and/or treated can comprise a volume of tissue, such as the cumulative volume of multiple continuous and/or discontinuous tissue segments. Alternatively or additionally, the amount of target tissue selected and/or treated can be represented by a length of tubular tissue, such as the cumulative length of multiple continuous and/or discontinuous axial tubular (e.g. duodenal) tissue segments each of which receives energy on one or more portions of at least 50% of its inner surface (i.e. the energy delivery zone comprises at least 50% of the inner surface of the cumulative lengths of axial tubular tissue segments). Alternatively or additionally, the amount of target tissue selected and/or treated can be represented by an amount of tissue surface area of tissue receiving energy, such as the cumulative surface area of multiple continuous and/or discontinuous tissue portions each of which receives energy on one or more portions of at least 50% of its inner surface (i.e. the energy delivery zone comprises at least 50% of the inner surface of the multiple tissue portions).

In some embodiments, the disease state comprises a diabetes state and the following proportions of target tissue treated apply: the energy delivery zone comprises less than 50% of the duodenal mucosal surface area if the patient has exhibited diabetic physiology for less than 3 years; the energy delivery zone comprises less than 50% of the duodenal mucosal surface area if the patient has exhibited diabetic physiology for less than 5 years; the energy delivery zone comprises less than 75% of the duodenal mucosal surface area if the patient has exhibited diabetic physiology for less than 7 years; or the energy delivery zone comprises less than 75% of the duodenal mucosal surface area if the patient has exhibited diabetic physiology for less than 10 years. In these and other embodiments, the percentage of the energy delivery zone receiving energy can be between 0.01% and 100% of the surface area of the energy delivery zone, such as at least 2%, at least 5%, at least 10% or at least 20% of the surface area of the energy delivery zone.

In some embodiments, the disease state comprises a diabetes state and the following proportions of target tissue treated apply: the energy delivery zone comprises less than 50% of the duodenal mucosal surface area if the patient has an HgbA1c level less than 8; the energy delivery zone comprises less than 50% of the duodenal mucosal surface area if the patient has an HgbA1c level less than 9; the energy delivery zone comprises less than 75% of the duodenal mucosal surface area if the patient has an HgbA1c level less than 10; or the energy delivery zone comprises less than 75% of the duodenal mucosal surface area if the patient has an HgbA1c level less than 12. In these and other embodiments, the percentage of the energy delivery zone receiving energy can be between 0.01% and 100% of the surface area of the energy delivery zone, such as at least 2%, at least 5%, at least 10% or at least 20% of the surface area of the energy delivery zone.

In some embodiments, the target tissue and/or the energy delivery zone is selected based on patient characteristics. Applicable patient characteristics include but are not limited to: duration of diabetes; HbA1c; area under the curve of a glucose tolerance test; area under the curve of a mixed meal tolerance test; C-peptide level; GIP level; GLP-1 level; age; BMI; and combinations of these. In some embodiments, the target tissue and/or the energy delivery zone is selected based on a target diabetes endpoint results, such as the result determined in one or more diagnostic tests. Applicable diabetic endpoint results include but are not limited to: target HbA1c level; target BMI; target area under the curve of glucose tolerance test; target cholesterol level; target triglyceride level; and combinations of these.

In some embodiments, the energy delivery zone comprises an anatomical location selected from the group consisting of: inner surface portion of stomach; full circumferential inner surface of an axial segment of duodenum; partial circumferential inner surface of an axial segment of duodenum; full circumferential inner surface of an axial segment of jejunum; partial circumferential inner surface of an axial segment of jejunum; and combinations of these. The energy delivery zone and/or target tissue can include at least one axial segment of the duodenum and/or jejunum, such as tissue comprising at least mucosal tissue of the duodenum and/or jejunum. The at least one axial segment of target tissue and/or energy delivery zone treated can include a full or partial circumferential segment of GI tissue. In some embodiments, a partial circumferential segment to be treated comprising 45° to 350° of an axial segment of tubular tissue. In additional to duodenal and/or jejunal mucosal tissue, target tissue can include tissue selected from the group consisting of: ileal mucosal tissue; gastric mucosal tissue; and combinations thereof.

Target tissue treated and/or an energy delivery zone can be positioned relative to one or more anatomical structures, such as to ensure and/or improve therapeutic benefit, and/or to prevent damage to tissue or prevent any undesired clinical event. In some embodiments, target tissue and/or an energy delivery zone comprises at least one tissue segment comprising tubular tissue with a proximal end and a distal end, such as a relatively continuous axial segment of one or more full or partial circumferential tissue layers or surfaces of the duodenum. In some embodiments, the target tissue and/or energy delivery zone proximal end is positioned distal to (i.e. away) from the ampulla of Vater, but within 5 cm or within 2 cm of the ampulla of Vater, such as when the ampulla of Vater is located and/or otherwise identified prior to one or more energy deliveries to treat target tissue. In some embodiments, tissue treatment element treats target tissue proximal to but in close proximity to the ampulla of Vater (e.g. delivers energy to an energy delivery zone proximal to but in close proximity to the ampulla of Vater). The target tissue and/or energy delivery zone proximal end can be positioned at least 10 cm from the pylorus, or at least 15 cm from the pylorus. The target tissue and/or energy delivery zone proximal end can be positioned distal to the duodenal bulb. In some embodiments, the target tissue and/or energy delivery zone proximal end is positioned at a location in the duodenum that includes the most proximal location in the duodenum that includes plicae circulares. In some embodiments, the target tissue and/or energy delivery zone proximal end is positioned at a location within 5 cm of the ampulla of Vater and the distal end is located proximal to the ligament of Treitz.

As stated above, the energy delivery zone can comprise multiple energy delivery zones that receive sequential deliveries of energy, such as sequential deliveries of energy received from a single energy delivery element or other tissue treatment element (e.g. a hot fluid balloon or electrode array) that translates within the GI tract from a first energy delivery zone to a second energy delivery zone between energy deliveries. In some embodiments, each energy delivery zone comprises a length from a proximal end to a distal end of at least 3 cm or at least 5 cm. In some embodiments, an energy delivery zone can comprise a length from its proximal end of at least 10 cm or at least 50 cm, such as when a single or few energy delivery zones receive energy during a single clinical procedure.

In some embodiments, at least one portion (e.g. at least one axial segment) of an inner surface of the duodenum and/or jejunum does not receive energy from a treatment element. The at least one non-energy-receiving surface can comprise a segment of mucosa that includes minimal or no plicae circulares. Alternatively or additionally, the at least one non-energy-receiving surface can comprise a segment of the duodenum and/or jejunum with a sharp bend, such as a curved segment of tubular tissue with an average radius of curvature less than 5 cm over a 75° arc, or less than 3 cm over a 75° arc, as described herebelow in reference to FIG. 6. Similarly, in some embodiments, one or more energy delivery zones can comprise the inner surface of relatively linear tubular tissue segments, while segments with a higher radius of curvature are avoided. In these embodiments, the energy delivery zone can comprise the inner surface of one or more full circumferential segments of tubular tissue. In some embodiments, at least a portion of an inner surface of tubular tissue may not receive energy from a tissue treatment element due to the inner surface topography that can result during a tissue expansion procedure (e.g. a submucosal tissue expansion procedure as described herein), such as when one or more valleys created by the tissue expansion do not receive energy delivered by a tissue treatment element, as described in detail below in reference to FIGS. 7A-7C.

Figure 5A:
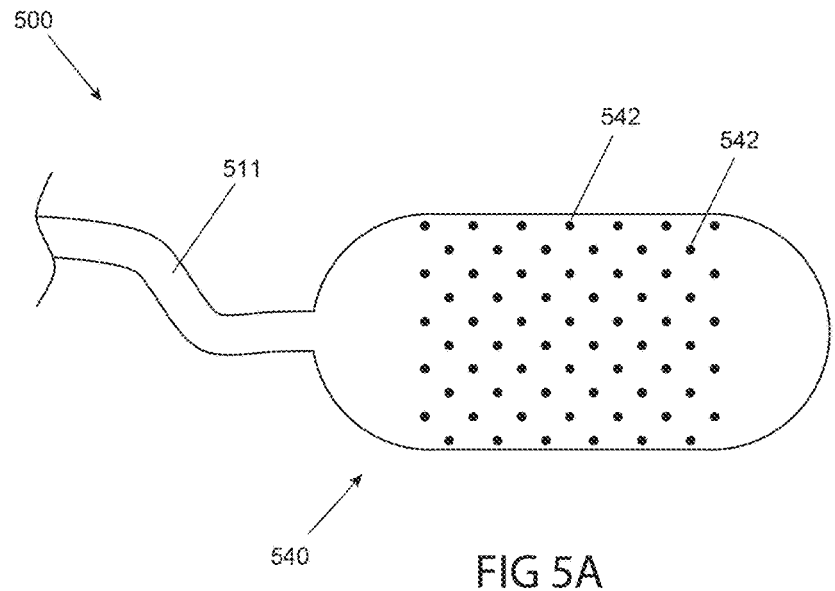
FIGS. 5A and 5B are side and side sectional views of the distal portion of a light-energy delivering tissue treatment device, consistent with the present inventive concepts.
Figure 5B:
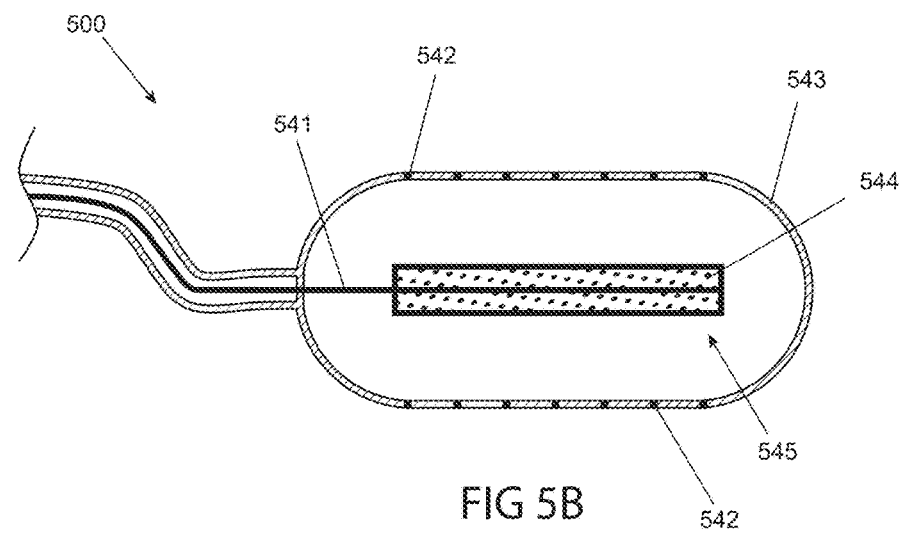

In some embodiments, a relatively small proportion of an energy delivery zone receives energy from a tissue treatment element, such as is specifically described in reference to treatment device 500 of FIGS. 5A and 5B described herebelow. In this "fractional" approach, small portions of the entire surface of one or more energy delivery zones receive energy, such as light energy or electromagnetic energy (e.g. RF energy). In some embodiments, the portions of the tissue surfaces receiving energy can be sufficiently small such that the total amount of heat generated is minimal. One advantage of this fractional method is to reduce adverse effects of one or more overlapping treatments (e.g. reduce likelihood of damage to non-target tissue), such as to alleviate the requirement of precise positioning of a delivery element or otherwise reduce the precision required in energy delivery. In some embodiments, the energy delivery zone is between 1 $cm^2$ and 5 $cm^2$. The small portions of a tissue surface receiving energy result in multiple treated target tissue segments that each includes an inward facing surface relatively positioned on the tissue surface receiving the energy. Non-target or other tissue not receiving energy can be positioned between the multiple treated target tissue segments. These treated target tissue segments extend into the tissue, such as deeper into the wall of tubular tissue such as deeper through a mucosal layer and at least partially into a submucosal layer. In some embodiments, the target tissue segments inward facing surfaces collectively comprise a quantity of 50 to 3000 per square centimeter of tissue surface receive energy, such as approximately a quantity of 500 per square centimeter. The target tissue inward facing surfaces can each comprise a surface with an equivalent diameter of between 20 and 200 microns (i.e. a surface whose area is equivalent to a circle with a diameter between 20 and 200 microns). The target tissue inward facing portions positioned within an energy delivery zone can be treated sequentially, such as a sequential energy delivery by a scanning light delivery element and/or sequentially activated electrodes delivery RF energy. Alternatively or additionally, multiple target tissue inward facing portions positioned within an energy delivery zone can be treated simultaneously, such as via a light source that delivers multiple rays of light to a tissue surface simultaneously (e.g. as described in reference to FIG. 5 herebelow), or an array of micro-electrodes that delivers monopolar energy to small portions of tissue simultaneously. A set of energy delivery zones can each comprise an axial length of between 0.5 and 3 cm in length. A tissue treatment element can be translated between energy deliveries, such as a translation of approximately between 0.5 cm and 3 cm, such as to allow a slight overlap between any two energy delivery zones, such as to cause a mating of boundaries of any two energy delivery zones and/or such as to provide a gap between any two energy delivery zones.

In this fractional approach, the ratio of energy delivery zone tissue receiving energy to energy delivery zone tissue not receiving energy can between 0.1% and 90%, such as less than 50%, less than 20%, less than 10%, less than 5%, less than 2% or less than 1%. The target tissue segment inward facing surfaces can comprise a major axis of less than or equal to 100 microns. The target tissue can be exposed to a temperature greater than or equal to 60° C., between 60° C. and 80° C., or a temperature greater than or equal to 100° C. In some embodiments, at least a portion of the target tissue is vaporized. Energy delivered to the energy delivery zones in this fractional approach can comprise energy selected from the group consisting of: RF; ultrasound; laser light; non-laser light such as non-laser light from an LED; chemical; and combinations of these. In some embodiments, the fractional approach energy delivered is laser or other light energy, such as light energy delivered element by a rotating element as is described in reference to FIG. 5 herebelow. In some embodiments, the fractional approach energy delivery comprises RF energy delivery, such as monopolar or bipolar RF energy delivery from an array of electrodes as described in reference to FIG. 3 herebelow. In some embodiments, the fractional approach involves expanding one or more layers of tissue, as described herein. In these embodiments, the tissue can be expanding with a fluid comprising an injectable non-energy absorbing material. Alternatively or additionally, fluid can be expanded with an injectable energy absorbing material, such as water or saline.

The method of FIG. 1 can be accomplished with a tissue treatment system or device, such as system 10 or one or more components or assemblies of system 10 described herebelow in reference to FIG. 3. The tissue geometry measurement procedures of STEP 41, the tissue expansion procedures of STEP 42, the tissue treatment procedures of STEP 43 and/or another portion of the method of FIG. 1 can be performed with one or more components or assemblies of system 10 of FIG. 3. In some embodiments, the method of FIG. 1 is performed while controlling one or more system parameters, such as a system parameter selected from the group consisting of: a priming procedure parameter such as priming temperature or priming duration; target tissue treatment parameter such as target tissue temperature or target tissue treatment duration; fluid flow rate such as treatment fluid flow rate; a pressure parameter such as a treatment element pressure maintained during treatment of target tissue; a treatment element diameter such as a treatment element diameter maintained during treatment of target tissue; and combinations of these. One or more tissue treatment elements can be varied or otherwise controlled during the method of the present inventive concepts. In some embodiments, a controlled tissue treatment element parameter comprises a parameter selected from the group consisting of: thermal dose delivered; priming temperature; tissue treatment temperature; fluid flow rate; pumping pressure; vacuum pressure; tissue treatment time; and combinations of these. In some embodiments, the diameter of an expandable tissue treatment element such as a balloon is controlled. In these embodiments, a balloon characteristic such as balloon diameter versus pressure is selected in STEP 30.

In some embodiments, the tissue treatment element of the method of FIG. 1 provides an ablative treatment to the energy delivery zone and/or the target tissue, such as an ablative treatment selected from the group consisting of: delivery of thermal energy from a balloon filled with fluid at an ablative temperature; RF energy ablation; delivery of an ablative fluid directly to tissue; cryoablation; delivery of laser energy; delivery of sound energy such as subsonic sound energy or ultrasonic sound energy; plasma energy delivery; argon plasma coagulation; microwave energy delivery; delivery of non-laser light energy; and combinations of these. Alternatively or additionally, the tissue treatment element can be constructed and arranged to provide a non-ablative energy treatment to the energy delivery zone and/or the target tissue, such as a non-ablative energy treatment selected from the group consisting of: mechanical removal of mucosal tissue; chemical, sclerosant or pharmaceutical injection into the submucosa; radioactive seed deposition; chemical spray such as an acid spray; pharmacologic administration such as drug delivery via an agent-eluting balloon; and combinations of these. In some embodiments, a non-ablative tissue treatment element comprises a cutter or other element constructed and arranged to resect tissue, such as to resect plicae tissue, mucosal tissue and/or submucosal tissue of the duodenum and/or the jejunum. For example, a non-ablative treatment element can be configured to resect peaks of the plicae including much of the mucosa, such as to leave a thin layer of submucosa on which new mucosa could grow.

As described above, a tissue treatment element and or tissue treatment system, such as those described in reference to FIG. 3 herebelow, can treat target tissue in multiple tissue treatment steps. The multiple tissue treatment steps can comprise one or more of: multiple sequential deliveries of energy to tissue; multiple sequential deliveries of ablative fluid to tissue; multiple sequential mechanical abrasions or mechanical cutting of tissue; and one or more expansions of one or more layers of tissue.

In some embodiments, target tissue is treated with a series of energy deliveries to each energy delivery zone, after which a relatively uniform advancement of the tissue treatment element is made, such as to sequentially treat relatively continuous (e.g. side-by-side) energy delivery zones. Alternatively, non-bordering energy delivery zones can be treated with sequential deliveries, such as to avoid heating of tissue in a particular anatomical location, each as described in reference to FIGS. 4 and 6 herebelow.

The method of the FIG. 1 is constructed and arranged to cause a luminal surface area reduction in at least a portion of GI tract. In some embodiments, the surface area reduction occurs at least one day after delivery of energy to the energy delivery zone, or at least one week or one month after the delivery of energy to the energy delivery zone. In some embodiments, the surface area reduction occurs in less than a day after treatment, such as a fractional treatment using laser or RF energy delivered to an energy delivery zone. For example, ablative removal of tissue in one or more divots, valleys and/or folds causes the tissue surrounding the removed tissue to simply close up, bringing the edges together and thus reducing the surface area. The surface area reduction of the present inventive concepts can comprise a reduction in a GI tissue characteristic selected from the group consisting of: average height of mucosal folds; surface area of mucosal folds; number of mucosal folds; and combinations of these. In some embodiments, the target tissue treatment reshapes mucosal tissue, such as a flattening of mucosal tissue or other mucosal tissue change that can occur at least 7 days after treatment of the target tissue. In some embodiments, the target tissue treatment results in a reduction in the average villi length in a portion of the GI tract and/or a reduction in the number of villi in a portion of the GI tract.

In some embodiments, the target tissue treatment reshapes and/or reduces the volume of submucosal tissue. In these embodiments, one or more of the following submucosal tissue changes can after the treatment; flattening of the submucosal tissue; increased uniformity of thickness; increased averaged minimum thickness; reduced volume of submucosal tissue; and combinations thereof. In some embodiments, submucosal tissue can be vaporized and/or the delivery of energy to an energy delivery zone can cause coagulation necrosis where the tissue is resorbed through normal healing process. Target tissue treatment can cause a healing response in tissue that results in a reduced amount of mucosal tissue (e.g. in that portion of the GI tract). The submucosal tissue modification can be a result of a target tissue treatment including controlled thermal heating, such as controlled thermal heating by a tissue treatment element constructed and arranged to shrink and/or denature collagen in a submucosal or other tissue layer. In some embodiments, one or more submucosal tissue modifications can occur at least 7 days after the target tissue treatment is performed.

In some embodiments, the target tissue treatment results in one or more of: a smoother surface in a portion of the GI tract; a reduced number of plicae circulares in a portion of the GI tract; or a reduction in the luminal surface area in a portion of the GI tract. In some embodiments, the target tissue treatment results in a modification or other treatment of stem cells, such as to remove and/or ablate one or more of mucosal stem cells and/or epithelial stem cells. In some embodiments, the target tissue treatment results in a reduction in the number of the number of enteroendocrine cells and/or absorptive cells in a portion of the GI tract.

The luminal surface area reduction of one or more portions of the GI tract can occur at a time at least 7 days after treatment of the target tissue, such as when the surface area reduction initiates at a time during target tissue treatment or any time thereafter. In some embodiments, the surface area reduction is occurring at least 3 weeks or at least 6 weeks after target tissue treatment. The method of the present inventive concepts can be constructed and arranged such that the reduced luminal surface area of one or more portions of the GI tract lasts for at least 3 weeks, or at least 6 weeks. Alternatively or additionally, the method of the present inventive concepts can be constructed and arranged to provide a therapeutic benefit to the patient that lasts for at least 6 weeks, or at least 6 months, or at least 2 years. In some embodiments, a second target tissue treatment (e.g. a second clinical procedure as described herein performed at least 6 weeks after the first clinical procedure) is performed to extend the longevity of the surface area reduction and/or the therapeutic benefit achieved via the surface area reduction.

The luminal surface area reduction of one or more portions of the GI tract can include a reduction in luminal surface area of one or more portions of the duodenum and/or jejunum. The reduced surface area of the duodenum and/or jejunum can comprise at least 5%, at least 10%, at least 20%, at least 50% or at least 90%, of the surface area of the duodenum and/or jejunum, respectively.

In some embodiments, STEP 30 includes selecting from a kit of treatment elements, such as selecting from a kit of treatment devices described in reference to FIG. 3 herebelow. The selection can include selecting a size of a treatment element, such as the diameter of a treatment element. Alternatively or additionally, a treatment element size can be varied or otherwise controlled, such as in one or more of STEPs 40. In some embodiments, a treatment element is selected and/or controlled to be within a diameter between 10 mm and 40 mm, such as between a diameter between 15 mm and 32 mm. In some embodiments, a treatment element is deflected during the clinical procedure, such as deflection of a catheter shaft including the treatment element, such as via one or more pull wires. In some embodiments, a treatment element is rotated, such as a rotation that is performed prior to, during and/or subsequent to energy delivery to the energy delivery zone by the treatment element. The selected treatment element can comprise one or more expandable elements, such as an element constructed and arranged to expand to a diameter between 10 mm and 40 mm, or between 15 mm and 32 mm, or between 19.0 mm and 27.5 mm. Expandable treatment elements can include but are not limited to an element selected from the group consisting of: balloon; expandable cage; radially deployable arm; and combinations of these.

The one or more treatment elements used to treat target tissue in STEP 43 can have one or more of numerous forms such as those described in reference to FIG. 3 herebelow. A treatment element can comprise an energy delivery element such as a hot fluid balloon, an RF energy delivery element, an ultrasound energy delivery element, a laser or other light energy delivery element, or combinations of these. A treatment element can be configured to ablate tissue such a hot fluid balloon constructed and arranged to receive fluid at a temperature greater than or equal to 90° C., and then treat target tissue as the temperature decreases to a temperature greater than 70° C. during the course of treatment. In some embodiments, a bolus of heated fluid is provided to a treatment element balloon. Alternatively, a recirculating fluid can be provided to a treatment element balloon. An RF energy delivery element can include an expandable element such as an expandable cage or expandable balloon comprising one or more electrodes constructed and arranged to deliver monopolar and/or bipolar energy to tissue. A treatment element can comprise a tissue cutting element, such as a cutter configured to cut tissue during advancement and/or retraction of the cutting element. The cutting treatment element can further comprising a grasper, such as to perform a grasp and cut tissue cutting procedure.

The one or more treatment elements used to treat target tissue in STEP 43 can be positioned on an elongate shaft, such as an elongate shaft that passes within a working channel of an endoscope or passes alongside an endoscope. The elongate shaft can be advanced over a guidewire.

The method of FIG. 1 can include locating or otherwise identifying one or more anatomical locations such as an anatomical location where energy from the tissue treatment element can be reduced or avoided. In some embodiments, one or more anatomical locations identified include the ampulla of Vater or the pylorus. In some embodiments, a system for treating the target tissue includes a visualization element, such is described in reference to system 10 of FIG. 3 herebelow. Tissue can be treated based on an image produced by the visualization element, such as a visible light or other camera. The system can further include a tissue protection element, also as described in reference to FIG. 3. In some embodiments, tissue is protected with a tissue protection element comprising at least one of a thermal barrier and/or a spacer. The tissue protection element can protect tissue such as the ampulla of Vater. The tissue protection element can be deployed before one or more segments are target tissue as treated, such as one or more tissue segments proximate the ampulla of Vater. The tissue protection element can be deployed prior to the treatment of any target tissue. In some embodiments, a tissue protection element is removed from the patient, such as during or after the treatment of one or more segments of target tissue. Alternatively or additionally, a tissue protection element can be constructed and arranged to be evacuated by the patient's GI system.

Referring now to FIG. 1A, a perspective view of a tissue surface and an energy delivery zone is illustrated, consistent with the present inventive concepts. Tissue surface S1 is shown as a flat surface for illustrative clarity, however tissue surface S1 can comprise a relatively flat and/or multi-dimensional tissue surface, such as an inner (full or partial) circumferential surface of the esophagus, duodenum, jejunum, ileum and/or colon. Tissue surface S1 can comprise tissue of the mouth or stomach, or any location of the GI tract or other anatomical location. Positioned on surface S1 is an energy delivery zone EDZ1. At least a portion of energy delivery zone EDZ1 has been selected for receiving energy to treat target tissue, such as is described in STEP 20 or another step of the method of FIG. 1 described hereabove. Energy delivery zone EDZ1 can receive energy in a single energy delivery or multiple energy deliveries. Energy delivery zone EDZ1 can be one of multiple energy delivery zones treated in one or more clinical procedures to treat a patient disease or disorder as described herein.

Figure 1B:
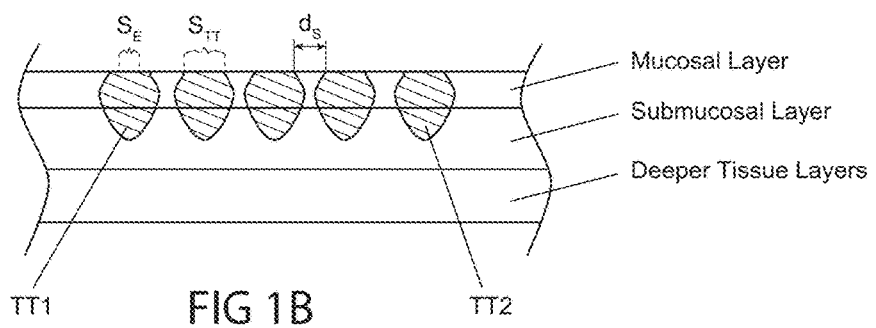
FIG. 1B is a side sectional view of a portion of the energy treatment zone of FIG. 1A, after energy has been delivered to target tissue; consistent with the present inventive concepts.

Energy can be delivered to a continuous surface, or to multiple discrete surfaces, such as surfaces $S_E$ as shown. Surfaces $S_E$ are shown not to scale (neither size nor relative positioning) for illustrative clarity. In some embodiments, the majority (e.g. greater than 50% or greater than 70% or greater than 90%) of energy delivery zone EDZ1 receives energy. In other embodiments, a small proportion of energy delivery zone EDZ1 receives energy, such as with a fractional energy delivery provided to less than 50% of the area of energy delivery zone EDZ1, such as less than 20%, less than 10%, less than 5%, or less than 2% of the area of EDZ1. In some embodiments, a fractional energy delivery is provided to less than 1% of the area of EDZ1. In some embodiments, a fractional energy delivery is delivered to one or more axial segments of GI tissue in multiple passes (e.g. a first one or more energy deliveries to an axial segment of GI tissue followed by a second one or more energy deliveries to a similar axial segment of GI tissue). Referring additionally to FIG. 1B, a side sectional view of a portion of the energy treatment zone EDZ1 of FIG. 1A along line A-A is illustrated. Energy delivered to surfaces $S_E$ result in the creation of multiple treated target tissue volumes TT1, which each have a proximal surface $S_{TT}$. Each treated target tissue TT1 extends through the mucosal layer of the tubular tissue, and at least partially into the submucosal layer while avoiding damage to deeper layers. Due to heat conduction, the area of each surface $S_{TT}$ is greater than the area of each corresponding surface $S_E$. Surfaces $S_{TT}$ are separated by a distance $d_S$ of non-treated tissue. In some embodiments, $d_S$ is approximately zero, such that surfaces $S_T$ share a common boundary. In some embodiments, a fractional energy delivery is used such that $d_S$ is greater than zero (e.g. $d_S$ can be larger than a width of surface $S_{TT}$) and the cumulative surface areas of $S_{TT}$ within energy delivery zone EDZ1 represent less than 50% of the area of energy delivery zone EDZ1, such as less than 20%, less than 10%, less than 5%, less than 2% or less than 1% of the area of EDZ1.

Figure 1C:
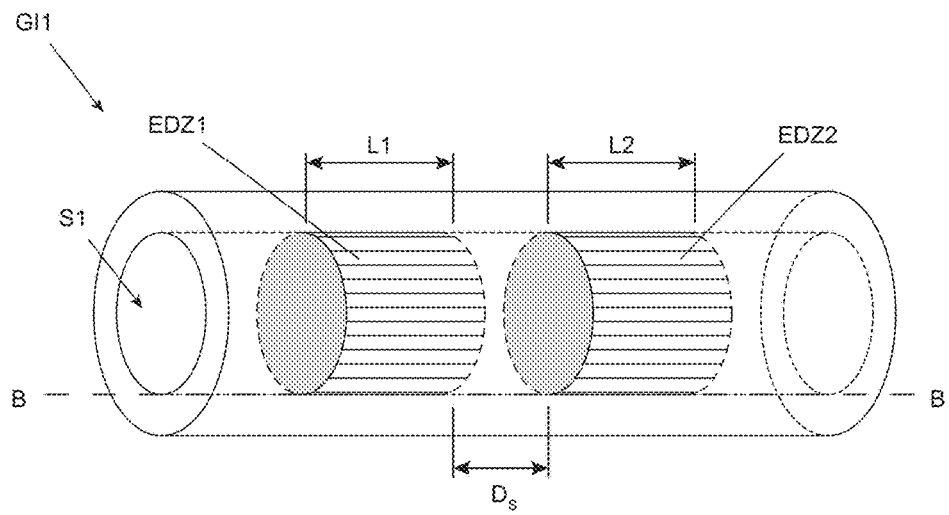
FIG. 1C is a perspective view of a tubular segment of gastrointestinal tissue including two energy delivery zones positioned in the lumen of the tubular segment, consistent with the present inventive concepts.

Referring now to FIG. 1C, a perspective view of a tubular segment of GI tissue is illustrated, including two energy delivery zones positioned in the lumen of the tubular segment, consistent with the present inventive concepts. A tubular segment of GI tissue, tubular segment GI1 includes a lumen with a surface S1. Positioned on surface S1 are two energy delivery zones, EDZ1 and EDZ2 which each comprise a full circumferential segment of tissue surface with lengths L1 and L2 respectively. In some embodiments, EDZ1 and/or EDZ2 comprise partial circumferential surface portions of tubular segment GI1. In some embodiments, EDZ1 and/or EDZ2 comprise a length (L1 and L2 respectively) between 0.5 cm and 3.0 cm. In some embodiments, EDZ1 and EDZ2 are separated (e.g. axially separated) by a separation distance $D_S$, such as a distance less than or equal to 1 cm, or less than or equal to 0.5 cm. In some embodiments, separation distance $D_S$ equals approximately zero, such that zones EDZ1 and EDZ2 approximately share a common boundary. In other embodiments, energy delivery zones EDZ1 and EDZ2 overlap.

At least a portion of energy delivery zones EDZ1 and EDZ2 have been selected for receiving energy to treat target tissue, such as is described in STEP 20 or another step of the method of FIG. 1 described hereabove. Energy delivery zones EDZ1 and/or EDZ2 can receive energy in a single energy delivery or multiple energy deliveries. Energy delivery zones EDZ1 and EDZ2 can be two of multiple energy delivery zones treated in one or more clinical procedures to treat a patient disease or disorder as described herein.

Figure 1D:
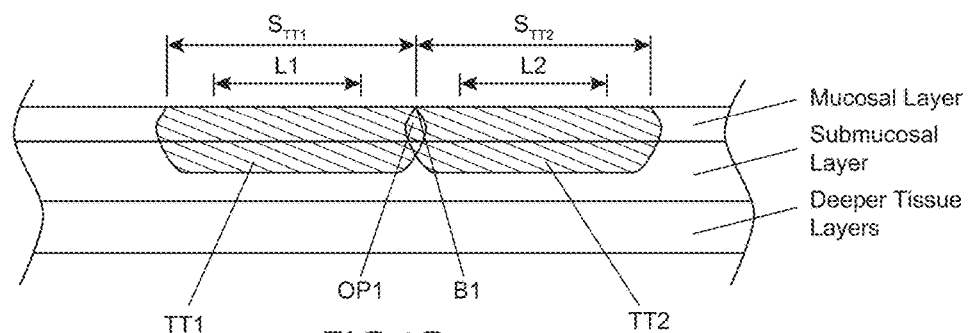
FIG. 1D is a side sectional view of a portion of the two energy delivery zones of FIG. 1C, after a high surface area proportion energy delivery has been delivered to target tissue; consistent with the present inventive concepts.

In some embodiments, a high proportion (e.g. greater than 50%) of energy delivery zone EDZ1 and/or EDZ2 receives energy, such as is shown and described in reference to FIG. 1D herebelow. In other embodiments, a low proportion (e.g. less than 50%) of energy delivery zone EDZ1 and/or EDZ2 receives energy, such as is shown and described in reference to FIG. 1E herebelow.

Referring now to FIG. 1D, a side sectional view of tissue including the two energy delivery zones of FIG. 1C is illustrated, after a high surface area proportion energy delivery has been delivered to target tissue; consistent with the present inventive concepts. FIG. 1D depicts a sectional view of tubular segment GI1 along line B-B of FIG. 1C. A high proportion of energy delivery zones EDZ1 and EDZ2 have received energy, such as approximately 100% of EDZ1 and EDZ2, such as that the entire length L1 and circumference of EDZ1 and EDZ2 has received energy, treating target tissue TT1 and TT2 respectively. In some embodiments, one or more hot fluid filled balloons (as are described herein) is brought into contact with EDZ1 and EDZ2 (simultaneously or sequentially), such as to transfer heat to the majority of EDZ1 and EDZ2. Target tissue TT1 and TT2 comprise a relatively full circumferential (e.g. 360°) volume of target tissue with surface area $S_{TT1}$ and $S_{TT2}$ as shown. Surface areas $S_{TT1}$ and $S_{TT2}$ can have a length greater than the corresponding energy delivery zones lengths, L1 and L2 respectively, due to the conduction of heat in the tissue. The treated target tissue TT1 and TT2 can extend through the mucosal layer, and partially into the submucosal layer as shown, avoiding damage to deeper tissue layers. In some embodiments, surface areas $S_{TT1}$ and $S_{TT2}$ share a common boundary B1 as shown in FIG. 1D (e.g. separation distance $D_S$ of FIG. 1C is equal to zero). In some embodiments, target tissue TT1 and TT2 can have overlapping portions, such as overlapping portion OP1 as shown.

Figure 1E:
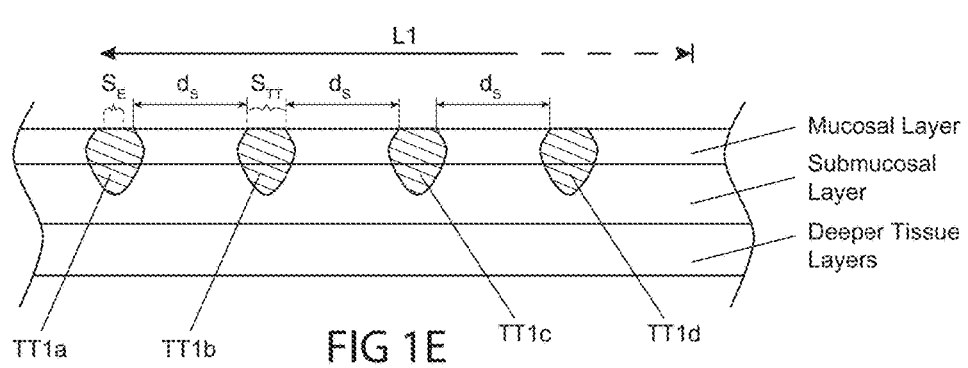
FIG. 1E is a side sectional view of a portion of a first energy delivery zone of FIG. 1C, after a low surface area proportion energy delivery has been delivered to target tissue; consistent with the present inventive concepts.

Referring now to FIG. 1E. a side sectional view of tissue including a portion of a first energy delivery zone of FIG. 1C is illustrated, after a low surface area proportion energy delivery has been delivered to target tissue; consistent with the present inventive concepts. FIG. 1E depicts a sectional view of tubular segment GI1 along line B-B of FIG. 1C. A low proportion of energy delivery zone EDZ1 has received energy, such as less than 50% of EDZ1, such as less than 20%, less than 10%, less than 5%, less than 2% or less than 1% of EDZ1. In some embodiments, a fractional approach is used to achieve a low surface area proportion energy delivery. Fractional energy delivery can be performed with laser or other light energy as described in reference to FIG. 5 hereinbelow, or any other fractional energy delivery approach such as those described herein. In the fractional energy delivery approach, multiple, relatively small volumes of tissue are treated, such as target tissue segments TT1a, TT1b, TT1c and TT1d (collectively TT1) shown in FIG. 1E. Each target tissue segment TT1 includes an inwardly facing surface $S_{TT}$. Each surface $S_{TT}$ includes a sub-portion that received energy (e.g. light energy), surface $S_E$.

Each target tissue segment TT1 can be separated from another target tissue segment by non-treated tissue with a length $d_s$. In some embodiments, arrays of target tissue segments TT1 are separated by similar distances, such as in a symmetrical pattern that covers a full circumferential segment of energy delivery zone EDZ1. In other embodiments, two or more target tissue segments TT1 are separated by different distances (i.e. different lengths $d_s$ of non-treated tissue). In some embodiments, energy delivery zone EDZ1 comprises between 50 and 3000 target tissue segments TT1 per cm², such as approximately 500 target tissue segments TT1 per cm². In some embodiments, multiple surfaces $S_{TT}$ comprise an equivalent diameter between 20 microns and 200 microns. In some embodiments, multiple surfaces $S_{TT}$ comprise a major axis less than or equal to 100 microns.

The treated target tissue segments TT1 can extend through the mucosal layer, and partially into the submucosal layer as shown, avoiding damage to deeper tissue layers.

Figure 2A:
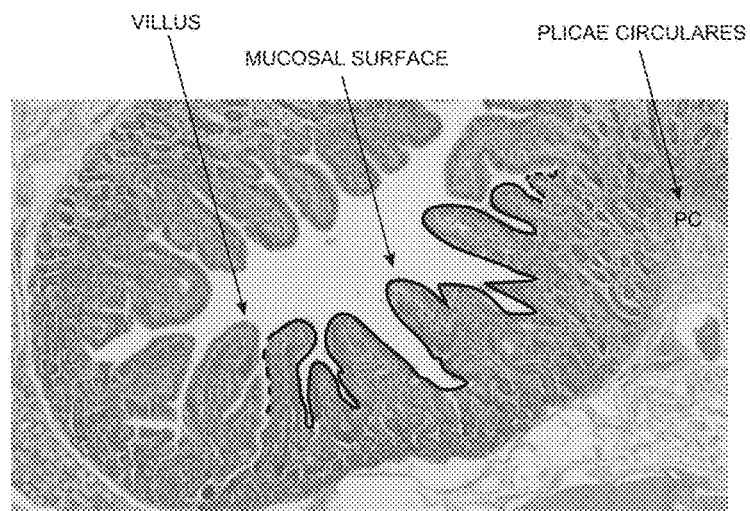
FIG. 2A is a photograph of a cross section of mammalian duodenal tissue prior to a target tissue treatment, consistent with the present inventive concepts.

Referring now to FIG. 2A, a photograph of a cross section of mammalian duodenal tissue prior to any target tissue treatment is illustrated. The native small intestinal mucosal surface has a complex structure that has evolutionarily adapted to maximize the surface area available for contact with the nutrient stream and environment of the GI tract. This complex structure is comprised of plicae circulares (invaginations of submucosa and mucosa that create gross surface irregularity to the intestinal mucosal surface). Microscopically, the mucosal layer also contains villi, comprised by the absorptive and secretory cells of the mucosa, as well as connective tissue, nerves, vasculature, and lymph. Within each cell of the mucosa, there are additionally microvilli (not visible), also known as the "brush border," which further enhances the mucosal surface area.

Figure 2B:
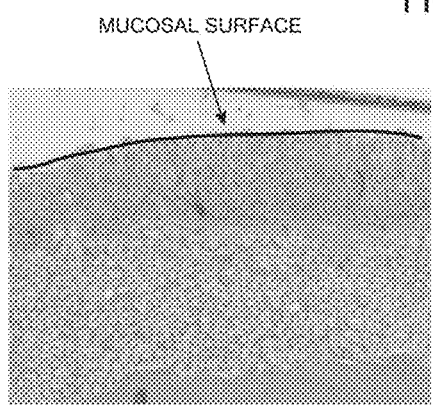
FIGS. 2B and 2C are photographs of cross sections of mammalian duodenal tissue subsequent to a target tissue treatment, consistent with the present inventive concepts.
Figure 2C:
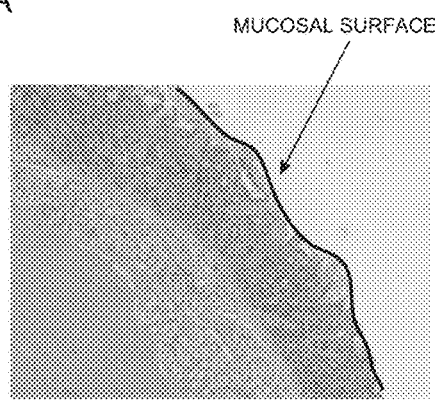

FIGS. 2B and 2C illustrate a cross section of mammalian duodenal tissue subsequent to a target tissue treatment, consistent with the present inventive concepts. Images shown refer to histologic specimens of mammalian tissue after 42 days follow up from the target tissue treatment of the present inventive concepts. Unlike in FIG. 2A, illustrated are elimination of the submucosa/mucosal invaginations, plicae circulares, as well as blunting of the villi and architectural distortion consistent with failure to completely reconstitute the native villus structure. These changes are seen even after inflammation has subsided and the healing process has completed. The consequence of these changes is a durable and dramatic reduction in the amount of mucosal surface available for interaction with the nutrient stream and GI lumen environment. The treatment described in the present inventive concepts has empirically been demonstrated to create a durable alteration to the mucosal surface after healing without deleterious damage to underlying muscularis propria tissue.

Referring now to FIG. 3, a schematic view of a system for ablating or otherwise treating target tissue is illustrated, consistent with the present inventive concepts. System 10 is configured to treat target tissue TT, such as to treat one or more patient diseases or disorders selected from the group consisting of: diabetes; obesity or otherwise being overweight; hypercholesterolemia; exercise intolerance; psoriasis; and combinations of these. In the embodiment of FIG. 3, target tissue TT includes one or more tissue segments within a body lumen of a mammalian patient as has been described hereabove. In some embodiments, target tissue TT comprises a continuous or discontinuous circumferential segment of a duodenum, such as a volume of tissue comprising at least 50% of the duodenal mucosa, or at least 67% of the duodenal mucosa. In some embodiments, target tissue TT comprises a treatment portion comprising duodenal mucosal tissue and a safety-margin portion comprising at least an innermost layer of the duodenal submucosa. System 10 can be configured to treat the duodenal mucosa while avoiding damage to duodenal adventitial tissue, such as by avoiding damage to tissue beyond the mucosa, to tissue beyond the superficial submucosa and/or to tissue beyond the deep submucosa.

System 10 can include one or more tissue treatment devices, such as first treatment device 100 and second treatment device 100'. First treatment device 100 can be used in a first clinical procedure including treatment of target tissue, and second treatment device 100' can be used in a second clinical procedure including treatment of target tissue, as is described hereabove. In some embodiments, the second clinical procedure is performed at least twenty-four hours after the first clinical procedure. Target tissue treatments performed in the second clinical procedure can be constructed and arranged based on one or more outcomes of the first clinical procedure, also as is described hereabove. Additional treatment devices can be included, such as to perform a third or other subsequent clinical procedures including target tissue treatments.

First treatment device 100 and second treatment device 100' can be similar or dissimilar treatment devices, and can be constructed and arranged to perform similar or dissimilar treatments to similar or dissimilar volumes of tissue. Differences between first treatment device 100 and second treatment device 100' can include but are not limited to: type of ablative treatment provided such as type of energy delivered; type of non-ablative treatment provided; configuration of a treatment assembly or a treatment element included such as configuration of a treatment assembly or a treatment element included in the treatment device; length of the device; diameter of a portion of the device; and combinations of these. In some embodiments, first treatment device 100 comprises a first treatment element constructed and arranged to deliver a different form of energy than a second treatment element of second treatment device 100'. Alternatively or additionally, first treatment device 100 can comprise a first treatment element with a different geometry (e.g. different diameter, length and/or tissue contact surface area or shape), than a second treatment element of second treatment device 100'.

In some embodiments, system 10 can be constructed and arranged as is described in applicant's co-pending U.S. patent application Ser. No. 13/945,138, entitled "Devices and Methods for the Treatment of Tissue", filed Jan. 18, 2013, the contents of which is incorporated by reference in its entirety. In some embodiments, first treatment device 100 and/or second treatment device 100' can be constructed and arranged to ablate tissue, such as with an ablation treatment selected from the group consisting of: delivery of thermal energy from a balloon filled with fluid at an ablative temperature; RF energy ablation such as monopolar and/or bipolar RF energy ablation; delivery of an ablative fluid directly to tissue; cryoablation; delivery of laser energy; delivery of sound energy such as subsonic sound energy or ultrasonic sound energy; plasma energy delivery; argon plasma coagulation; microwave energy delivery; delivery of non-laser light energy; and combinations of these. In some embodiments, first treatment device 100 and/or second treatment device 100' can be constructed and arranged to perform a non-ablative treatment of target tissue, such as with a non-ablative treatment selected from the group consisting of: mechanical removal of mucosal tissue; chemical, sclerosant or pharmaceutical injection into the submucosa; radioactive seed deposition; chemical spray such as an acid spray; pharmacologic administration such as drug delivery via an agent-eluting balloon; and combinations of these. First treatment device 100 and/or second treatment device can be configured to resect tissue, such as to resect tissue selected from the group consisting of: plicae tissue; mucosal tissue; submucosal tissue; and combinations of these.

System 10 can include one or more body introduction devices, such as endoscope 350. Endoscope 350 can comprise a standard GI endoscope such as an endoscope with one or more working channels configured to slidingly receive first treatment device 100 (as shown) and/or second treatment device 100'.

System 10 can include energy delivery unit (EDU) 330, which can be operably attached to first treatment device 100 (as shown) and/or second treatment device 100'. EDU 330 can be configured to provide numerous forms of energy to one or more treatment elements of first treatment device 100 and/or second treatment device 100', such as an energy form selected from the group consisting of: RF energy; microwave energy; laser energy; sound energy such as subsonic sound energy or ultrasound energy; chemical energy; thermal energy such as heat energy or cryogenic energy; and combinations of these.

System 10 can include pumping assembly 340 which can provide and/or remove one or more fluids from one or more devices of system 10, such as first treatment device 100, second treatment device 100' and/or endoscope 350. Pumping assembly 340 can include one or more fluid reservoirs, such as fluid reservoir 341 shown, and/or it can receive or supply fluids to EDU 330. In some embodiments, pumping assembly 340 and/or EDU 330 recirculate one or more fluids through a device of system 10, such as to recirculate fluid through first treatment device 100, second treatment device 100' and/or endoscope 350.

System 10 can include motion transfer assembly 320, which can be constructed and arranged to rotate, translate and/or otherwise move one or more devices, assemblies and/or components of system 10, as is described in detail herebelow.

System 10 can include controller 310, comprising one or more algorithms 311, which can be constructed and arranged to automatically and/or manually control and/or monitor one or more devices, assemblies and/or components of system 10, as is described in detail herebelow.

Ablation device 100 comprises a tissue treatment assembly, treatment assembly 140. Treatment assembly 140 includes one or more elements constructed and arranged to ablate or otherwise treat target tissue, such as treatment element 145 shown. Treatment element 145 can comprise one or more elements selected from the group consisting of: an electrical energy delivery element such as one or more electrodes constructed and arranged to deliver RF energy; a fluid delivery element such as a nozzle or permeable surface constructed and arranged to deliver ablative fluid directly to target tissue TT; a balloon such as a balloon constructed and arranged to receive an ablative fluid and deliver hot or cold thermal energy to ablate target tissue TT; a laser energy delivery element such as an optical fiber, a focusing lens and/or other optical component; a sound energy delivery element such as a piezo-based element configured to deliver ultrasonic and/or subsonic energy; a tissue abrading element; and combinations of these. Treatment element 145 can be positioned on, in, within and/or passing through one or more components of treatment assembly 140, such as a balloon, cage, spline or other component as are described in detail herein. In some embodiments, treatment assembly 140 and treatment element 145 are the same component, such as when treatment assembly 140 comprises a balloon constructed and arranged to receive hot or cold ablative fluid to treat target tissue. Treatment assembly 140 can comprise an energy distribution element, such as one or more optical components configured to rotate, translate and/or otherwise distribute laser or other light energy to target tissue. In some embodiments, treatment assembly 140 and/or treatment element 145 comprise an energy distribution element including a rotating element such a rotating mirror; a rotating prism and/or a rotating diffractive optic. In some embodiments, ablation device 100 comprises one or more fibers that deliver laser or other light energy to a treatment element 145 comprising a balloon filled with light-scattering material, such as is described in reference to FIGS. 5A and 5B herebelow.

In some embodiments, first treatment device 100 and/or second treatment device 100' delivers heat or thermal energy to tissue, such as when treatment assembly 140 and/or treatment element 145 comprises a balloon constructed and arranged to be filled with an ablative fluid comprising a hot or cold volume of fluid at a temperature sufficient to ablate tissue when the balloon contacts the tissue. The hot or cold volume of fluid can be provided to treatment assembly 140 and/or treatment element 145 via EDU 330 and/or pumping assembly 340. System 10 can be configured to deliver thermal energy to tissue as is described in applicant's co-pending International Application Serial Number PCT/US2013/28082, entitled "Heat Ablation Systems, Devices and Methods for the Treatment of Tissue", filed Feb. 27, 2013, the contents of which is incorporated herein by reference in its entirety.

In some embodiments, first treatment device 100 and/or second treatment device 100' delivers RF energy to tissue, such as when treatment element 145 comprises one or more electrodes constructed and arranged to receive RF energy provided by EDU 330. In these embodiments, the one or more electrodes can comprise one or more conductive dots positioned on an expandable element such as a balloon. In some embodiments, EDU 330 is configured to deliver RF energy to one or more electrodes of first treatment device 100 and/or second treatment device 100', such as in a monopolar mode through a grounding pad such as ground pad 70 and/or in a bipolar mode between two or more electrodes of first treatment device 100 or second treatment device 100'. System 10 can be configured to deliver RF energy to tissue as is described in applicant's co-pending International PCT Application Serial Number PCT/US2013/052786, entitled "Electrical Energy Ablation Systems, Devices and Methods for the Treatment of Tissue", filed Jul. 30, 2013, the contents of which is incorporated herein by reference in its entirety.

In some embodiments, first treatment device 100 and/or second treatment device 100' delivers ablative fluid directly to tissue, such as when treatment element 145 comprises one or more fluid delivery elements. In these embodiments, treatment element 145 can be constructed and arranged to ablate target tissue TT by delivering ablative fluid provided by EDU 330 and/or pumping assembly 340. Treatment element 145 can include one or more fluid delivery elements selected from the group consisting of: nozzle such as a nozzle configured to deliver a cone or other shaped spray of fluid; opening; hole; slit; permeable membrane; misting element; vaporizer; and combinations of these. Ablative fluid can comprise one or more liquids or gases that are delivered to target tissue TT at a temperature above or below a threshold that would ablate tissue. In some embodiments, the ablative fluid delivered by treatment element 145 comprises steam, such as steam at a temperature of 100° C. or above. In some embodiments, the ablative fluid delivered by treatment element 145 comprises a vaporized fluid at a temperature below 100° C., such as a vaporized fluid at a temperature between 70° C. and 90° C. In some embodiments, the ablative fluid delivered by treatment element 145 comprises a gas, such as a gas between 60° C. and 99° C., such as a gas delivered to tissue at a temperature between 70° C. and 90° C. In some embodiments, the ablative fluid delivered by treatment element 145 comprises a vaporized liquid, such as a vaporized liquid delivered to tissue at a temperature below 100° C., such as at a temperature between 70° C. and 90° C. Alternatively or additionally, an ablative fluid delivered by treatment element 145 can comprise one or more liquids or gases that cause tissue necrosis or otherwise treat target tissue TT as has been described hereabove, using one or more chemically active agents (e.g. ablation not primarily caused by delivery or removal of heat from tissue). In these embodiments, the agent can comprise an agent selected from the group consisting of: sclerotic agent; acid; base; saline; alcohol; carbon dioxide; nitrous oxide; nitrogen; acetic acid; glycerol; and combinations of these. In these embodiments, a counter-acting agent can be included, such as a counter-acting agent delivered by treatment device 100 or another device or component of system 10 that is used to neutralize, impede, reduce and/or limit tissue ablation caused by the delivery of a necrotic agent-based ablative fluid. The counter-acting agent can be delivered by treatment element 145 or another component. The counter-acting agent can comprise an agent selected from the group consisting of: anti-sclerotic agent; base; acid; buffer solution; saline; water; and combinations of these. System 10 can be configured to deliver ablative fluid directly to tissue as is described in applicant's U.S. Provisional Application Ser. No. 61/681,502, entitled "Ablation Systems, Device and Methods for the Treatment of Tissue", filed Aug. 9, 2012, the contents of which are incorporated herein by reference in their entirety.

As shown in FIG. 3, first treatment device 100 includes coaxial shafts 111*a* and 111*b*. Shaft 111*b* has a distal end 112. In some embodiments, distal end 112 includes a bulbous element, ball 113. In these embodiments, ball 113 can be sized to fit through a working channel of endoscope 350, such as when ball 113 has a diameter less than 6 mm or less than 4 mm. Alternatively, ball 113 can have a larger diameter configured to assist in smoothly traversing plicae, such as a diameter of at least 8 mm. Shafts 111*a* and 111*b* are sized and configured such that shaft 111*a* slidingly receives shaft 111*b*, such that they can be advanced and/or retracted in unison or independently. Alternatively, first treatment device 100 can comprise a single shaft. In some embodiments, device 100 comprises a flexible portion (e.g. a portion of shafts 111*a* and 111*b* including distal end 112) with a diameter less than 6 mm. In some embodiments, the flexible portion is configured to pass through a working channel of an endoscope with a diameter of less than or equal to 6.0 mm, 4.2 mm, 3.8 mm, 3.2 mm or 2.8 mm. In some embodiments, device 100 comprises a shaft length of 100 cm or longer, or otherwise comprises a length sufficient to be orally and/or nasally inserted into a patient, and subsequently advanced to reach the esophagus, stomach, duodenum and/or jejunum; and/or rectally inserted into a patient, and subsequently advanced to reach the terminal ileum of that patient. In FIG. 3, shafts 111*a* and 111*b* have been inserted through a working channel (e.g. a 6 mm working channel), lumen 351, of endoscope 350, typically a GI endoscope. Shafts 111*a* and/or 111*b* can be inserted over a standard interventional guidewire, such as guidewire 60 shown exiting distal end 112 of shaft 111*b*. In an alternative embodiment, shafts 111*a* and 111*b* are positioned in a side-by-side configuration, such as to be placed in two separate lumens of endoscope 350 or in two other non-coaxial locations. In some embodiments, one or both of shafts 111*a* or 111*b* passes through a body lumen or other internal body location alongside endoscope 350 (i.e. not through lumen 351, traveling relatively parallel with but external to endoscope 350). Shaft 111*a* and/or 111*b* can include manipulation means configured to deflect and/or steer a distal portion of the shaft, such as via one or more proximal handle controlled pull wires that extend and are attached to the distal portion of the shaft (handle and pull wires not shown but well known to those of skill in the art), such as to deflect and/or steer treatment assembly 140 and/or expandable assembly 130 towards and/or away from tissue and/or assist in navigating treatment assembly 140 through tortuous anatomy.

Treatment assembly 140 can be positioned on shaft 111*a* as shown. A tissue treatment element, treatment element 145 is electrically, fluidly, mechanically and/or otherwise operably connected to conduit 141. Conduit 141 comprises one or more elongate filaments selected from the group consisting of: a wire such as one or more wires configured to deliver electrical or other power and/or transmit electrical or other data signals; an optical fiber such as one or more optical fibers configured to deliver power and/or transmit data signals; a tube such as a fluid delivery tube; a control rod such as an advanceable and/or retractable control rod; and combinations of these. Conduit 141 travels proximally through shaft 111*a* and operably attaches to EDU 330, pumping assembly 340, motion transfer assembly 320 and/or another component, assembly or device of system 10.

In some embodiments, conduit 141 comprises one or more fluid delivery tubes constructed and arranged to deliver and/or recirculate heated or chilled fluid into treatment assembly 140, such as heated or chilled fluid received from EDU 330 and/or pumping assembly 340 and delivered into treatment element 145, such as when treatment element 145 comprises a balloon or other fluid reservoir configured to receive ablative fluid at a temperature sufficient to ablate tissue when treatment element 145 contacts the tissue. Alternatively or additionally, conduit 141 can comprise one or more fluid delivery tubes constructed and arranged to deliver an ablative fluid to treatment assembly 140, such as ablative fluid provided by EDU 330 and/or pumping assembly 340 and delivered directly to target tissue TT by one or more treatment elements 145, such as when treatment element 145 comprises a fluid delivery element such as a nozzle. Conduit 141 can further comprise one or more insulating layers configured to prevent transfer of heat into and/or out of conduit 141. Conduit 141 can include a surrounding lumen which receives a circulating fluid configured to provide an insulating, warming and/or cooling effect on conduit 141 and/or any fluid contained within conduit 141. Conduit 141 and/or another fluid delivery tube of system 10 can comprise one or more elongate hollow tubes, such as a hollow tube positioned within shaft 111*a*. Alternatively, conduit 141 and/or another fluid delivery tube of system 10 can comprise a lumen within a shaft, such as a lumen within shaft 111*a*. In some embodiments, conduit 141 and/or another fluid delivery tube of system 10 comprises both a lumen and a hollow tube, such as when the lumen and hollow tube are fluidly connected in an end-to-end configuration. Conduit 141 typically attaches to EDU 330 and/or pumping assembly 340 with one or more operator attachable fluid connections ports, such as a fluid connection port included in a handle positioned on the proximal end of shaft 111*a*, handle not shown. Conduit 141 can comprise one or more fluid delivery tubes including one or more valves, not shown but such as a duck-bill or other valve used to regulate flow within conduit 141, such as to regulate flow pressure and/or direction.

In some embodiments, conduit 141 comprises one or more elongate filaments constructed and arranged to transmit energy and/or data. Conduit 141 can comprise one or more wires constructed and arranged to deliver RF energy to one or more electrode-type treatment elements 145, such as when the treatment elements 145 are configured to ablate target tissue TT in monopolar and/or bipolar modes as described herein. Conduit 141 can comprise one or more filaments constructed and arranged to deliver laser energy, such as one or more optical fibers constructed and arranged to deliver laser energy to one or more lenses or other optical component-type treatment elements 145, such as to ablate target tissue TT with laser or other light energy. Conduit 141 can comprise one or more wires or other energy transfer filaments constructed and arranged to allow a sound producing-type treatment element to ablate target tissue TT with sound energy such as ultrasonic or subsonic sound energy. Conduit 141 can comprise one or more wires or optical fibers configured to transmit information, such as information received from a sensor of system 10 as described herebelow.

In some embodiments, conduit 141 comprises one or more control rods constructed and arranged to cause one or more treatment elements 145 to rotate and/or translate, such as when conduit 141 is operably attached to motion transfer assembly 320, such as prior to, during and/or after delivery of energy to target tissue. In some embodiments, one or more treatment elements 145 comprise a surface configured to abrade or otherwise disrupt tissue as it is rotated and/or translated by movement of conduit 141. Alternatively or additionally, one or more treatment elements 145 can deliver energy and/or fluid to tissue, and movement of one or more control rods of conduit 141 changes the location of the tissue segment receiving the energy and/or fluid. Motion of one or more treatment elements 145 can be configured to treat a full circumferential (i.e. 360°) segment of tubular tissue, or a partial circumferential (e.g. a 45°-350°) segment of tubular tissue. Motion of one or more treatment elements 145 can be configured to treat a particular axial length of tubular tissue, such as a length comprising at least 25% of the length of the duodenum, or at least 35% of the length of the duodenum, or at least 50% of the length of the duodenum, or at least 66% of the length of the duodenum; or at least 75% of the length of the duodenum.

Treatment assembly 140 can be radially expandable, similar to expandable assembly 130 described herebelow. System 10 can be configured to allow expansion of treatment assembly 140 to cause one or more treatment elements 145 to contact a tissue wall such as a duodenal wall, such as when one or more treatment elements 145 comprise a balloon configured to ablate tissue with a contained hot or cold fluid, or when one or more treatment elements 145 comprise an electrode configured to deliver RF energy to ablate tissue. Treatment assembly 140 can be configured to expand to a diameter less than the diameter of the target tissue TT, such as when a vacuum is applied to cause the target tissue TT diameter to decrease to make contact with one or more treatment elements 145, as has been described hereabove. System 10 can be configured to allow expansion of treatment assembly 140 to cause one or more treatment elements 145 to be positioned at a fixed distance from the luminal wall of tubular tissue, such as a positioning at a fixed distance of at least 250 microns, at least 500 microns, or at least 1 mm from a tissue wall, such as when one or more treatment elements 145 are configured to deliver ablative fluid to the target tissue TT and/or to deliver light energy to the target tissue TT. In addition to treating target tissue TT, treatment assembly 140 and/or one or more treatment elements 145 can be configured in one or more various forms to modify, manipulate, measure and/or diagnose target tissue TT and/or other tubular or non-tubular tissue.

In some embodiments, treatment element 145 can be further configured to extract fluids, such as to extract previously administered ablative fluids and/or insufflation fluids from a body lumen. Fluid extraction can be performed prior to, during and/or after treatment of target tissue TT.

EDU 330 and/or pumping assembly 340 can comprise multiple heat or cold sources used to modify the temperature of one or more fluids provided by and/or passing through EDU 330 and/or pumping assembly 340. The heat or cold sources can be at a fixed temperature or they can be variable. In some embodiments, a first heat or cold source is at a fixed temperature and a second heat or cold source is at a variable temperature.

In some embodiments, a cooling fluid is delivered, prior to, during and/or after the treatment of target tissue TT, such as to precisely control target tissue ablation and avoid ablation of non-target tissue. The cooling fluid can be provided by EDU 330 and/or pumping assembly 340, and it can be delivered to tissue, such as target or non-target tissue, and/or it can be delivered to a component of system 10 such as to reduce the temperature of a component of treatment assembly 140. Treatment element 145 and/or another component of system 10 can be constructed and arranged to deliver the cooling fluid to one or more tissue surfaces, such as a cooling fluid delivered to treatment element 145 via conduit 141 and configured to reduce the temperature of one or more volumes of tissue. The ablation provided by system 10 can comprise a non-desiccating or a desiccating ablation. In some embodiments, a non-desiccating ablation is performed for a first portion of target tissue TT such as in a first tissue treatment, and a desiccating ablation is performed for a second portion of target tissue TT such as in a second tissue treatment. Non-desiccating ablations can be performed to treat over-lapping portions of target tissue TT, and/or to avoid creation of tissue debris if desired. Desiccating ablations can be performed to achieve a higher thermal gradient, to remove excess tissue, and/or to ablate rapidly if desired.

EDU 330 and/or pumping assembly 340 can be configured to deliver a hot fluid to pre-heat one or more components of system 10. In some embodiments, the one or more components include conduit 141; a fluid delivery tube such as a tube within shaft 111a, a fluid delivery lumen such as a lumen within shaft 111a; shaft 111a; treatment element 145; and combinations of these. System 10 can be configured to pre-heat one or more components by circulating or recirculating hot fluid, such as a hot liquid or gas. In some embodiments, treatment assembly 140 contains and/or treatment element 145 delivers a hot fluid, and one or more components of system 10 are pre-treated with a hot gas. Alternatively or additionally, system 10 can comprise one or more insulators surrounding one or more conduits, lumens and/or shafts of treatment device 100 and/or system 10, such as an insulator surrounding conduit 141 and configured to prevent transfer of heat across (e.g. into or out of) conduit 141.

System 10 can be configured to maintain target tissue TT or other tissue below a threshold or within a temperature range, such as in a closed-loop configuration through the use of one or more sensors such as sensor 149 of treatment assembly 140 or sensor 139 of expandable assembly 130, each described in detail herebelow. In some embodiments, tissue temperature is maintained below 100° C., such as between 60° C. and 90° C., such as between 65° C. and 85° C. In some embodiments, system 10 is configured to maintain the temperature of target tissue TT at a setpoint temperature. The setpoint temperature can vary over time. System 10 can be configured to deliver energy at a level that increases and/or decreases over time. In some embodiments, treatment assembly 140 is constructed and arranged to cause the temperature of at least a portion of target tissue TT to rapidly rise to a setpoint (e.g. a setpoint between 60° C. and 75° C.). After the target tissue TT reaches the setpoint temperature, system 10 can deliver energy or otherwise treat the target tissue TT to maintain the setpoint temperature for an extended time period.

In some embodiments, EDU 330 and/or pumping assembly 340 is configured to heat or chill one or more fluids, such as one or more ablative fluids 331 or other fluids. In some embodiments, treatment assembly 140 is configured to heat or chill one or more fluids. Applicable heating and cooling elements include but are not limited to heat exchangers, heating coils, peltier components, refrigeration assemblies, gas expansion coolers, and the like. Heating and cooling can be applied to a source of fluid (e.g. fluid reservoir 341), or to fluid that is withdrawn from device 100 (e.g. a recirculating fluid and/or a body extracted fluid such as recovered, previously delivered, ablative or insufflating fluid). EDU 330 and/or pumping assembly 340 can include one or more pumps configured to deliver and/or extract fluid at a particular flow rate, pressure, or other fluid delivery parameter. System 10 can be configured to deliver fluid at a sufficiently high temperature to ablate target tissue TT, after which a cooling fluid is delivered to removal thermal energy from target tissue TT and/or other tissue, such as cooling fluid delivered for a time period of at least 2 seconds, at least 5 seconds, at least 10 seconds or at least 20 seconds.

In some embodiments, treatment device 100 further includes a radially expandable assembly, expandable assembly 130, mounted to shaft 111b. In some embodiments, treatment device 100 comprises a single shaft, and both treatment assembly 140 and expandable assembly 130 are mounted to that single shaft. Expandable assembly 130 can be configured in one or more various forms to treat, modify, manipulate, measure and/or diagnose target tissue TT and/or other tubular tissue. Expandable assembly 130 can comprise one or more expandable elements 131, such as one or more expandable elements selected from the group consisting of: an inflatable balloon; a radially expandable stent or cage; an array of splines; one or more radially deployable arms; a spiral or other helical structure; a furlable structure such as a furlable sheet; an unfurlable structure such as an unfurlable sheet; a foldable structure such as a foldable sheet; an unfoldable structure such as an unfoldable sheet; and combinations of these. In some embodiments, expandable assembly 130 is inflatable (e.g. an inflatable balloon), and inflation fluid can be delivered into expandable assembly 130 via an inflation tube 136. Inflation tube 136 can comprise a lumen of shaft 111b (or a tube within shaft 111b) that travels proximally through shaft 111b and shaft 111a, such as to receive inflation fluid delivered by pumping assembly 340. Expandable assembly 130 can be positioned distal to treatment assembly 140 as shown in FIG. 3, or alternatively, expandable assembly 130 can be positioned proximal to treatment assembly 140, such as when treatment assembly 140 is mounted to shaft 111b and expandable assembly 130 is mounted to shaft 111a.

Expandable assembly 130 can be configured to seal a body lumen location, such as to create a full or partial occlusive barrier at a location within the duodenum or other location in the GI tract. System 10 can be configured to cause a fluid or other seal comprising an occlusive barrier selected from the group consisting of: a pressure seal; a cryogenically applied seal such as an ice ball seal; a vacuum seal; a full circumferential seal; a partial circumferential seal; and combinations of these. In some embodiments, treatment element 145 treats a portion of target tissue TT located proximal or distal to the occlusive barrier. System 10 can include multiple expandable assemblies configured to seal a body lumen location, such as first expandable assembly which provides a seal at a proximal end of a segment of tubular tissue, and a second expandable assembly which provides a seal at a distal end of the tubular tissue segment. In some embodiments, treatment element 145 treats a portion of target tissue TT located between the two sealed locations, such as between two locations of the duodenum, each duodenal location sealed by an expandable component or assembly of device 100. One or more expandable assemblies can be configured to occlude a first location of a body lumen, followed by subsequent occlusions of one or more different locations within the body lumen. System 10 can be configured to apply a vacuum between two occlusive elements, such as a vacuum applied by one or more treatment elements 145, via one or more functional elements 138 and/or 148 (attached to expandable assembly 130 and treatment assembly 140, respectively, each functional element described in detail herebelow) and/or by another device or component of system 10. Applied vacuum can be used to modify (e.g. change the shape of) the tubular tissue between the two occlusive elements and/or to increase the sealing force and/or the circumferentiality of the seal. In some embodiments, system 10 is configured to deploy a detached-balloon configured to occlude a body lumen, where the detached-balloon can later be punctured or otherwise deflated for physiologic removal by the GI tract. Deployed balloons or other occlusive elements of system 10 can be positioned to protect tissue, such as to protect the ampulla of Vater and/or the pylorus from adverse effects that can be caused by treatment of target tissue TT by treatment element 145.

In some embodiments, in addition to expandable assembly 130, treatment assembly 140 can be radially expandable and/or include one or more radially expandable elements, such as those described hereabove in reference to expandable assembly 130. In some embodiments, treatment assembly 140 is configured to radially expand and cause treatment element 145 to move closer to and/or become in contact with target tissue TT. Expansion of treatment assembly 140 can occur prior to, during and/or after treatment of target tissue TT by treatment element 145. Treatment element 145 can be mounted on, within and/or inside of an expandable assembly, such as on, within and/or inside of an expandable balloon.

In some embodiments, expandable assembly 130 and/or treatment assembly 140 comprise a length of at least 10 mm, such as a length between 10 mm and 40 mm, a length between 15 mm and 30 mm, or a length between 20 mm and 25 mm. In some embodiments, expandable assembly 130 and/or treatment assembly 140 comprise a length less than or equal to 15 mm, such as when configured to treat curvilinear portions of the GI tract. Multiple assemblies positioned on shafts 111a and/or 111b (e.g. between two and twenty treatment and/or expandable assemblies), such as expandable assembly 130 and treatment assembly 140, can be separated along a shaft by a distance less than or equal to 25 mm, such as a distance less than or equal to 20 mm. This separation distance can comprise the distance between a distal end of a tissue contacting portion of a first expandable element, and the neighboring proximal end of a tissue contacting portion of a second expandable element. In some embodiments, expandable assembly 130 comprises a length, and the separation distance between expandable assembly 130 and treatment assembly 140 is less than or equal to the expandable assembly 130 length. In these embodiments, treatment assembly 140 can comprise a similar length to that of expandable assembly 130, such as when both expandable assembly 130 and treatment assembly 140 comprise an ablation element as is described herebelow.

Expandable assembly 130 can include one or more fluid delivery elements, such as fluid delivery element 132 and/or fluid delivery element 135. Fluid delivery elements 132 and 135 are connected to one or more fluid delivery tubes (e.g. independent fluid delivery tubes), not shown but traveling proximally within shafts 111b and/or 111a and fluidly connected to EDU 330 and/or pumping assembly 340, such as via one or more ports on a handle of treatment device 100. Fluid delivery elements 132 and/or 135 can be rotatable, advanceable and/or retractable, such as via one or more control shafts, not shown but operably connected to motion transfer assembly 320. Fluid delivery elements 132 and/or 135 can comprise a nozzle or other fluid delivery element as described herein. Fluid delivery element 132 can be oriented such that fluid delivered through fluid delivery element 132 is directed toward one or more device 100 components or assemblies, such as toward treatment assembly 140 and treatment element 145 as shown in FIG. 3. Fluid delivery element 132 can be used to perform various functions such as the washing or removing of material from a device 100 component, or to cool or warm the temperature of a device 100 component. Fluid delivery element 135 can be directed toward or otherwise deliver fluid to tissue proximate device 100. Fluid delivery element 135 can have its distal end positioned within tissue (e.g. after an advancement), as shown in FIG. 3, such as to deliver fluid to one or more internal tissue layers. Alternatively, fluid delivery element 135 can have its distal end positioned in a body lumen, such as to deliver fluid to at least initially contact a tissue surface such as the wall of the duodenum. Fluid delivery element 135 can be configured to deliver a fluid to expand tissue. Alternatively or additionally, a separate submucosal or other tissue expansion device can be included, such as tissue expansion device 200. Fluid delivery element 135 and/or tissue expansion device 200 can be constructed and arranged to expand tissue as is described in applicant's co-pending International PCT Application Serial Number PCT/US2013/37485, entitled "Tissue Expansion Devices, Systems and Methods", filed Apr. 19, 2013, the contents of which is incorporated herein by reference in its entirety. Fluid delivery element 135 can be configured to deliver a cooling or warming fluid to tissue, and/or deliver a fluid configured to counter-act a chemically caused ablation, as has been described hereabove. System 10 can include one or more fluids or other material to expand one or more layers of tissue, such as when tissue expansion device 200 includes an injectable tissue-expanding material, such as a non-energy absorbing material and/or an energy-absorbing material such as water or saline.

Expandable assembly 130 and/or treatment assembly 140 can be configured to expand to a diameter of at least 10 mm, such as a diameter of at least 15 mm, at least 20 mm, at least 25 mm, at least 30 mm, or at least 40 mm. In some embodiments, expandable assembly 130 and/or treatment assembly 140 can expand to a diameter between 15 mm and 32 mm. In some embodiments, expandable assembly 130 and/or treatment assembly 140 have their diameter controlled by a component of system 10 (e.g. controller 310, EDU 330 and/or pumping assembly 340), such as to control the diameter to at least 10 mm, at least 15 mm, at least 20 mm, at least 25 mm, at least 30 mm, or at least 40 mm, or to control the diameter to a diameter between 15 mm and 32 mm. Expandable assembly 130 and/or treatment assembly 140 can be resiliently biased, such as in a radially expanded or radially compacted state. Expandable assembly 130 and/or treatment assembly 140 can be expanded and/or compacted by a control shaft. Expandable assembly 130 and/or treatment assembly 140 can be configured to achieve a round or non-round shape (e.g. a football shape) when expanded. Expandable assembly 130 and/or treatment assembly 140 can approximate a tubular shape when expanded, such as a relatively constant diameter or varying diameter tube shape. Expandable assembly 130 and/or treatment assembly 140 can be configured to un-fold to a radially expanded state, or to fold to a radially compacted state.

Expandable assembly 130 can comprise at least one functional element 138, and treatment assembly 140 can comprise at least one functional element 148. Functional elements 138 and/or 148 can be elements selected from the group consisting of: an ablation element such as one or more electrodes configured to deliver electrical energy such as radiofrequency (RF) energy; a sensor; a transducer; a fluid delivery element such as a needle, a fluid jet, a permeable membrane and/or an exit port; a heating element; a cooling element; and combinations of these.

In some embodiments, expandable assembly 130 is configured to ablate tissue, such as via functional element 138. Functional element 138 of expandable assembly 130 can comprise one or more ablation elements, such as those described in applicant's co-pending U.S. patent application Ser. No. 13/945,138, entitled "Devices and Methods for the Treatment of Tissue", filed Jan. 18, 2013, the contents of which is incorporated herein by reference in its entirety. In some embodiments, functional element 138 comprises an ablation element selected from the group consisting of: an RF energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these. In these embodiments, either or both expandable assembly 130 or treatment assembly 140 can be used to ablate target tissue TT. EDU 330 or another component of system 10 can be configured to deliver RF or other energy to functional element 138. System 10 can include ground pad 70, such as a standard RF energy delivery ground pad typically placed on the patient's back, such that EDU 330 can supply RF energy to functional element 138 and/or any other electrodes of system 10 in monopolar, bipolar and/or combined monopolar-bipolar energy delivery modes.

In some embodiments, expandable assembly 130 is configured to perform at least one non-ablative function. Expandable assembly 130 can be configured to occlude or partially occlude a lumen surrounded by tissue (as described hereabove), such as a lumen of the GI tract to be occluded during an insufflation procedure. Expandable assembly 130 can be configured to manipulate tissue, such as to linearize and/or distend GI tissue by frictionally engaging (e.g. when expanded) and applying forces to the tissue (e.g. by advancing and/or retracting shaft 111b). In some embodiments, one or more expandable assemblies 130 can perform a function selected form the group consisting of: linearizing curvilinear tissue; distending tissue; expanding tissue; occluding a body lumen; and combinations of these. Expandable assembly 130 can be configured to test and/or diagnose tissue, such as when expandable assembly 130 is used to measure a diameter of tubular tissue into which it has been inserted. Diameter measurements can be performed in various ways, including but not limited to: injection of a radiopaque fluid into expandable assembly 130 and fluoroscopic measurement of the injected fluid; controlled inflation of expandable assembly 130 to a pressure whose level corresponds to a luminal diameter; and combinations of these. In some embodiments, device 100 includes an expandable assembly that can be expanded with one or more control rods (not shown), such as to perform a diametric measurement of tubular tissue by precision measurement of control rod advancement (e.g. when control rod position correlates to expandable assembly diameter). Alternatively or additionally, tubular tissue diameter can be determined by measuring the diameter of an expandable assembly when it initially, circumferentially contacts the wall of tubular tissue (e.g. when a specific radial force is achieved and/or when contact is observed such as using fluoroscopy or ultrasound visualization devices). In some embodiments, system 10 includes a separate device, such as a balloon catheter, used to perform a diameter measurement. One or more energy delivery or other ablation parameters can be adjusted based on the measured diameter of target tissue TT and/or a target tissue segment.

In some embodiments, expandable assembly 130 is configured to expand or otherwise modify one or more layers of tissue, such as when fluid delivery element 135 and/or functional element 138 comprises a needle, water jet and/or iontophoretic fluid delivery element configured to expand submucosal tissue of the GI tract, as has been described hereabove. Alternatively or additionally, system 10 can include a separate tissue expansion device, tissue expansion device 200. Tissue expansion device 200 can comprise a reservoir or control means for delivering a pre-determined amount of fluid to tissue, such as a volume of fluid of at least 1 ml, or a volume of fluid between 2 ml and 5 ml. Tissue expansion device 200 can be configured to inject fluid into multiple injection sites (e.g. simultaneously or sequentially), such as a set of multiple injection sites selected from the group consisting of: at least 3 injection sites along a circumference of tubular tissue, a first injection site separated from a second injection site by approximately 1 cm, or between 0.5 cm to 5 cm, or between 1 cm and 3 cm, or between 1 cm and 2 cm; two or more injection sites that are axially and/or radially spaced; two or more injections sites that are separated based on the diameter of the tubular tissue into which they are injected; and combinations of these. Fluid can be injected with the assistance of one or more vacuum applying elements positioned on or near fluid delivery elements 132 and/or 135. Injected fluid can comprise a material selected from the group consisting of: water; saline; gel; and combinations of these. In some embodiments, injected fluid comprises a protein hydrogel.

Tissue expansion can greatly alleviate the need for precision of treatment, such as precision of delivery of energy and/or precision of delivery of an ablative fluid, due to the increased size (e.g. increased depth) of the target tissue TT including an associated safety-margin of tissue to which treatment causes no significant adverse event (e.g. an expanded submucosal layer prior to a mucosal layer ablation).

In some embodiments, expandable assembly 130 and/or treatment assembly 140 comprise a shape that can be adjusted by an operator, such as via a control rod manipulatable at a proximal handle and/or by motion transfer assembly 320. In some embodiments, the shape of the arrangement of one or more treatment elements 145 can be operator modified by adjusting the shape of treatment assembly 140.

Treatment element 145 can be configured to treat various thicknesses of GI tissue, such as at least the innermost 500 microns of duodenal tissue, or at least the innermost 1 mm of duodenal tissue. In some embodiments, treatment element 145 can be configured to ablate or otherwise treat a thickness of at least 600 microns, at least 1 mm or at least 1.25 mm, such as when treating the mucosa of the stomach. Treatment element 145 can be configured to treat a volume of tissue comprising a surface area and a depth, where the ratio of magnitude of the depth to the magnitude of the surface area is less than or equal to 1 to 100 (e.g. less than 1%), or less than or equal to 1 to 1000 (e.g. less than 0.1%). In some embodiments, expandable assembly 130 and/or treatment assembly 140 are configured to be in a relatively rigid state, such as during treatment of target tissue TT.

Treatment element 145 and/or other treatment elements of the present inventive concepts can be arranged in an array of elements, such as a circumferential or linear array of elements. The circumferential array can comprise a partial circumferential array of treatment elements 145, such as an array covering approximately 45° to 300° of circumferential area. Partial circumferential arrays of treatment elements 145 can treat a first target tissue segment and a second target tissue segment in two sequential steps, where the array is rotated between treatments (e.g. energy deliveries). The circumferential array can comprise a full 360° array of treatment elements 145, such that a full circumferential volume of target tissue TT can be treated in a single or multiple treatments (e.g. energy deliveries) that do not require repositioning of treatment assembly 140. In some embodiments, less than 360° of tubular tissue is treated, such as by treating a circumferential portion of tissue comprising less than or equal to a 350°, or between 300° and 350°, such as to prevent a full circumferential scar from being created.

Two or more treatment elements 145 can be arranged in a helical array. In some embodiments, at least three, four or five treatment elements independently treat target tissue, in similar or dissimilar treatments (e.g. similar or dissimilar amounts of energy, provided simultaneously and/or sequentially by EDU 330).

In some embodiments, EDU 330 and/or another device or component of system 10 provides electrical or other energy to a component of treatment device 100, such as electrical energy provided to a heating coil in a distal portion of device 100, now shown but typically connected to one or more wires traveling proximally through shaft 111*a*. EDU 330 and/or another device or component of system 10 can provide energy such as electrical energy to one or more of functional element 138 and/or functional element 148 such as when either comprises a transducer or other powered component.

Treatment element 145 can comprise one or more treatment elements configured to treat substantially the entire length of the duodenum simultaneously and/or without having to reposition treatment device 100, such as when treatment element 145 comprises an array of treatment elements positioned along substantially the entire length of the target tissue, or when treatment element 145 comprises at least one treatment element configured to rotate and/or translate along substantially the entire length of target tissue. Treatment element 145 and/or other tissue treatment elements of the present inventive concepts can be configured to treat at least 25% of the entire length of the duodenum simultaneously and/or without having to reposition treatment device 100. Treatment element 145 and/or other ablation elements of the present inventive concepts can be configured to treat a first portion of target tissue TT followed by a second portion of target issue TT. The first and second treated tissue segments can be overlapping and they can have non-parallel central axes (e.g. tissue segments in a curved portion of the duodenum). Three or more target tissue segments can be treated, such as to cumulatively ablate at least 25% or at least 50% of the duodenal mucosa.

In some embodiments, expandable assembly 130 and/or treatment assembly 140 comprise inflatable or otherwise expandable balloons, such as one or more of: a compliant balloon; a non-compliant balloon; a balloon with a pressure threshold; a balloon with compliant and non-compliant portions; a balloon with a fluid entry port; a balloon with a fluid exit port; and combinations of these. In some embodiments, expandable assembly 130 and/or treatment assembly 140 comprise a balloon which is fluidly attached to an inflation tube, such as inflation tube 136 which travels proximally through shaft 111*a* and/or 111*b* and is attached to an inflation port, not shown but typically attached to a handle on the proximal end of treatment device 100.

In some embodiments, functional element 138 of expandable assembly 130 comprises an abrasive element configured for abrading target tissue, such as an abrasive element attached to a balloon or expandable cage.

Shafts 111*a* and 111*b* can include one or more lumens passing therethrough, and can comprise wires and/or optical fibers for transfer of data and/or energy such as RF energy to functional element 138 and/or 148. Shafts 111*b* and/or 111*a* can comprise one or more shafts, such as one or more concentric shafts configured to deliver and/or recirculate hot and/or cold fluid through expandable assembly 130 and/or treatment assembly 140, respectively. In some embodiments, a heated fluid is used to pre-heat one or more treatment device 100 components and/or to deliver a bolus of hot fluid energy, each as described in applicant's co-pending International Application Serial Number PCT/US2013/28082, entitled "Heat Ablation Systems, Devices and Methods for the Treatment of Tissue", filed Feb. 27, 2013, the contents of which is incorporated herein by reference in its entirety. Device 100 can comprise multiple expandable assemblies 130, such as a first expandable assembly positioned proximal to treatment assembly 140 (not shown) and a second expandable assembly positioned distal to treatment assembly 140 (expandable assembly 130 as shown in FIG. 3).

Figure 4:
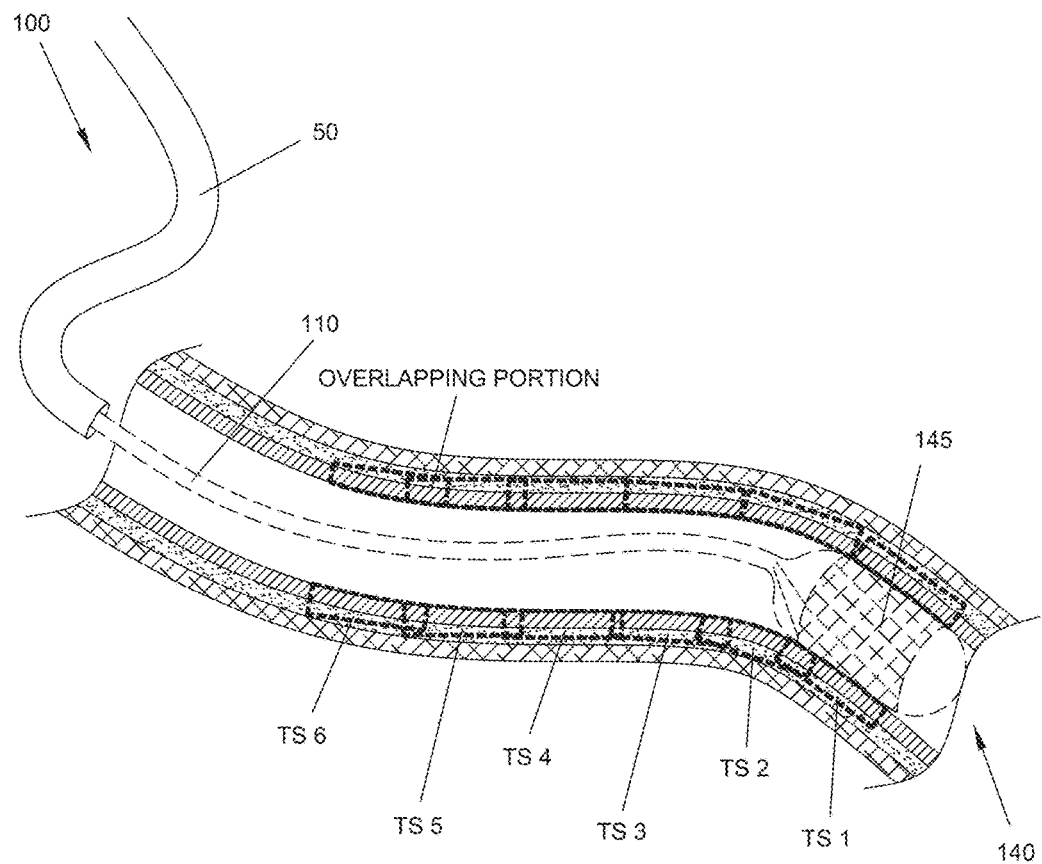
FIG. 4 is a side sectional view of the distal portion of a treatment device inserted into a curvilinear section of duodenum, consistent with the present inventive concepts.

Treatment assembly 140 and/or expandable assembly 130 can be configured to ablate tissue or otherwise perform a function while positioned in a curved segment of the GI tract, such as is described in reference to FIGS. 4 and 6 herebelow.

System 10 can be configured to ablate or otherwise treat target tissue TT, such as duodenal mucosal tissue, while avoiding damaging non-target tissue, such as the GI adventitia. Target tissue TT can include at least a portion of safety-margin tissue comprising tissue whose ablation causes minimal or no adverse effect to the patient, such as sub-mucosal tissue of the GI tract. Target tissue TT can comprise one or more portions of tissue that are treated simultaneously or sequentially. In some embodiments, the target tissue TT comprises the majority of the length of the duodenal mucosa, such as at least 25% or at least 50% of the duodenal mucosa. In some embodiments, the target tissue TT comprises at least 90% of the duodenal mucosa, or at least 95% of the duodenal mucosa. In some embodiments, the target tissue TT includes the full mucosal thickness of at least a portion of duodenal tissue, as well as at least the innermost 100 microns of submucosal duodenal tissue, or at least the innermost 200 microns of submucosal duodenal tissue. The target tissue TT can include at least one of ileal mucosal tissue or gastric mucosal tissue.

Endoscope 350 can be a standard endoscope, such as a standard GI endoscope, or a customized endoscope, such as an endoscope including sensor 353 configured to provide information related to the tissue treatment of the present inventive concepts. Endoscope 350 can include camera 352, such as a visible light, ultrasound and/or other visualization device used by the operator of system 10 prior to, during and/or after the treatment of target tissue TT, such as during insertion and/or removal of endoscope 350 and/or shafts 111a and 111b of treatment device 100. Camera 352 can provide direct visualization of internal body spaces and tissue, such as the internal organs of the GI tract. Endoscope 350 can be coupled with or otherwise include a guidewire, e.g. guidewire 60, such as to allow insertion of endoscope 350 into the jejunum and/or advancement of treatment device 100.

System 10 can be constructed and arranged to perform insufflation of a body lumen, such as insufflation of a segment of the GI tract. The body lumen can be pressurized, such as by using one or more standard insufflation techniques. Insufflation fluid can be introduced through second lumen 354 of endoscope 350. Second lumen 354 travels proximally and connects to a source of insufflation liquid and/or gas, such as pumping assembly 340, and typically a source of air, carbon dioxide, water and/or saline. Alternatively or additionally, insufflation fluid can be delivered by treatment device 100, such as through shaft 111a and/or 111b, and/or through a port in expandable assembly 130 and/or treatment assembly 140, such as when functional elements 138 and/or 148, respectively, comprise a fluid delivery port attached to a source of insufflation liquid and/or gas (e.g. provided by pumping assembly 340). Alternatively or additionally, a separate device configured to be inserted through endoscope 350 and/or to be positioned alongside endoscope 350, can have one or more lumens configured to deliver the insufflation fluid. System 10 can include one or more occlusive elements and/or devices, such as expandable assembly 130, treatment assembly 140 and/or another expandable device configured to radially expand such as to fully or partially occlude a body lumen, such that insufflation pressure can be achieved and/or maintained over time (e.g. reduce or prevent undesired migration of insufflation fluid). The one or more occlusive elements and/or devices can be positioned proximal to and/or distal to the luminal segment to be insufflated.

Pumping assembly 340 can be configured to remove fluid from a body lumen such as a segment of the GI tract. Removed fluids include but are not limited to: delivered ablative fluid; condensate of delivered ablative fluid; insufflation fluids; excess bodily fluids; chyme; digestive fluids; gas; and combinations of these. Fluids can be removed prior to, during and/or after treatment of target tissue TT by treatment element 145. Pumping assembly 340 can be configured to apply a vacuum, such as to remove fluid via at least one treatment element 145, an outflow drain, or other fluid extraction port of system 10. In some embodiments, extracted fluids are recycled, such as for subsequent delivery by at least one treatment element 145 to target tissue TT.

Pumping assembly 340 and/or EDU 330 can be configured to deliver one or more gases (e.g. carbon dioxide, nitrogen, nitrous oxide and/or air) to at least one treatment element 145 or another gas delivering component of system 10. In some embodiments, at least one treatment element 145 comprises a gas jet nozzle configured to deliver gas to target tissue, such as a gas that has been processed to remove moisture or otherwise be dry (e.g. less than the dew point of air, or at a relative humidity less than 20% or less than 10%). In some embodiments, system 10 is configured to deliver gas to cause agitation of an ablative fluid previously delivered within a body lumen. System 10 can be configured to deliver dry or other gas to move ablative fluid in a body lumen. The delivered gas can comprise a cooling gas, such as a gas below 37° C., a gas between 0° C. and 7° C. such as a gas between 2° C. and 7° C., and/or a gas at approximately 4° C. System 10 can deliver cooling gas for a time period of at least 10 seconds, at least 20 seconds or at least 30 seconds. In some embodiments, system 10 delivers cooling gas at a temperature less than 0° C. for a time period less than or equal to 20 seconds, less than or 10 seconds, or less than or equal to 5 seconds. In some embodiments, system 10 is configured to deliver gas at a temperature at or above 42° C., such as to remove moisture or otherwise dry a tissue wall of the GI tract. System 10 can be configured to deliver carbon dioxide gas.

Functional element 138 and/or functional element 148 can comprise a sensor. In some embodiments, functional element 138, functional element 148, sensor 353 and/or another sensor of system 10, such as sensor 139 positioned on expandable assembly 130 and/or sensor 149 positioned on treatment assembly 140, can comprise a sensor selected from the group consisting of: temperature sensors such as thermocouples, thermistors, resistance temperature detectors and optical temperature sensors; strain gauges; impedance sensors such as tissue impedance sensors; pressure sensors; blood sensors; optical sensors such as light sensors; sound sensors such as ultrasound sensors; electromagnetic sensors such as electromagnetic field sensors; visual sensors; and combinations of these. The sensors can be configured to provide information to one or more components of system 10, such as to controller 310 and/or EDU 330, such as to monitor the treatment of target tissue TT and/or to treat target tissue TT in a closed loop configuration. Energy delivery from EDU 330 can be initiated, stopped and/or modified based on one or more sensor readings. Algorithm 311 of controller 310 and/or EDU 330 can be configured to determine one or more treatment parameters. In some embodiments, algorithm 311 processes one or more sensor signals to modify an amount of ablative fluid delivered, rate of ablative fluid delivery, energy delivered, power of energy delivered, voltage of energy delivered, current of energy delivered and/or temperature of ablative fluid or energy delivery. Alternatively or additionally, algorithm 311 can comprise an algorithm configured to determine an energy delivery zone parameter such as an energy delivery zone parameter selected from the group consisting of: anatomical location of an energy delivery zone; size of energy delivery zone; percentage of energy delivery zone to receive energy; type of energy to be delivered to an energy delivery zone; amount of energy to be delivered to an energy delivery zone; and combinations of these. Information regarding the energy delivery zone parameter can be provided to an operator of system 10. This information can be employed to set an energy delivery zone parameter, assist the operator in determining the completion status of the procedure (e.g. determining when the procedure is sufficiently complete) and/or to advise the operator to continue to complete a pre-specified area or volume of target tissue. The total area of treatment or number of energy delivery zones or number of treatments during a particular procedure (any of which can be employed in algorithm 311) can be defined by patient clinical or demographic data, as described herein.

Sensor 149 of treatment assembly 140 can comprise a gravimetric sensor. In these embodiments, sensor 149 can comprise an accelerometer or other sensor configured to provide a signal representing the orientation of treatment assembly 140 and/or treatment element 145 as it relates to the force of earth's gravity. In embodiments in which treatment element 145 delivers ablative fluid to target tissue TT, the signal provided by sensor 149 can provide information for manual and/or automated control of ablative fluid delivery direction. In some embodiments, gravimetric orientation of device 100 is provided to an operator, such as via a screen on controller 310. In some embodiments, the signal from sensor 149 is recorded by controller 310, such as to adjust a spray pattern delivered by treatment assembly 140 and/or treatment element 145. Based on a signal from sensor 149, treatment element 145 and/or shaft 111a can be positioned to deliver ablative fluid in upward and/or side-ways (i.e. horizontal) directions, such as to allow delivered fluid to flow across the walls of a lumen in a downward direction. Controller 310 can be configured to adjust the flow pattern of ablative fluid delivery by adjusting the rotation and/or translation of treatment assembly 140 (e.g. by creating an asymmetric movement). Controller 310 can be configured to adjust the flow pattern of ablative fluid delivery by adjusting which of multiple treatment elements 145 deliver ablative fluid (e.g. by turning on or more one or more electronic fluid valves) or by adjusting a nozzle direction or nozzle flow path geometry of treatment element 145 (e.g. when treatment element 145 comprises a rotatable nozzle and/or a nozzle with an adjustable orifice). In some embodiments, controller 310 utilizes a signal from sensor 149 to manipulate one or more treatment elements 145 to deliver fluid in a relatively upward direction. In some embodiments, system 10 includes a fluid removal element, such as a treatment element 145 configured to remove fluid or an outflow drain, and the fluid removal element is gravimetrically oriented by a signal provided by sensor 149.

Sensors 139 and/or 149 can comprise a chemical detection sensor, such as a chemical detection sensor to confirm proper apposition of expandable assembly 130 and/or treatment assembly 140. In this configuration, a chemical sensor such as a carbon dioxide sensor can be placed distal to expandable assembly 130 and/or treatment assembly 140, and a fluid such as carbon dioxide gas can be introduced proximal to the expandable assembly 130 and/or treatment assembly 140. Detection of the introduced fluid by sensor 139 and/or 149 can indicate inadequate apposition of expandable assembly 130 and/or treatment assembly 140, respectively. Readjustment to achieve sufficient apposition can prevent inadequate treatment of target tissue TT (e.g. inadequate transfer of energy) and/or prevent inadequate measurement, modification, manipulation and/or diagnosis of target tissue TT.

Functional element 138, functional element 148, sensor 139, sensor 149, sensor 353 and/or another sensor of system 10 can be a sensor configured to provide information related to the tissue treatment performed by treatment assembly 140 and/or expandable assembly 130, such as a visual sensor mounted to treatment assembly 140 and/or expandable assembly 130 that is configured to differentiate tissue types that are proximate treatment assembly 140 and/or expandable assembly 130. In some embodiments, system 10 is constructed and arranged to differentiate mucosal and submucosal tissue, such as to adjust one or more treatment parameters (e.g. to stop treatment and/or modify the temperature of treatment) based on the differentiation. Applicable visible sensors include but are not limited to: visible light camera; infrared camera; CT Scanner; MRI; and combinations of these. In some embodiments, energy provided by EDU 330 is based on one or more signals from the visible sensor, such as a sensor providing a signal correlating to tissue color wherein the energy delivered is modified based on a tissue color change. Sensors 149 and 139 can comprise a sensor configured to provide information related to the tissue treatment performed by treatment assembly 140 and/or expandable assembly 130, respectively, such as a temperature sensor configured to monitor the temperature of treatment provided by treatment assembly 140 and/or expandable assembly 130 and/or tissue proximate treatment assembly 140 and/or expandable assembly 130. Sensors 149 and/or 139 can comprise multiple temperature sensors, such as multiple temperature sensors positioned on treatment assembly 140 and/or expandable assembly 130, respectively, with a spacing of at least one sensor per square centimeter. Energy delivered by EDU 330 can be based on signals recorded by the multiple temperature sensors.

Functional element 138 and/or functional element 148 can comprise a transducer. In these and other embodiments, functional element 138, functional element 148, and/or another transducer of system 10 can be a transducer selected from the group consisting of: a heat generating element; a drug delivery element such as an iontophoretic drug delivery element; a magnetic field generator; an ultrasound wave generator such as a piezo crystal; a light producing element such as a visible and/or infrared light emitting diode; and combinations of these.

In some embodiments, EDU 330 and/or another device of component of system 10 is configured to deliver a visualizable material, such as a visualizable material delivered to one or more treatment elements 145. In some embodiments, visualizable material is delivered by treatment element 145 onto and/or beneath the surface of tissue, to assist in the treatment of target tissue TT, such as to assess the status of tissue ablation. In some embodiments, the visualizable material is selected from the group consisting of; radiopaque agent; ultrasonically visible material; magnetically visible material; and combinations of these. An imaging device of system 10, such as imaging device 410 described herebelow, can be used to create an image of the visualizable material during and/or after delivery of the visualizable material.

In some embodiments, EDU 330 or another device of component of system 10 is configured to deliver abrasive particles, such as abrasive particles delivered to one or more treatment elements 145. In some embodiments, visualizable material is also delivered by EDU 330 to assist in the treatment of tissue, such as to improve ablation caused by a mechanical abrasion treatment.

In some embodiments, EDU 330 is configured to deliver at least RF energy, and system 10 includes ground pad 70 configured to be attached to the patient (e.g. on the back of the patient), such that RF energy can be delivered in monopolar delivery mode to one or more electrode-based treatment elements 145 of treatment device 100 or to one or more electrodes of another treatment device of system 10 (e.g. second treatment device 100'). Alternatively or additionally, EDU 330 can be configured to deliver energy in a bipolar RF mode, such as bipolar energy delivered between any two electrode-based treatment elements 145 of treatment device 100 or between any other two electrodes of another treatment device of system 10. Alternatively or additionally, EDU 330 can be configured to deliver energy in a combined monopolar-bipolar mode.

EDU 330 can be configured to deliver RF and/or other forms of energy to one or more treatment elements 145 of treatment assembly 140 and/or a treatment element expandable assembly 130. In some embodiments, EDU 330 delivers energy selected from the group consisting of: RF energy; microwave energy; plasma energy; ultrasound energy; light energy; and combinations of these. Energy can be continuous and/or pulsed, and can be delivered in a closed-loop fashion as described hereabove. Energy delivery parameters such as power, voltage, current and frequency can be held relatively constant or they can be varied by EDU 330. Energy delivery can be varied from a first tissue location (e.g. a first portion of target tissue TT) to a second location (e.g. a second portion of target tissue TT), such as a decrease in energy from a first treated location to a second treated location when the second treated location is thinner than the first treated location. Alternatively or additionally, energy delivery can be varied during a single application of energy to a single tissue location, such as by adjusting one or more energy delivery parameters during a continuous energy delivery. Alternatively or additionally, one or more energy delivery parameters can be varied between a first treatment of target tissue and a second treatment of target tissue, for example a first treatment performed during a first clinical procedure and a second treatment performed during a second clinical procedure, such as when the second treatment is performed at least twenty-four hours after the first treatment.

Pumping assembly 340 and/or EDU 330 typically include one or more fluid pumps, such as one or more peristaltic, displacement and/or other fluid pumps; as well as one or more heat exchangers and/or other fluid heating elements internal and/or external to device 100. Pumping assembly 340 and/or EDU 330 can be configured to rapidly deliver and/or withdraw fluid to and/or from treatment assembly 140 and/or expandable assembly 130 via one or more fluid transport means. Fluid transport means can include a pump configured to deliver fluid at a flow rate of at least 50 ml/min and/or a pump and/or vacuum source configured to remove fluid at a flow rate of at least 50 ml/min. In some embodiments, system 10 is configured to deliver fluid, such as a liquid, at a flow rate of at least 500 ml/min, or at least 750 ml/min. A pump and/or vacuum source can be configured to continuously exchange hot fluid and/or to perform a negative pressure priming event to remove fluid from one or more fluid pathways of device 100. Pumping assembly 340, EDU 330, first treatment device 100 and or second treatment device 100' can include one or more valves in the fluid delivery and/or fluid withdrawal pathways or one or more other valves in the fluid pathway within treatment assembly 140 and/or expandable assembly 130. Valves can be configured to control entry of fluid into an area and/or to maintain pressure of fluid within an area. Valves can be used to transition from a heating fluid, such as a fluid of 90° C. maintained in a treatment assembly for approximately 12 seconds, to a cooling fluid, such as a fluid between 4° C. and 10° C. maintained in the assembly element for approximately 30 to 60 seconds. Typical valves include but are not limited to: duck-bill valves; slit valves; electronically activated valves; pressure relief valves; and combinations of these. Pumping assembly 340 and/or EDU 330 can be configured to rapidly inflate and/or deflate treatment assembly 140 and/or expandable assembly 130. Pumping assembly 340 and/or EDU 330 can be configured to purge the fluid pathways of first treatment device 100 and/or second treatment device 100' with a gas such as air, such as to remove cold and/or hot fluid from the devices and/or to remove gas bubbles from the devices.

EDU 330, treatment element 145 and/or other components of system 10 can be configured to treat target tissue TT with a non-desiccating ablation, such as by avoiding tissue temperatures above 100° C., avoiding the creation of steam, or otherwise avoiding deleterious desiccation of tissue. System 10 can be configured to minimize heat production in the outermost 50% of a mucosal layer, such as to ablate the outermost 50% of the mucosal layer via thermal conduction. System 10 can be configured to minimize heat production in the outermost 80% of a mucosal layer, such as to ablate the outermost 80% of the mucosal layer via thermal conduction. System 10 can be configured to maximize the flow of electrical current, such as through the innermost 50% of a mucosal layer, or through the innermost 20% of a mucosal layer. In some embodiments, system 10 can be configured to avoid detachment of tissue particles.

EDU 330, treatment element 145 and/or other components of system 10 can be configured to treat target tissue TT such that the temperature of at least a portion of the target tissue TT rises rapidly, such as at a rate of greater than or equal to 17.5° C. per second. Treatment can be delivered to cause the temperature of at least a portion of the target tissue TT to reach a setpoint temperature between 60° C. and 90° C., such as a setpoint temperature between 65° C. and 85° C. System 10 can be configured to cause the target tissue TT to elevate to a setpoint temperature and maintain that setpoint temperature, such as by maintaining the setpoint temperature for a time period between 2 and 40 seconds. In these embodiments, the setpoint temperature can be between 60° C. and 90° C., such as a setpoint temperature between 65° C. and 85° C. that is maintained for between 5 and 15 seconds. In some embodiments, after a setpoint temperature is achieved and/or maintained, the treatment can be adjusted (e.g. by adjusting energy delivery from EDU 330) such that tissue temperature decreases over time, such as to match a tissue response of the target tissue TT.

Controller 310 can include a graphical user interface configured to allow one or more operators of system 10 to perform one or more functions such as entering of one or more system input parameters and visualizing and/or recording of one or more system output parameters. Controller 310 can include one or more user input components (e.g. touch screens, keyboards, joysticks, electronic mice and the like), and one or more user output components (e.g. video displays; liquid crystal displays; alphanumeric displays; audio devices such as speakers; lights such as light emitting diodes; tactile alerts such as assemblies including a vibrating mechanism; and the like). Examples of system input parameters include but are not limited to: temperature of ablative fluid to be delivered such as temperature of fluid to be delivered to a nozzle or to an expandable reservoir such as a balloon; type of ablative fluid to be delivered; rate of ablative fluid to be delivered; volume of ablative fluid to be delivered; type of energy to be delivered such as RF energy, thermal energy and/or mechanical energy; quantity of energy to be delivered such as a cumulative number of joules of energy to be delivered and/or peak amount of energy to be delivered; types and levels of combinations of energies to be delivered; energy delivery duration; pulse width modulation percentage of energy delivered; temperature of a cooling fluid to be delivered; temperature of a priming fluid to be delivered; flow rate of a fluid to be delivered; volume of a fluid to be delivered; number of reciprocating motions for an energy delivery element to transverse; temperature for a treatment assembly such as target temperature and/or maximum temperature; insufflation pressure; insufflation duration; and combinations of these. System input parameters can include information based on patient anatomy and/or conditions such as pre-procedural and/or peri-procedural parameters selected from the group consisting of: mucosal density and/or thickness; mucosal "lift" off of submucosa after a submucosal injection; longitudinal location of target tissue within the GI tract; and combinations of these. Examples of system output parameters include but are not limited to: temperature information such as tissue and/or treatment assembly temperature information; pressure information such as balloon pressure information and/or insufflation pressure information; force information such as level of force applied to tissue information; patient information such as patient physiologic information recorded by one or more sensors; and combinations of these.

Controller 310 and/or one or more other components of system 10 can include an electronics module, such as an electronics module including a processor, memory, software, and the like. Controller 310 is typically configured to allow an operator to initiate, modify and cease treatment of target tissue TT by the various components of system 10, such as by controlling EDU 330 and/or pumping assembly 340. Controller 310 can be configured to modify one or more tissue treatment parameters, such as a parameter selected from the group consisting of: temperature of an ablative fluid to be delivered directly to tissue or to an expandable reservoir such as a balloon; type of ablative fluid to be delivered; rate of ablative fluid to be delivered; volume of ablative fluid to be delivered; pulse width modulation on-time and/or off-time; a time division multiplexing parameter; and combinations of these. Controller 310 can be configured for manual control, so that the operator first initiates the tissue treatment, then allows the treatment element 145 and/or another associated treatment element to treat the target tissue TT for some time period, after which the operator terminates the treatment.

Controller 310 and EDU 330 can be configured to treat target tissue TT in constant, varied, continuous and discontinuous energy delivery or other treatment delivery profiles. Pulse width modulation and/or time division multiplexing (TDM) can be incorporated to achieve precision of an ablative treatment, such as to ensure ablation of target tissue TT while leaving non-target tissue intact.

In some embodiments, where system 10 is further configured to perform hot fluid ablation, controller 310 can be configured to adjust the temperature, flow rate and/or pressure of fluid delivered to an expandable reservoir, such as when treatment element 145 and/or expandable assembly 130 comprise a balloon. Controller 310 can be configured to initiate insufflation and/or to adjust insufflation pressure. Controller 310 can be configured to deliver energy or otherwise treat target tissue in a closed-loop fashion, such as by modifying one or more tissue treatment parameters based on signals from one or more sensors of system 10, such as those described hereabove. Controller 310 can be programmable such as to allow an operator to store predetermined system settings for future use.

Controller 310 can comprise an impedance monitoring assembly, such as an impedance monitoring assembly that receives impedance information from one or both of sensor 139 of expandable assembly 130 and/or sensor 149 of treatment assembly 140. EDU 330 can deliver RF energy to one or more electrode-based treatment elements of system 10 based on the impedance determined by the impedance monitoring assembly.

Numerous embodiments of the systems, methods and devices for treating target tissue TT described hereabove include controlling and/or monitoring the change in target tissue temperature to cause its ablation, such as a temperature increase above 43° C., typically above 60° C., 70° C. or 80° C., to ablate at least a portion of the target tissue TT. One or more cooling fluids can be delivered to limit or otherwise control ablation, such as to prevent damage to non-target tissue, such as the duodenal adventitia. Pumping assembly 340 can be configured to deliver a fluid to tissue and/or a component and/or assembly of system 10, such as to warm and/or cool the tissue, component and/or assembly. Pumping assembly 340 can be configured to deliver a cooling fluid to a luminal wall such as the duodenal wall, such as prior to a delivery of energy, during a delivery of energy and/or after a delivery of energy. In some embodiments, a chilled fluid is used to cool tissue prior to, during and/or after a high temperature ablation of tissue. System 10 can be configured to deliver a fluid at a temperature below 37° C. or below 20° C. The chilled fluid can be delivered at a temperature between 0° C. and 7° C., and in some embodiments, the chilled fluid is delivered at a temperature less than 0° C. System 10 to can be configured to deliver chilled fluid at multiple temperatures to target tissue TT and/or other tissue. System 10 can be configured to deliver a first chilled fluid at a first temperature for a first time period, followed by a second chilled fluid delivered at a second temperature for a second time period. The first and second chilled fluids can be similar or dissimilar fluids, such as similar or dissimilar liquids and/or gases. In some embodiments, the first chilled fluid is colder than the second chilled fluid, such as a first chilled fluid delivered at approximately 4° C. for a time period of approximately 5 seconds, followed by fluid delivered at a higher temperature (e.g. a temperature between 10° C. and 37° C.) for a time period of at least 5 seconds. The chilled fluid can be delivered between treatment of a first portion of target tissue and a second portion of target tissue (e.g. to the same or different tissue), such as to remove residual heat remaining after the first treatment. The cooling fluid can be delivered through functional element 138 of expandable assembly 130 and/or functional element 148 of treatment assembly 140, such as when functional elements 138 and/or 148 comprises a fluid delivery element such as a nozzle, an exit hole, a slit, or a permeable membrane. The cooling fluid can be supplied to a location within expandable assembly 130 and/or treatment assembly 140, such as when expandable assembly 130 and/or treatment assembly 140 comprises a balloon or other expandable reservoir configured to contact tissue. Alternatively or additionally, pumping assembly 340 can be fluidly attached to another component of treatment device 100 and/or system 10, the attached component not shown but configured to deliver fluid to tissue and/or a component of system 10 such as to add and/or absorb heat. Pumping assembly 340 can comprise a cryogenic source used to deliver fluids at low temperatures, such as temperatures below 0° C. Typical fluids delivered include but are not limited to: liquids such as water and/or saline; gases such as carbon dioxide, nitrogen, nitrous oxide and/or air; and combinations of these.

Pumping assembly 340 can include a desiccant and/or drying assembly configured to dehydrate or otherwise remove moisture from one or more delivered gases prior to their delivery. In some embodiments, fluid provided to one or more treatment elements 145 has its temperature modified by a component in a distal portion of device 100, such as a heating or cooling element integral or proximal to treatment element 145 (e.g. a peltier cooling element, an expanded gas cooling assembly, or a heating coil integral to treatment element 145). Alternatively or additionally, system 10 can include a component configured to directly contact tissue in order to cool or warm tissue. In some embodiments, radially expandable assembly 130, functional element 138 and/or functional element 148 can be configured to contact tissue and remove and/or add heat from the contacted tissue.

System 10 can include a motion control mechanism, such as motion transfer assembly 320. Motion transfer assembly 320 can be configured to rotate, translate and/or otherwise move a component of system 10, such as to move one or more of treatment assembly 140, treatment element 145 and/or expandable assembly 130. In some embodiments, motion transfer assembly 320 is configured to rotate and/or axially translate shafts 111a and/or 111b such that treatment assembly 140 and/or expandable assembly 130, respectively, are rotated and/or translated. Motion transfer assembly 320 can be configured to rotate treatment assembly 140 and/or expandable assembly 130 independently or in unison. Motion transfer assembly 320 can be configured to translate treatment assembly 140 as treatment is applied to a portion of target tissue TT. In some embodiments, contiguous tissue segments are treated by device 100 continuously as motion transfer assembly 320 causes treatment assembly 140 to translate at a rate of at least 10 cm per minute, or at a rate of least 20 cm per minute. In some embodiments, treatment assembly 140 is manually translated, such as at a rate of at least 10 cm per minute, or at least 20 cm per minute. Motion transfer assembly 320 can be configured to translate treatment assembly 140 between a first tissue treatment and a second tissue treatment. Motion transfer assembly 320 can include one or more rotational and/or linear drive assemblies, such as those including rotational motors, magnetic drives, lead screw and/or other linear actuators, and the like which are operably connected to shaft 111a and/or 111b. Shafts 111a and/or 111b are constructed with sufficient column strength and/or torque transfer properties to sufficiently rotate and/or translate treatment assembly 140 and/or expandable assembly 130, respectively. Motion transfer assembly 320 can be in communication with controller 310, such as to activate, adjust and/or otherwise control motion transfer assembly 320 and thus the motion of treatment assembly 140 and/or expandable assembly 130. Motion transfer assembly 320 can be manually driven and/or automatically (e.g. motor) driven. Alternatively or additionally, motion transfer assembly 320 can be used to advance and/or retract treatment assembly 140 and/or expandable assembly 130 from a first position to treat a first portion of target tissue, to a second position to treat a second portion of target tissue. In this embodiment, repositioning of treatment assembly 140 and/or expandable assembly 130 can be configured to provide overlapping treatment, such as the overlapping treatment described in reference to FIG. 4 herebelow.

In some embodiments, system 10, first treatment device 100 and/or second treatment device 100' are constructed and arranged to perform a fractional treatment of tissue, such as is described hereabove in reference to FIG. 1. First treatment device 100 and/or second treatment device 100' can be constructed and arranged to treat target tissue with a fractional delivery of RF energy, such as monopolar and/or bipolar RF energy delivered from an array of electrodes positioned on an expandable element. In some embodiments, first treatment device 100 and/or second treatment device 100' are configured as a laser or other light energy delivery device constructed and arranged to provide a fractional energy delivery to target tissue, such as device of similar construction to device 500 of FIGS. 5A and 5B described herebelow. In some embodiments, first treatment device 100 and/or second treatment device 100' are configured to vaporize at least a portion of target tissue.

As described hereabove, system 10 can include one or more additional treatment devices, such as second treatment device 100'. Second treatment device 100' and/or other treatment devices of the present inventive concepts can be configured to treat target tissue TT in the same clinical procedure, or in a clinical procedure performed at least twenty-four hours after the first clinical procedure. Second treatment device 100' can be of similar or dissimilar construction to first treatment device 100. In some embodiments, second treatment device 100' comprises an expandable assembly with a different diameter than expandable assembly 130 of device 100. In some embodiments, second treatment device 100' comprises a treatment element with a different construction and arrangement than treatment element 145 of treatment device 100. In some embodiments, second treatment device 100' comprises a device selected from the group consisting of: hot fluid filled balloon device; RF energy delivery device; vapor ablation device; cryoablation device; laser ablation device; ultrasound ablation device; mechanical abrasion device; and combinations of these. Second treatment device 100' can comprise at least one ablation element selected from the group consisting of: an RF energy delivery element such as one or more electrodes, each comprising one or more elongate conductors; an ultrasonic transducer such as one or more piezo crystals configured to ablate tissue; a laser energy delivery element such as one or more optical fibers and/or laser diodes; a heat delivery element such as a hot fluid filled balloon; a rotating ablation element; a circumferential array of ablation elements; and combinations of these.

System 10 can further include one or more imaging devices, such as imaging device 410. Imaging device 410 can be configured to be inserted into the patient and can comprise a visual light camera; an ultrasound imager; an optical coherence domain reflectometry (OCDR) imager; and/or an optical coherence tomography (OCT) imager, such as when integral to, attached to, contained within and/or proximate to shaft 111a and/or 111b. Imaging device 410 can be inserted through a separate working channel of endoscope 350, lumen not shown. In one embodiment, imaging device 410 is an ultrasound transducer connected to a shaft, not shown but surrounded by shaft 111a and typically rotated and/or translated to create a multi-dimensional image of the area surrounding imaging device 410. Alternatively or additionally, imaging device 410 can be external to the patient, such as an imaging device selected from the group consisting of: an X-ray; a fluoroscope; an ultrasound image; an MRI; a PET Scanner; a near-infrared imaging camera; a fluorescence imaging camera; and combinations of these. Image and other information provided by imaging device 410 can be provided to an operator of system 10 and/or used by a component of system 10, such as controller 310, to automatically or semi-automatically adjust one or more system parameters such as one or more energy delivery parameters.

System 10 can further include protective element 191, configured to be positioned proximate tissue to prevent damage to certain tissue during tissue ablative fluid delivery, other energy delivery and/or other tissue treatment event. Protective element 191 can comprise an element selected from the group consisting of: a deployable and/or recoverable cap and/or covering; an advanceable and/or retractable protective sheath; and combinations of these. Protective element 191 can be delivered with endoscope 350 and/or another elongate device such that protective element 191 can be placed over or otherwise positioned to protect non-target tissue, such as tissue selected from the group consisting of: ampulla of Vater, bile duct, pancreas, pylorus, muscularis externae, serosa; and combinations of these. In some embodiments, protective element 191 is placed prior to treatment of at least a portion of target tissue TT, and removed in the same clinical procedure. In other embodiments, protective element 191 is implanted in a first clinical procedure, and removed in a second clinical procedure, such as a second clinical procedure as described herein. System 10 can be configured to identify non-target tissue, such as via a camera used to identify the ampulla of Vater.

System 10 can be configured to prevent excessive distension of the duodenum such as distension that could cause tearing of the serosa. In some embodiments, system 10 is configured such that all tissue contacting components and/or fluids delivered by system 10 maintain forces applied on a GI wall below 1.0 psi, such as less than 0.5 psi, or less than 0.3 psi. System 10 can be configured to avoid or otherwise minimize damage to the muscularis layer of the GI tract, such as by controlling pressure of target tissue treatment (e.g. via controlling expansion force of treatment assembly 140 and or expandable assembly 130) and/or by otherwise minimizing trauma imparted on any tissue by one or more components of system 10.

System 10 can further include one or more pharmaceutical and/or other agents 420, such as an agent configured for systemic and/or local delivery to a patient. Agents 420 can be delivered pre-procedurally, peri-procedurally and/or post-procedurally. Agents 420 can comprise one or more imaging agents, such an imaging agent used with imaging device 410. Agents 420 can be one or more pharmaceutical or agents configured to improve healing, such as agents selected from the group consisting of: antibiotics, steroids, mucosal cytoprotective agents such as sucralfate, proton pump inhibitors and/or other acid blocking drugs; and combinations of these. Alternative or in addition to agents 420, pre-procedural and/or post-procedural diets can be employed, as described herein. For example, pre-procedural diets can include food intake that is low in carbohydrates and/or low in calories, and post-procedural diets can include food intake that comprise a total liquid diet and/or a diet that is low in calories and/or low in carbohydrates.

In some embodiments, system 10 does not include a chronically implanted component and/or device, only body inserted devices that are removed at the end of the clinical procedure or shortly thereafter, such as devices removed within 8 hours of insertion, within 24 hours of insertion and/or within one week of insertion. In an alternative embodiment, implant 192 can be included. Implant 192 can comprise at least one of: a stent; a sleeve; and/or a drug delivery device such as a coated stent, a coated sleeve and/or an implanted pump. Implant 192 can be inserted into the patient and remain implanted for a period of at least one month, at least 6 months or at least 1 year. In some embodiments, a first clinical procedure is performed treating target tissue, and a subsequent second clinical procedure is performed, as is described herein. In these two clinical procedure embodiments, a device can be implanted in the first clinical procedure, and removed in the second clinical procedure.

System 10 can include sizing device 430 which is constructed and arranged to be placed into one or more locations of the gastrointestinal tract or other internal location of the patient and measure the size or other geometric parameter of tissue. In some embodiments, sizing device 430 comprises a balloon, expandable cage or other sizing element constructed and arranged to measure the inner surface diameter of a tubular tissue such as duodenal and/or jejunal tissue. A diameter measurement can be performed by inflating a balloon of sizing device 430 to a predetermined pressure and performing a visualization procedure to determine balloon diameter. Alternatively or additionally, a balloon can be filled with a fluid and one or more of fluid volume or fluid pressure is measured to determine balloon diameter and subsequently diameter of tubular tissue proximate the balloon. In some embodiments, subsequent apposition of treatment assembly 140 can be determined using these tissue geometry measurements. Alternatively or additionally, an expandable element such as a balloon or cage can comprise two or more electrodes configured to provide a tissue impedance measurement whose value can be correlated to a level of apposition of the expandable element, and whose expanded diameter (e.g. visually measured) subsequently correlated to a diameter of tubular tissue proximate the expandable element. In some embodiments, treatment assembly 140 and/or expandable assembly 130 comprises sizing device 430, such as when treatment assembly 140 and/or expandable assembly 130 comprise a balloon or other sizing element used to measure a diameter of the inner surface of tubular tissue.

Any of the components of system 10 can include a coating, such as a lubricious coating. In some embodiments, treatment elements 145 and/or radially expandable elements such as balloons include a lubricious or other material property modifying coating. In some embodiments, a radially expandable treatment assembly 140 and/or expandable assembly 130 comprise a hydrophilic coating, for example configured to disperse or otherwise move an ablative fluid.

Each of the components and/or devices of system 10 can be removably attached to another component, particularly treatment device 100, controller 310, EDU 330, motion transfer assembly 320, pumping assembly 340, ground pad 70, endoscope 350 and/or second treatment device 100'. Typical attachment means include but are not limited to mechanical or electromechanical connectors providing an electrical, optical and/or fluidic connection between the attached components.

Referring now to FIG. 4, a side sectional view of the distal portion of a treatment device inserted into a curvilinear section of duodenum is illustrated, consistent with the present inventive concepts. Treatment device 100 comprises shaft 110, a relatively flexible, biocompatible, elongate structure configured for insertion into a body lumen such as the duodenal tissue shown. Shaft 110 is typically connected to a handle on its proximal end, not shown but configured to allow an operator to advance, retract and otherwise manipulate or control treatment device 100. Treatment device 100 can be configured for delivery over a guidewire, via a lumen from a proximal portion to a distal portion, or via a rapid exchange sidecar in the distal portion of the device (guidewire lumen and sidecar not shown but known to those of skill in the art). Shaft 110 is shown inserted through introducer 50 which can comprise an endoscope, sheath, or other body introduction device.

Treatment device 100 further comprises treatment assembly 140, which can be similar to treatment assembly 140 of FIG. 3. Treatment assembly 140 can be expandable and/or it can include one or more expandable elements. Treatment assembly 140 comprises treatment element 145, which is constructed and arranged to deliver energy to one or more portions of an energy delivery zone and to treat one or more portions of target tissue. Treatment element 145 can comprise one or more treatment elements such as a balloon configured to receive sufficiently hot or cold ablative fluid; a fluid delivery element such as a nozzle configured to deliver ablative fluid directly onto tissue; one or more electrodes configured to deliver RF energy to tissue; a light energy delivery element such as a laser light energy delivery element described in reference to FIGS. 5A and 5B hereinbelow; and/or other ablation or other tissue treatment elements such as those described in reference to FIG. 3 hereabove.

Treatment assembly 140 has been positioned in a distal portion of duodenal tissue, such as a section that includes an expanded segment of submucosal tissue (expansion not shown). Treatment assembly 140 has been radially expanded such as to contact the mucosal surface of the duodenum at a discrete tissue segment of target tissue, treatment portion 1 as shown. Treatment portion 1 is located distal to a series of sequential tissue segments of target tissue, treatment portions 2 through 6 as shown. Treatment element 145 is shown in FIG. 4 positioned to ablate or otherwise treat tissue segment 1. Treatment element 145 can be operably connected to one or more wires, fluid delivery tubes, or other conduits, not shown but such as conduit 141 of FIG. 3, such that treatment element 145 can treat tissue proximate to treatment element 145. As described above, each of treatment portions 1 through 6 has a corresponding energy delivery zone (not shown) to which energy is delivered from treatment element 145 to cause the appropriate treatment of target tissue.

Treatment assembly 140 can be sized to allow positioning in curved segments of the GI tract with a minimum radius of curvature, such as a curved segment of the duodenum and/or jejunum with an average radius of curvature less than 5 cm over a 75° arc, or less than 3 cm over a 75° arc, as described herebelow in reference to FIG. 6. In these curved segments (and straighter segments as well), treatment assembly 140 can be expanded without exerting undesired force onto tissue (e.g. expanded to contact the tissue wall and/or to position treatment element 145 a fixed distance from the tissue wall). In some embodiments, treatment assembly 140 is constructed and arranged to treat curved segments of the GI tract and comprises a length less than or equal to 30 mm, such as less than or equal to 25 mm, less than or equal to 20 mm, less than or equal to 15 mm. After treatment of the tissue segment 1, treatment assembly 140 can be repositioned to tissue segment 2, just proximal to the tissue segment 1, with or without contracting treatment assembly 140 prior to the repositioning. Subsequently, a second tissue treatment (e.g. a second energy delivery) can be performed. The steps of repositioning and treating portions of target tissue are repeated until tissue segments 3, 4, 5, and 6 have been treated. In a single clinical procedure, the combined length of target tissue segments 1 through 6 can represent between 25% and 100% of the length of the duodenal mucosa length, such as when between 2 and 50 axial segments of tissue receive between 2 and 50 energy deliveries from treatment element 145 and/or another treatment element. In some embodiments, each of tissue segments 1 through 6 have a maximum axial length of less than 20 cm, less than 15 cm, less than 10 cm, less than 5 cm or less than 3 cm. In some embodiments, the cumulative axial length of tissue segments treated, (e.g. at least segments 1 through 6) is less than 100 cm, or less than 50 cm. Alternatively or additionally, other tissue can be treated, such as has been described hereabove.

Target tissue segments 1 through 6 typically include common or overlapping tissue segments, such as is shown in FIG. 4. While the embodiment of FIG. 4 shows six target tissue segments being treated, more or fewer segments can be treated. Tissue treatments can be performed in a contiguous manner (e.g. $1^{st}$ portion followed by $2^{nd}$ portion, followed by $3^{rd}$ portion, etc); however any order can be performed. In some embodiments, multiple contiguous or discontiguous tissue segments are treated simultaneously. In some embodiments, contiguous tissue segments are treated by device 100 continuously, as treatment assembly 140 is translated proximally and/or distally, such as via a manual or automated retraction and/or advancement, respectively, as has been described in reference to FIG. 1 hereabove. In some embodiments, treatment of target tissue is performed as treatment assembly 140 translates at a rate of at least 10 cm per minute. In some embodiments, a segment of non-treated GI tissue is positioned between two segments of treated GI tissue, such as a non-treated segment of GI tissue in a sharp bend, such as is described in reference to FIG. 6 herebelow.

Referring now to FIGS. 5A and 5B, side and side sectional views of the distal portion of a light-energy delivering tissue treatment device is illustrated, consistent with the present inventive concepts. Treatment device 500 comprises a shaft 511, typically a flexible shaft including one or more lumens and configured to be inserted into a patient, such as into the gastrointestinal tract via the patient's mouth. Shaft 511 can be advanced through or alongside an endoscope and/or over a guidewire, endoscope and guidewire not shown but such as is described in reference to FIG. 3 hereabove. Positioned on the distal end of shaft 511 is treatment assembly 540. In some embodiments, shaft 511 passes through all or a portion of treatment assembly 540, not shown but such as when treatment assembly 540 is positioned on a distal portion but proximal to the distal end of shaft 511 (e.g. similar to the positioning of treatment assembly 140 on shaft 111b of FIG. 3).

Treatment assembly 540 includes treatment element 545, an energy delivery element constructed and arranged to deliver laser or other tissue treating light configured to treat target tissue. Treatment element 545 is operably attached to conduit 541. Conduit 541 can include one or more filamentous elements selected from the group consisting of: conductive wires; optical fibers; rotatable shafts; fluid delivery lumens; insulating layers; and combinations of these. Treatment assembly 540 further includes an inflatable element, balloon 543, which surrounds treatment element 545 and can be radially expanded, such as by the delivery of one or more fluids to balloon 543 via a fluid delivery tube of conduit 541. Treatment assembly 540 can be configured to be expanded (e.g. balloon 543 expanded), such as to move closer to and/or contact an energy delivery zone of the present inventive concepts, such as an expansion performed prior to a delivery of laser or other light energy to treat target tissue proximate balloon 543.

Treatment assembly 540 and treatment element 545 can be constructed and arranged to fractionally deliver laser or other light energy to tissue, such as is described in reference to the fractional delivery of energy described in reference to FIGS. 1 and 3 hereabove. In some embodiments, fractional delivery is achieved by balloon 543 selectively passing light energy delivered by treatment element 545. Alternatively or additionally, fractional delivery can be achieved by treatment element 545 delivering one or more rays of light energy that each contact an energy delivery zone with a limited diameter (e.g. focused light), such as a single ray of light delivered in a scanning (e.g. rotating and/or translating) fashion, or light delivered from an optical element that produces multiple rays of light in an appropriate pattern, such as are described herebelow.

In embodiments where balloon 543 selectively passes light energy delivered by treatment element 545, balloon 543 can be configured as a partial shroud that blocks the majority of light emitted by treatment element 545 while selectively passing multiple rays of light energy. In these embodiments, balloon 543 can be configured to pass light energy through one or more apertures 542, such as a grid pattern of rows and/or columns of material transparent or at least partially transmissive to one or more wavelengths of light configured to treat target tissue, while the remaining portions of balloon 543 block (i.e. prevent transmission of) at least those wavelengths of light.

In embodiments where treatment element 545 is configured to deliver one or rays of light with limited diameter to tissue, treatment element 545 can include one or more optical components configured to focus and/or distribute the light rays. In these embodiments, all or a majority of balloon 543 can be transmissive of light emitted from treatment element 545.

In the fractional energy delivery approach, a relatively small proportion of an energy delivery zone receives energy treatment element 545. In some embodiments, small portions of the entire surface of multiple energy delivery zones receive energy, such as when treatment assembly 540 is repositioned after each energy delivery zone receives an allotment of light energy. In some embodiments, one or more energy delivery zones have an area between 1 $cm^2$ and 5 $cm^2$.

The small portions of an energy delivery zone receiving energy result in multiple treated target tissue segments that each includes an inward facing surface relatively positioned on the tissue surface receiving the energy. In some embodiments, the inward facing surfaces comprise an elliptical geometry, such as a circular geometry. Non-target or other tissue not receiving energy can be positioned between the multiple treated target tissue segments. These treated target tissue segments extend into the tissue, such as deeper into the wall of tubular tissue such as deeper through a mucosal layer and at least partially into a submucosal layer. In some embodiments, these treated target tissue segments including mucosal and submucosal tissue result in reshaping the mucosa and/or submucosa. Alternatively or additionally, this fractional treatment of the target tissue segments can reduce the submucosal surface area on which new mucosal tissue subsequently grows. In some embodiments, the target tissue segments inward facing surfaces collectively comprise a quantity of 50 to 3000 per square centimeter of tissue surface receive energy, such as approximately a quantity of 500 per square centimeter. The target tissue inward facing surfaces can each comprise a surface with an equivalent diameter of between 20 and 200 microns (i.e. a surface whose area is equivalent to a circle with a diameter between 20 and 200 microns). The target tissue inward facing portions positioned within an energy delivery zone can be treated sequentially, such as a sequential energy delivery by treatment element 545, when treatment element 545 comprises a scanning light delivery element. Alternatively or additionally, multiple target tissue inward facing portions positioned within an energy delivery zone can be treated simultaneously, such as when light delivered by treatment element 545 delivers light to tissue through one or more apertures 542.

A set of energy delivery zones can each comprise an axial length of between 0.5 and 3 cm in length. A treatment assembly 540 can be translated between energy deliveries, such as a translation of approximately between 0.5 cm and 3 cm, such as to allow a slight overlap between any two energy delivery zones, such as to cause a mating of boundaries of any two energy delivery zones and/or such as to provide a gap between any two energy delivery zones.

In a fractional approach, the ratio of energy delivery zone tissue receiving energy to energy delivery zone tissue not receiving energy can be between 0.1% and 90%, such as less than 50%, less than 20%, less than 10%, less than 5%, less than 2% or less than 1%. The target tissue segment inward facing surfaces can comprise a major axis of less than or equal to 100 microns. The target tissue can be exposed to a temperature greater than or equal to 60° C., between 60° C. and 80° C., or a temperature greater than or equal to 100° C. In some embodiments, at least a portion of the target tissue is vaporized.

In some embodiments, treatment element 545 comprises a laser or other light energy source and/or is optically or otherwise coupled to a light energy source (e.g. EDU 330 of FIG. 3), such as via conduit 541. In some embodiments, the light source comprises a laser source selected from the group consisting of: CO2; Erbium; fiber laser; solid state crystal laser such as a Ho:YAG laser; semiconductor laser; and combinations of these. In some embodiments, treatment element 545 delivers light with a wavelength selected from the group consisting of: 2.0 to 2.2 micron; 1.8 to 2.0 micron; 1.24 to 1.64 micron; and combinations of these. Treatment element 545 can be constructed and arranged to deliver light energy in an array of light beams and/or to include an energy distribution element comprising a rotating element such as a rotating mirror; prism; diffractive optic; and combinations of these. Treatment element 545 can comprise one or more optical components, such as an array of lenses constructed and positioned to distribute multiple rays of light energy. An array of lenses can include two or more lenses selected from the group consisting of: holographic lens; fresnel lens; and combinations of these.

In some embodiments, treatment element 545 comprises a light-scattering material 544, such as to scatter light within balloon 543, such as to cause uniform distribution of light through apertures 542. In some embodiments, light-scattering material 544 is positioned outside treatment element 545 but within balloon 543, such as when balloon 543 is inflated with light-scattering material 544. Light-scattering material 544 can comprise a fluid or otherwise flowable medium including one or more of: reflective polystyrene particles; aluminum flakes; and reflective microspheres.

In some embodiments, conduit 541 comprises one or more fibers configured to deliver laser light with a high-water absorption wavelength (e.g. 1.9 or 2.1 microns) delivered to balloon 543 to be scattered via light-scattering material 544 through apertures 542. Balloon 543 can be coated with opaque paint and apertures created during the manufacturing process where salt or other dissolvable material is mixed in with the opaque paint and subsequently dissolved after the paint is dry. The size of the salt crystals used can be configured to create correspondingly sized apertures.

Referring now to FIG. 6, a side sectional view of the distal portion of a treatment device inserted into a curvilinear section of the GI tract is illustrated, consistent with the present inventive concepts. A GI tract portion, tubular segment GI1, includes one or more portions to be treated, such as one or more portions selected in the method of FIG. 2 described hereabove. One or more curvilinear portions of tubular segment GI1 (e.g. those comprising a sharp bend) can be selected to not receive treatment (e.g. segments that do not include an energy delivery zone). As shown, treatment device 100 has been inserted into segment GI1. Treatment device 100 comprises shaft 110, a relatively flexible, biocompatible, elongate structure configured for insertion into a body lumen such as the duodenal tissue shown. Shaft 110 is typically connected to a handle on its proximal end, not shown but configured to allow an operator to advance, retract and otherwise manipulate or control ablation device 100. Treatment device 100 can be configured for delivery over a guidewire, via a lumen from a proximal portion to a distal portion, or via a rapid exchange sidecar in the distal portion of the device (guidewire lumen and sidecar not shown but known to those of skill in the art). Shaft 110 can be inserted through an introducer comprising an endoscope, sheath, or other body introduction device, such as introducer 50 of FIG. 4 described hereabove.

Treatment device 100 further comprises treatment assembly 140, which can be similar to treatment assembly 140 of FIG. 3. Treatment assembly 140 can be expandable and/or it can include one or more expandable elements. Treatment assembly 140 comprises treatment element 145, which is constructed and arranged to deliver energy to one or more portions of an energy delivery zone and to treat one or more portions of target tissue. Treatment element 145 can comprise one or more treatment elements such as a balloon configured to receive sufficiently hot or cold ablative fluid; a fluid delivery element such as a nozzle configured to deliver ablative fluid directly onto tissue; one or more electrodes configured to deliver RF energy to tissue; a light energy delivery element such as a laser light energy delivery element described in reference to FIGS. 5A and 5B hereabove; and/or other ablation or other tissue treatment elements such as those described in reference to FIG. 3 hereabove.

Tubular segment GI1 includes at least three energy delivery zones, EDZ1, EDZ2 and EDZ3, which are selected for treatment, such as by receiving energy from treatment assembly 140 in a series of energy deliveries as described in reference to FIG. 4 hereabove. In some embodiments, one or more curvilinear portions of tubular segment GI1 are not treated (e.g. those segments do not include an energy delivery zone), such as curvilinear segment CS1 and/or curvilinear segment CS2 as shown. In some embodiments, one or more axial segments of tissue in a curvilinear portion of duodenal or other gastrointestinal tissue is not treated) if the one or more axial segments comprise a curvilinear portion with an approximate average radius of curvature less than 5 cm over a 75 degree arc. In some embodiments, curvilinear segment 1 comprises an average radius of curvature less than 5 cm over a 75 degree arc and is not treated. In some embodiments, curvilinear segment 2 comprises an average radius of curvature greater than 5 cm over a 75 degree arc and is treated (i.e. includes a fourth energy delivery zone, not shown). In some embodiments, an axial segment of tissue proximate to the ampulla of Vater can be specifically excluded from an energy delivery zone to avoid damage to this structure.

As shown in FIG. 6, treatment assembly 140 has been positioned in energy delivery zone EDZ2, such as to deliver energy to an axial segment of energy delivery zone EDZ2. Treatment assembly has treated and/or will deliver energy to all surfaces of energy delivery zones EDZ1, EDZ2 and EDZ3, such as via advancement or retraction between energy deliveries as has been described herein, such that the selected target tissue of segment GI receives proper treatment.

Referring now to FIGS. 7A, 7B and 7C, end sectional views of a tubular segment of GI tissue are illustrated, prior to tissue expansion, after tissue expansion and after target tissue treatment, respectively, consistent with the present inventive concepts. In FIG. 7A, tubular segment GI1 can include a tubular segment of the duodenum and/or jejunum. Tubular segment GI1 can include one or more inner layers L1, and one or more outer layers L2. Layers L1 can include the mucosal layer and one or more inner layers of the submucosa. Layers L2 can include the gastrointestinal adventitia, the tunica serosal, the tunica muscularis and/or the outermost partial layer of the submucosa.

In FIG. 7B, a tissue expansion of one or more layers of layers L1 has been performed, such as a tissue expansion of one or more layers of submucosal tissue performed by a tissue expansion device such as treatment device 100 and/or tissue expansion device 200 of FIG. 3 described hereabove. Expansion of layer 1 can create one or more "peaks" and "valleys" on the inner surface of GI1, such as surface peaks $L1_p$ and surface valleys $L1_v$ as shown in FIG. 7B. Also as shown in FIG. 7B, a treatment device 100 has been advanced such that treatment assembly 140 is positioned within tubular segment GI1. Treatment device 100 and treatment assembly 140 can be configured as described in reference to treatment device 100 and treatment assembly 140 described in reference to FIG. 3 hereabove.

In FIG. 7C, treatment assembly 140 has been expanded to contact at least the majority of the surface of surface peaks $L1_p$. Energy, such as energy delivered from a hot fluid balloon or other energy delivery element described herein, is delivered from treatment assembly 140 to the contacted tissue of surface peaks $L1_p$. In some embodiments, at least a portion of the surface of surface valleys $L1_v$ do not receive energy from treatment assembly 140, such that target tissue TT1 includes multiple partial circumferential tissue segments separated by gaps of untreated tissue.

Referring now to FIGS. 8A, 8B and 8C, end sectional views of a tubular segment of GI tissue are illustrated, prior to tissue expansion, after tissue expansion and after target tissue treatment, respectively, consistent with the present inventive concepts. In FIG. 8A, tubular segment GI1 can include a tubular segment of the duodenum and/or jejunum. Tubular segment GI1 can include one or more inner layers L1, and one or more outer layers L2. Layers L1 can include the mucosal layer and one or more inner layers of the submucosa. Layers L2 can include the gastrointestinal adventitia, the tunica serosal, the tunica muscularis and/or the outermost partial layer of the submucosa.

In FIG. 8B, a tissue expansion of one or more layers of layers L1 has been performed, such as a tissue expansion of one or more layers of submucosal tissue performed by a tissue expansion device such as treatment device 100 and/or tissue expansion device 200 of FIG. 3 described hereabove. Expansion of layer 1 can create one or more "peaks" and "valleys" on the inner surface of GI1, such as surface peaks $L1_p$ and surface valleys $L1_v$ as shown in FIG. 8B. Also as shown in FIG. 8B, a treatment device 100 has been advanced such that treatment assembly 140 is positioned within tubular segment GI1. Treatment device 100 and treatment assembly 140 can be configured as described in reference to treatment device 100 and treatment assembly 140 described in reference to FIG. 3 hereabove.

In FIG. 8C, treatment assembly 140 has been expanded to contact at least the majority of the surface of surface peaks $L1_p$. In some embodiments, treatment assembly 140 makes contact with the majority of the surface of surface peaks $L1_p$ and the majority of the surface of surface valleys $L1_v$, and/or is configured to deliver energy to the majority of the surface of surface peaks $L1_p$ and the majority of the surface of surface valleys $L1_v$. Target tissue TT1 comprises a full circumferential layer of tissue with non-uniform thickness along its circumference, such as target tissue whose thickness differs at the locations of surface peaks $L1_p$ and surface valleys $L1_v$, such as is shown in FIG. 8C.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A system for fractionally delivering energy to a tissue treatment zone in a gastrointestinal tract duodenum of a patient, said system comprising:
   an elongate shaft with a distal portion;
   a tissue treatment assembly positioned on the elongate shaft, wherein the tissue treatment assembly is configured to deliver energy to 50 to 3000 inward facing target surfaces per square centimeter of target tissue positioned in at least one energy delivery zone; and
   an energy delivery unit connected to the tissue treatment assembly and configured to deliver energy to at least a portion of the 50 to 3000 discrete inward facing surfaces of each energy delivery zone and not to deliver energy to non-target tissue positioned between each of the inward facing target surfaces of the at least one energy delivery zone to safely reduce the luminal surface area of at least a portion of the gastrointestinal tract duodenum.

2. The system of claim 1, wherein the energy delivery unit comprises controller configured to control target tissue temperature or target tissue treatment duration.

3. The system of claim 1, wherein the tissue treatment assembly is configured to treat inward facing surfaces each having an equivalent diameter between approximately 20 and 200 microns.

4. The system of claim 1, wherein the tissue treatment assembly is configured to treat target tissue at a temperature at or above 60° C.

5. The system of claim 4, wherein the tissue treatment assembly is configured to treat target tissue at a temperature at or above 100° C.

6. The system of claim 1, wherein the tissue treatment assembly comprises an expandable portion configured to expand to a diameter between 10 and 40 mm.

7. The system of claim 1, wherein the tissue treatment assembly is constructed and arranged to deliver energy to fewer than all of a multiplicity energy delivery zones.

8. The system of claim 1, wherein the shaft comprises a bulbous element positioned on the distal portion.

9. The system of claim 1, further comprising a tissue expansion element configured to expand a wall of the gastrointestinal tract duodenum.

10. The system of claim 1, wherein the tissue treatment assembly is configured to deliver energy to multiple tissue segments of the duodenum.

11. The system of claim 10, wherein the tissue treatment assembly is configured to deliver energy to between 2 and 50 tissue segments of the duodenum.

12. The system of claim 10, wherein the multiple tissue segments each comprise a length less than 15 cm.

13. The system of claim 1, further comprising a pumping assembly constructed and arranged to deliver or remove fluid from the tissue treatment element.

14. The system of claim 1, wherein the energy delivery unit is configured to reduce at least one of absorption or secretion of the at least a portion of the duodenum.

15. The system of claim 1, wherein the system is constructed and arranged to treat diabetes.

16. The system of claim 1, wherein the tissue treatment assembly is constructed and arranged to cause a reduction in a duodenal tissue characteristic selected from the group consisting of: average height of mucosal folds; surface area of mucosal folds; number of mucosal folds; and combinations thereof.

17. The system of claim 1, wherein the tissue treatment assembly is constructed and arranged to reduce the surface area of the treated portion of the duodenum by at least 5%.

18. The system of claim 1, wherein at least 1% of the energy delivery zone receives energy from the tissue treatment assembly.

19. The system of claim 1, wherein at least 2% of the energy delivery zone receives energy from the tissue treatment assembly.

20. The system of claim 1, wherein at least 5% of the energy delivery zone receives energy from the tissue treatment assembly.

21. The system of claim 1, wherein at least 10% of the energy delivery zone receives energy from the tissue treatment assembly.

22. The system of claim 1, wherein at least 50% of the energy delivery zone receives energy from the tissue treatment assembly.

23. The system of claim 1, wherein the tissue treatment assembly comprises an array of micro-electrodes or a light source that delivers multiple rays of light to a tissue surface simultaneously.

24. The system of claim 23, wherein the treatment assembly comprises a light treatment element and a partial shroud that blocks a majority of light emitted by the light treatment element while selectively passing multiple rays of light energy.

25. The system of claim 23, wherein the treatment assembly comprises an array of micro-electrodes.

* * * * *